United States Patent
Allington et al.

(10) Patent No.: US 7,922,908 B2
(45) Date of Patent: *Apr. 12, 2011

(54) SEPARATION SYSTEM, COMPONENTS OF A SEPARATION SYSTEM AND METHODS OF MAKING AND USING THEM

(75) Inventors: Robert W. Allington, Lincoln, NE (US); Shaofeng Xie, Lincoln, NE (US); Tao Jiang, Lincoln, NE (US); Mingcheng Xu, Lincoln, NE (US)

(73) Assignee: Dionex Corporation, Sunnyvale, CA (US)

( * ) Notice: Subject to any disclaimer, the term of this patent is extended or adjusted under 35 U.S.C. 154(b) by 1142 days.

This patent is subject to a terminal disclaimer.

(21) Appl. No.: 11/337,071

(22) Filed: Jan. 19, 2006

(65) Prior Publication Data

US 2006/0207939 A1    Sep. 21, 2006

Related U.S. Application Data

(63) Continuation of application No. 10/607,080, filed on Jun. 25, 2003, now Pat. No. 7,074,331, which is a continuation-in-part of application No. 10/180,350, filed on Jun. 26, 2002, now Pat. No. 6,749,749.

(51) Int. Cl.
  *B01D 15/08* (2006.01)
(52) U.S. Cl. .................. 210/635; 210/656; 210/748.01; 210/198.2; 210/502.1
(58) Field of Classification Search .................. 210/656, 210/635, 659, 748.01, 198.2, 502.1; 95/88; 96/101

See application file for complete search history.

(56) References Cited

U.S. PATENT DOCUMENTS

| | | |
|---|---|---|
| 2,537,951 A | 1/1951 | Amos |
| 3,246,767 A | 4/1966 | Pall et al. |
| 3,353,682 A | 11/1967 | Pall et al. |
| 3,598,728 A | 8/1971 | Bixler et al. |
| 3,663,263 A | 5/1972 | Bodre et al. |
| 3,696,061 A | 10/1972 | Selsor et al. |

(Continued)

FOREIGN PATENT DOCUMENTS

CS         211743         2/1982

(Continued)

OTHER PUBLICATIONS

Anon. Monolithic matrix accelerates separation, High Tech Separations News, 14(2):1-2 (Jul. 2001).

(Continued)

*Primary Examiner* — Ernest G Therkorn
(74) *Attorney, Agent, or Firm* — Morgan, Lewis & Bockius LLP; David J. Brezner

(57) ABSTRACT

Permeable polymeric monolithic materials are prepared in a column casing. In one embodiment, the permeable polymeric monolithic materials are polymerized while pressure is applied through a piston having a smooth piston head in contact with the polymerization mixture. The pressure eliminates wall effect and changes the structure in the column. Similarly, some columns that have a tendency to swell in the presence of aqueous solutions and pressurized while the solution is applied to prevent swelling and wall effect. This procedure also changes the structure in the column. The size of the separation effective openings can be controlled by the amount of the pressure and pores eliminated. Uniformity in the direction flow is improved by controlling polymerization with radiation rather than with conducted heat.

7 Claims, 11 Drawing Sheets

U.S. PATENT DOCUMENTS

| | | | |
|---|---|---|---|
| 3,796,657 | A | 3/1974 | Pretorius et al. |
| 3,808,125 | A | 4/1974 | Good |
| 3,878,092 | A | 4/1975 | Fuller |
| 3,954,608 | A | 5/1976 | Valentin |
| 4,031,037 | A | 6/1977 | Kalal et al. |
| 4,045,353 | A | 8/1977 | Kosaka et al. |
| 4,087,391 | A | 5/1978 | Quentin |
| 4,102,746 | A | 7/1978 | Goldberg |
| 4,169,014 | A | 9/1979 | Goldberg |
| 4,283,280 | A | 8/1981 | Brownlee |
| 4,313,828 | A | 2/1982 | Brownlee |
| 4,340,483 | A | 7/1982 | Lukas et al. |
| 4,385,991 | A | 5/1983 | Rosevear et al. |
| 4,430,216 | A | 2/1984 | Ito |
| 4,447,328 | A | 5/1984 | Kamiyama et al. |
| 4,464,240 | A | 8/1984 | Hansen |
| 4,465,571 | A | 8/1984 | Hansen |
| 4,477,492 | A | 10/1984 | Bergna et al. |
| 4,486,311 | A | 12/1984 | Nakajima et al. |
| 4,497,710 | A | 2/1985 | Wagu et al. |
| 4,509,964 | A | 4/1985 | Hubball et al. |
| RE31,974 | E | 8/1985 | Brownlee |
| 4,565,832 | A | 1/1986 | Kobashi et al. |
| 4,747,956 | A | 5/1988 | Kiniwa |
| 4,794,177 | A | 12/1988 | Peska et al. |
| 4,889,632 | A | 12/1989 | Svec et al. |
| 4,913,812 | A | 4/1990 | Moriguchi et al. |
| 4,923,610 | A | 5/1990 | Svec et al. |
| 4,952,349 | A | 8/1990 | Svec et al. |
| 5,019,270 | A | 5/1991 | Afeyan et al. |
| 5,130,343 | A | 7/1992 | Frechet et al. |
| 5,135,650 | A | 8/1992 | Hjerten et al. |
| 5,137,659 | A | 8/1992 | Ashley et al. |
| 5,145,579 | A | 9/1992 | Eguchi et al. |
| 5,167,822 | A | 12/1992 | Simon et al. |
| 5,183,885 | A | 2/1993 | Bergot |
| 5,186,838 | A | 2/1993 | Simon et al. |
| 5,200,150 | A | 4/1993 | Rose, Jr. |
| 5,211,993 | A | 5/1993 | Kolesinski |
| 5,228,989 | A | 7/1993 | Afeyan et al. |
| 5,306,426 | A | 4/1994 | Afeyan |
| 5,306,561 | A | 4/1994 | Frechet et al. |
| 5,334,310 | A | 8/1994 | Frechet et al. |
| 5,384,042 | A | 1/1995 | Afeyan et al. |
| 5,389,449 | A | 2/1995 | Afeyan et al. |
| 439,593 | A | 8/1995 | Price |
| 5,453,185 | A | 9/1995 | Frechet et al. |
| 5,503,933 | A | 4/1996 | Afeyan et al. |
| 5,552,041 | A | 9/1996 | Afeyan et al. |
| 5,605,623 | A | 2/1997 | Afeyan et al. |
| 5,645,717 | A | 7/1997 | Hjerten et al. |
| 5,647,979 | A | 7/1997 | Liao et al. |
| 5,728,457 | A | 3/1998 | Frechet et al. |
| 5,767,387 | A | 6/1998 | Wang |
| 5,814,223 | A | 9/1998 | Hjerten et al. |
| 5,833,861 | A | 11/1998 | Afeyan et al. |
| 5,916,445 | A | 6/1999 | Hjerten et al. |
| 5,935,429 | A | 8/1999 | Liao et al. |
| 6,210,570 | B1 | 4/2001 | Holloway |
| 6,238,565 | B1 | 5/2001 | Hatch |
| 6,248,798 | B1 | 6/2001 | Slingsby et al. |
| 6,318,157 | B1 | 11/2001 | Corso et al. |
| 6,572,766 | B1 | 6/2003 | Bergstrom et al. |
| 6,616,825 | B1* | 9/2003 | Frechet et al. ............ 204/605 |
| 6,770,201 | B2 | 8/2004 | Shepodd et al. |
| 7,074,331 | B2 | 7/2006 | Allington et al. |
| 7,235,199 | B2 | 6/2007 | Lubda et al. |
| 7,473,367 | B2* | 1/2009 | Xie ............................ 210/635 |
| 2001/0023848 | A1 | 9/2001 | Gjerde et al. |
| 2001/0030156 | A1 | 10/2001 | Gjerde et al. |
| 2001/0032817 | A1 | 10/2001 | Gjerde et al. |
| 2002/0038786 | A1 | 4/2002 | Gjerde et al. |
| 2002/0079257 | A1 | 6/2002 | Zare et al. |
| 2002/0088753 | A1 | 7/2002 | Huber et al. |
| 2002/0166816 | A1 | 11/2002 | Allen et al. |
| 2003/0062308 | A1 | 4/2003 | Zare et al. |
| 2003/0062309 | A1 | 4/2003 | Zare et al. |
| 2003/0062310 | A1 | 4/2003 | Zare et al. |
| 2004/0000522 | A1 | 1/2004 | Xie et al. |
| 2005/0155933 | A1* | 7/2005 | Ma ............................ 210/656 |

FOREIGN PATENT DOCUMENTS

| | | |
|---|---|---|
| DE | 35 43 348 A1 | 6/1987 |
| DE | 39 00 272 A1 | 7/1990 |
| DE | 43 33 821 A1 | 4/1995 |
| DE | 43 34 351 A1 | 4/1995 |
| DE | 199 05 117 A1 | 8/2000 |
| DE | 100 28 447 A1 | 12/2001 |
| EP | 0 101 982 A2 | 3/1984 |
| EP | 0 129 295 A2 | 12/1984 |
| EP | 0 180 321 A2 | 5/1986 |
| EP | 0 231 684 A1 | 8/1987 |
| EP | 0 264 984 A1 | 4/1988 |
| EP | 0 272 925 A2 | 6/1988 |
| EP | 0 282 177 A2 | 9/1988 |
| EP | 0 320 023 A2 | 6/1989 |
| EP | 0 399 318 A1 | 5/1990 |
| EP | 534 567 A2 | 3/1993 |
| EP | 0 407 560 B1 | 6/1995 |
| EP | 0 813 062 A2 | 12/1997 |
| EP | 0 852 334 A1 | 7/1998 |
| GB | 1188736 A | 4/1970 |
| JP | 63-84641 A | 4/1988 |
| JP | 11 064314 | 3/1999 |
| WO | WO 89/07618 A1 | 8/1989 |
| WO | WO 90/07965 A1 | 7/1990 |
| WO | WO 95/22555 A1 | 8/1995 |
| WO | WO 99/15024 A1 | 4/1999 |
| WO | WO 99/44053 A2 | 9/1999 |
| WO | WO 99/44053 A3 | 9/1999 |
| WO | WO 00/15321 A1 | 3/2000 |
| WO | WO 00/15778 A1 | 3/2000 |
| WO | WO 00/52455 A1 | 9/2000 |
| WO | WO 01/57263 A1 | 8/2001 |
| WO | WO 01/93974 A1 | 12/2001 |
| WO | WO 2004/002603 A1 | 1/2004 |

OTHER PUBLICATIONS

Xie, S, RW Allington, F Svec, JMJ Frechet. Rapid reversed-phase separation of proteins and peptides using optimized "moulded" monolithic poly(styrene-co-divinylbenzene) columns, J. Chromatogr. A 865:169-174 (1999).

Xie, S.. Monolithic macroporous poly(styrene-co-divinylbenzene) columns for rapid or high throughput reversed-hase separation of proteins and peptides, Poster Presentation, International Symposium, San Francisco, CA (1999).

Liao, J-L, Y-M Li, S. Hjerten. Continuous beds for microchromatography: reversed-phase chromatography, Anal. Biochem. 234:27-30 (1996).

Brochure: "Quick Disk," Saulentechnik/Knauer.

Brochure: "ConSep™ LC100 System", Millipore Corp.

Brochure: "MemSep® Chromatography Cartridges", Millipore Corp.

Czechoslovakian Academy of Sciences, A process for the preparation of macroporous polymers, (sic: PTO 91-4925 Patent Application No. 6803739) Oct. 3, 1991.

Peters, EC, F. Svec and JJM Frechet. Preparation of large-diameter "molded" porous polymer monoliths and the control of pore structe homogeneity, Chem. Mater. 9:1898-1903 (1997).

Advertisement: "ConSep™," Millipore Corporation, Genet. Eng. News (Sep. 15, 1983).

Afeyan, N., et al., "Flow-through particles for the high performance liquid chromatographic separation of biomolecules: perfusion chromatography," J. Chromatogr. 519:1-29 (1990).

Afeyan, N., et al., "Perfusion chromatography packing materials for proteins and peptides," J. Chromatogr. 544:267-279 (1991).

Braun, T., et al., "Polyurethane foams and microspheres in analytical chemistry," Anal. Chim. Acta 99:1-36 (1978).

Cooper, A., et al., "Coiled high-efficiency liquid chromatography columns," Separation Sci. 11(1);39-44 (1976).

Elderfield, H., "Carbonate mysteries," Science 296:1618-1621 (May 2002).

Grasselli, M., et al., "From microspheres to monoliths: synthesis of porous supports with tailored properties by radiation polymerization," *Nucl. Instr. Meths. Phys. Res. B* 185:254-261 (Dec. 2001).

Herman, D., et al., "Surface modified open-pore polyurethane packings for liquid chromatography," *J. Chromatogr. Sci.* 20:55-61 (1982).

Hileman, F., et al., "In situ preparation and evaluation of open pore polyurethane chromatographic columns," *Anal. Chem.* 45(7):1126-1130 (1973).

Hjerten, S., et al., The design of agarose beds for high-performance hydrophobic-interaction chromatography and ion-exchange chromatography which show increasing resolution with increasing flow rate, *Makromol. Chromatogr., Macromol. Symp.* 17:349-357 (1988).

Hjerten, S., et al., "High performance liquid chromatography of proteins on compressed, non-porous agarose beads," *J. Chromatogr.* 457:165-174 (1988).

Hjerten, S., et al., "High performance liquid chromatography on continuous polymer beds," *J. Chromatogr.* 473:273-275 (1989).

Horak, D., et al., "Reactive polymers: 61. Reaction of macroporous poly(glycidyl methacrylate-co-ethylene dimethacrylate) with phenol," *Polymer* 32(6):1135-1139 (1991).

Hradil, J., et al., "Ion chromatography on methacrylate ion exchangers," *J. Chromatogr.* 475:209-217 (1989).

Liao, J., et al., "Continuous beds for microchromatography: reversed-phase blotting membrane techniques," *Anal. Biochem.* 241:195-198 (1996).

Liao, J., et al., "Continuous beds for standard and micro high-performance liquid chromatography," *J. Chromatogr.* 586:21-26 (1991).

Lynn, T., et al., High resolution low pressure liquid chromatography, *J. Chromatogr. Sci.* 12:76-79 (1974).

Navratil, J., et al., "Chemical separations with open-pore polyurethane," *Amer. Lab.* 9(10):38-42 (1977).

Navratil, J., et al., "Open-pore polyurethane columns for collection and preconcentration of polynuclear aromatic hydrocarbons from water," *Anal. Chem.* 49(14):2260-2263 (1971).

Pelzbauer, Z., et al., "Reactive polymers. XXV. Morphology of polymeric sorbents based on glycidyl mathacrylate copolymers," *J. Chromatogr.* 171:101-107 (1979).

Peters, E., et al., "Chiral electrochromatography with a 'moulded' rigid monolithic capillary column," *Anal. Commun.* 35:83-86 (1998).

Premstaller, A., et al., "High performance liquid chromatography electrospray ionization mass spectrometry of single-and double-stranded nucleic acids using monolithic capillary columns," *Anal. Chem.* 72(18):4386-4393 (Sep. 2000).

Reusch, J., et al., *Konigsteiner Chromatographietage*, p. 158 (1991).

Ross, W., "Open pore polyurethane—a new separation medium," *Separation and Purification Meth.* 3(1):111-131 (1974).

Ross, W., et al., "In situ formed open-pore polyurethane as chromatography supports," *J. Chromatogr. Sci.* 8:386-389 (1970).

Ross, W., et al., "In situ open-pore polyurethane as chromatography supports," *Adv. Chromatogr. Proc. Intl. Symp.*, 6th annual, (1970).

Salyer, I., et al., "Preparation and properties of open pore polyurethane," 163rd *Natl. ACS Mtg.*, Boston, MA (Apr. 1972).

Salyer, I., et al., "Preparation and properties of open pore polyurethane (OPP)," *J. Cell. Plastics* 9:25-34 (1973).

Sanfranj, A., et al., "Functional polymeric microspheres synthesized by radiation polymerization," *Radiat. Phys. Chem.* 46(2):203-206 (1995).

Snyder, L., et al., "Introduction to Modern Liquid Chromatography," 2nd ed., pp. 183-1895, 203-204, 492-494, John Wiley & Sons, Inc.: San Francisco, CA (1979).

Sun, X., et al., "Urea-formaldehyde resin monolith as a new packing material for affinity chromatography," *J. Chromatogr. A* 943:209-218 (2002).

Tennikova, T., et al., "High performance membrane chromatography. A novel method of protein separation," *J. Liquid Chromatogr.* 13(1):63-70 (1990).

Usmani, A., et al., "Applications of porous urea/formaldehyde polymers," *J. Macromol. Sci. Chem. A* 19(8&9):1237-1246 (1983).

Wang, B., et al., "Viscometric and light scattering studies on microgel formation by $y$-ray irradiation to aqueous oxygen-free solutions of poly(vinyl alcohol)," *Langmuir* 13:6108-6114 (1997).

Xie, S., "High-speed bioseparation with monolithic columns," Poster No. 1659P, *Bioanalytical Separation Session, PITTCON2001*, New Orleans, LA (Mar. 5, 2001).

Xie, S., "Macroporous poly(styrene-co-divinyl-benzene) monoliths for high throughput reversed-phase separation of biomolecules," 217[th i ACS Natl. Mtg.]., Anaheim, CA (Mar. 21, 1999).

Xie, S., et al., "Applications of polymeric monolith columns for fast bioseparations," *ISPP2000: The 20th Intl. Symp. on Separation and Analysis of Proteins, Peptides and Polynucleotides*, Ljubljana, SI (Nov. 5-8, 2000).

Xie, S., et al., "High throughput bioseparations in monolithic ion exchangers," *HPLC2000*, Seattle, WA (Jun. 24-30, 2000).

Xie, S., et al., "Rapid bioseparations in columns with monolithic separation media," *PITTCON2000*, New Orleans, LA (Mar. 5, 2001).

\* cited by examiner

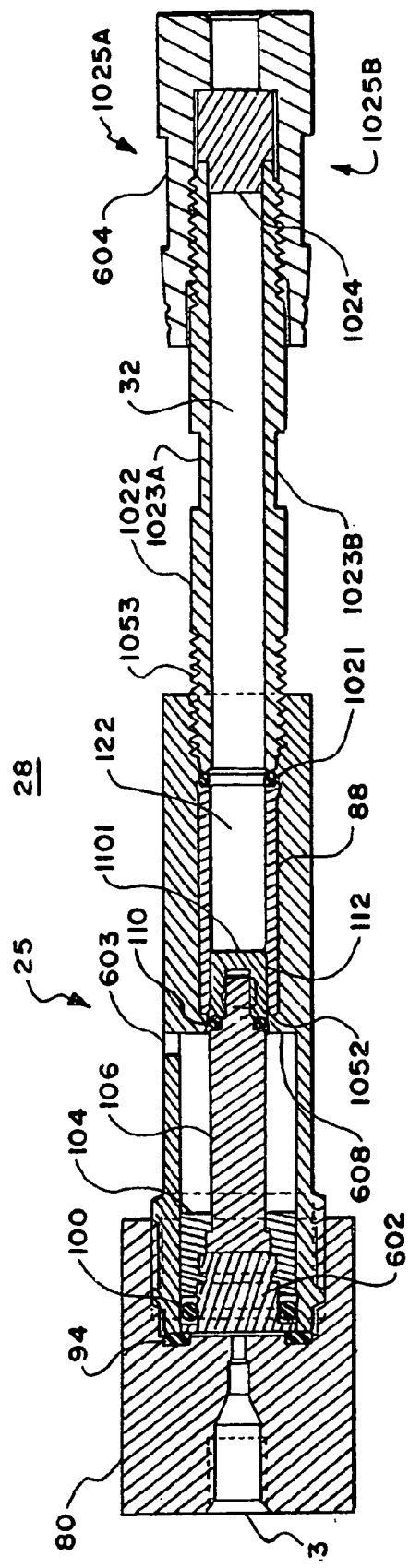
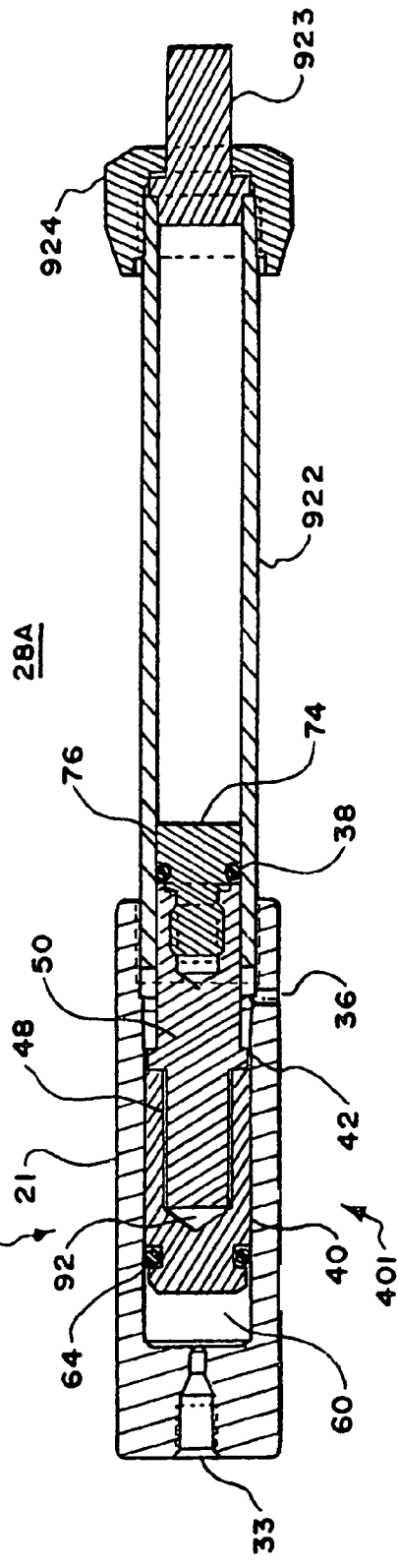
FIG. 3
FIG. 4

SEPARATION SYSTEM, COMPONENTS OF A SEPARATION SYSTEM AND METHODS OF MAKING AND USING THEM

RELATED CASES

This application is a continuation of U.S. patent application Ser. No. 10/607,080, filed Jun. 25, 2003 now U.S. Pat. No. 7,074,331, which is a continuation in part of U.S. patent application Ser. No. 10/180,350 filed Jun. 26, 2002 (now U.S. Pat. No. 6,749,749 issued Jun. 15, 2004), in the names of Shaofeng Xie and Robert W. Allington for SEPARATION SYSTEM, COMPONENTS OF A SEPARATION SYSTEM AND METHODS OF MAKING AND USING THEM.

BACKGROUND OF THE INVENTION

This invention relates to separation systems and their components and more particularly to separation systems and components involving monolithic permeable polymeric materials.

Monolithic macroporous materials such as for example organic monolithic macroporous polymeric materials and monolithic silica packings are known as components for separation systems such as chromatographic or extraction systems. One class of such materials is formed as a monolithic macroporous polymer plug or solid support produced by polymerizing one or more monomers in a polymerization mixture that includes at least a porogen. It is known for some polymerization mixtures, to include other materials such as cross-linking agents, catalysts and small soluble polymers which can be dissolved after polymerization to control the porosity and pore size distribution. Moreover, the plug may be modified after being formed to add functional groups.

The plug or solid support is normally contained in a housing such as for example a chromatographic column or a pressure vessel. The portion of the housing where the plug resides acts as a reactor. In one prior art process for making monolithic columns, the polymerization mixture may be added to the column casing and polymerization initiated therein to form a macroporous polymeric plug or solid support within the walls of the column.

There are wide applications of these plugs or solid supports including gas, liquid and supercritical fluid chromatography, membrane chromatography and filtration, solid phase extraction, catalytic reactors, solid phase synthesis and others. The efficiency of the column or other container for the plug or solid support, the time required for a separation, and the reproducibility of the columns or other container for the plug or solid support are important commercial factors. The efficiency of separation systems such as chromatographic columns with porous polymer in them is related to both the selectivity of the column or other component containing the macroporous polymeric material and to zone spreading. Some of these factors are affected by molecular diffusion and velocity of the mobile phase in the plug or solid support during a separation process.

The manner in which molecular diffusion and velocity of the mobile phase affects column efficiency can be in part explained by showing the effect of these factors on Height Equivalent to Theoretical Plates (HETP), the conventional designation of column efficiency. The van Demeter Equation shows the relationship between zone spreading, flow velocity and diffusion in terms of H (HETP) as follows:

H=A+B/u+Cu with low H corresponding to high efficiency
U=Flow velocity of the mobile phase
A=Radial Eddy Diffusion coefficient
B=Longitudinal Molecular Diffusion coefficient
C=The mass transfer coefficient Molecular diffusion depends on the diffusion of the molecules but not on the packing of the bed. Eddy diffusion depends on the homogeneity of the packing of the particles.

Zone spreading from mass transfer can be minimized by using non-porous particles and porous particle with sizes smaller than 1.5 microns. However, packing with non-porous particles has extremely low surface area which is detrimental to the purification process (as opposed to the analytical process) because the purification process requires high sample loading. The use of very small packed particles requires either high pressure which is difficult in most of the separation process using current instrumentation or low velocity which can increase the time for a given separation (sometimes expressed in H per minute).

The prior art separation systems that include as a component macroporous polymeric monolithic plugs or solid supports use plugs or solid supports formed from particles in the polymers that are larger than desired, less homogenous and include micropores. The large size of the particles and their lack of homogeneity result in a lack of homogeneity in the pore size distribution. The non-homogeneity of the pore sizes and large amount of micropores in the prior art porous polymers contributes greatly to the zone spreading as shown by the van Demeter Equation. The large number of micropores contributes to zone spreading by capturing sample and retaining it for a time. This may be stated conventionally as the non-equilibrium mass transfer in and out of the pores and between the stationary phase and the mobile phase.

The prior art plugs or solid supports formed of porous polymers have lower homogeneity of pore size, less desirable surface features and voids in their outer wall creating by wall effect and thus higher zone spreading and lower efficiency than desired in separation systems.

The prior art also fails to provide an adequate solution to a problem related to shrinkage that occurs during polymerization and shrinkage that occurs after polymerization in some prior art porous polymers. The problem of shrinkage during polymerization occurs because monomers are randomly dispersed in the polymerization solution and the polymers consist of orderly structured monomers. Therefore, the volume of the polymers in most of the polymerization is smaller than the volume of the mixed monomers. The shrinkage happens during the polymerization in all of the above preparation processes. One of the problems with shrinkage after polymerization occurs because of the incompatibility of a highly hydrophilic polymer support with a highly hydrophilic aqueous mobile phase or other highly polar mobile phase such as for example, a solution having less than 5-8 percent organic solvent content.

Shrinkage of the porous polymeric materials used in separation systems and their components during polymerization results in irregular voids on the surface of the porous polymers and irregularity of the pore size inside the polymer, which are detrimental to the column efficiency and the reproducibility of the production process. One reason the column efficiency is reduced by wall effect is that wall effect permits the sample to flow through the wall channels and bypass the separation media. One reason the reproducibility of the production process are reduced by wall effect is the degree of wall effect and location of the wall effect are unpredictable from column to column.

The columns with large channels in the prior art patents cited above have low surface area and capacity. The low capacities of the columns are detrimental for purification process which requires high sample loadings. In spite of much effort, time and expense in trying to solve the problems of shrinkage, the prior art fails to show a solution to reduced capacity.

Because of the above phenomena and/or other deficiencies, the columns prepared by the above methods have several disadvantages, such as for example: (1) they provide columns with little more or less resolution than commercially available columns packed with beads; (2) the separations obtained by these methods have little more or no better resolution and speed than the conventional columns packed with either silica beads or polymer beads, particularly with respect to separation of large molecules; (3) the wide pore size distribution that results from stacking of the irregular particles with various shapes and sizes lowers the column efficiency; (4) the non-homogeneity of the pore sizes resulting from the non-homogeneity of the particle sizes and shapes in the above materials contribute heavily to the zone spreading; (5) the large amount of micropores in the above materials also contributes greatly to the zone spreading; and (6) shrinkage of the material used in the columns reduces the efficiency of the columns. These problems limit their use in high resolution chromatography.

U.S. Pat. No. 5,453,185 proposed a method of reducing the shrinkage by reducing the amount of monomers in the polymerization mixture using insoluble polymer to replace part of the monomers. This reduces the shrinkage but is detrimental to the capacity and retention capacity factor of the columns which require high amount of functional monomers. There is nothing mentioned in these patents regarding the detrimental effect of shrinkage on resolution and the resulting irregular voids on the surface of the porous polymer and irregularity of the pore size inside the polymer, which are detrimental to the column efficiency and the reproducibility of the production process.

Prior art European patent 1,188,736 describes a method of making porous poly(ethylene glycol methacrylate-co-ethylene glycol dimethacrylate) by in situ copolymerization of a monomer, a crosslinking agent, a porogenic solvent and an initiator inside a polytetrafuoroethylene tube sealed at one end and open at the other end. The resulting column was used for gas-liquid chromatography. This prior art approach has the disadvantage of not resulting in materials having the characteristics desirable for the practical uses at least partly because it uses polymerization in a plastic tube with an open end.

U.S. Pat. Nos. 2,889,632, 4,923,610 and 4,952,349 disclose a method of making thin macroporous membranes within a sealed device containing two plates and a separator. In this method the desired membrane support was punched out of a thin layer of porous polymer sheet and modified to have desired functional groups. The layers of porous sheets are held in a support device for "membrane separation". These patents extended the method described in European patent 1,188,736 to prepare a porous membrane and improve the technique for practical applications in membrane separation. The resulting material is a macroporous membrane including pores from micropores of size less than 2 nanometers to large pores. The size of the particles of the polymer is less than 0.5 micrometers. The separation mechanism of membrane separation is different from that of conventional liquid chromatography.

This porous material has several disadvantages, such as for example: (1) the thinness of the membrane limits its retention factor; and (2) the pores formed by these particles are small and can not be used at high flow rate with liquid chromatography columns that have much longer bed lengths than the individual membrane thicknesses. The micropores and other trapping pores trap molecules that are to be separated and contribute to zone spreading. The term "trapping pore" in this specification means pores that contribute to zone spreading such as pores ranging in size from slightly larger than the molecule being separated to 7 times the diameter of the pore being separated.

U.S. Pat. Nos. 5,334,310; 5,453,185 and 5,728,457 each disclose a method of making macroporous poly(glycidyl methacrylateco-ethylene glycol dimethacrylate) polystyrene in situ within sealed columns. This method extends the methods described in both the European patent 1,188,736 and U.S. Pat. Nos. 2,889,632, 4,923,610 and 4,952,349 for preparing liquid chromatography columns for the separation of proteins. U.S. Pat. Nos. 5,334,310, 5,453,185 and 5,728,457 profess the intention of improving the column efficiency by removing the interstitial volume of conventional packed columns having beads. The plugs formed according to these patents have a pore size distribution that is controlled by the type and amount of porogens, monomers and polymerization temperature. The macroporous polymers consist of interconnected aggregates of particles of various sizes which form large pore channels between the aggregates for the transport of the mobile phase. Among the aggregates or clusters there exist small pores for separations. The small particles are formed from tightly packed extremely small particles ca 100-300 nanometers.

The materials made in accordance with these patents have a disadvantage in that the micropores within or between these particles physically trap the sample molecules and degrade the separation. Although these patents claim that there are no interstitial spaces in the monolithic media as in the packed bed with beads, the large channels between the aggregates and interconnected particles actually cause the same problem as the interstitial spaces between the beads in conventional packed columns with beads. The large channels formed from various size of aggregates or clusters are inhomogeneous and provide random interstitial spaces, even with narrow particle size distribution. Because of the random interstitial spaces the column efficiency is poor.

U.S. Pat. Nos. 5,334,310, 5,453,185 and 5,728,457 disclose the preparation of the separation media inside a column with cross section area from square micrometers to square meters. The processes disclosed in these patents have some disadvantages. Some of the disadvantages were disclosed by the inventors named in those patents in 1997 in Chemistry of Materials, 1997, 9, 1898.

One significant disadvantage is that larger diameter (26 mm I.D.) columns prepared from the above patented process have a pore size distribution is too irregular to be effective in chromatography separation. The irregular pore size distribution is caused by the detrimental effect of polymerization exotherm, the heat isolating effect of the polymer, the inability of heat transfer, auto accelerated decomposition of the initiator and concomitant rapid release of nitrogen by using azobisisobutyronitrile as initiator in a mold with 26 mm diameter. It has been found that the temperature increase and differential across the column created by the polymerization exotherm and heat transfer difficulties results in accelerated polymerization in large diameter molds such as for example molds having a diameter of more than 15 mm and in a temperature gradient between the center of the column and the exterior wall of the column which results in inhomogeneous pore structure. It was suggested in this article that the problem might be reduced by slow addition of polymerization mixture. This helps to solve the problem partly but does not solve the problem completely. There is still a temperature gradient for the larger diameter columns, which result in in-homogeneity of the pore size distribution.

This problem was also verified by theoretical calculations in the publication of *Analytical Chemistry*, 2000, 72, 5693. This author proposes a modular approach by stacking thin cylinders to construct large diameter columns for radial flow chromatography. However, sealing between the discs to form a continuous plug is difficult and time consuming.

U.S. Pat. Nos. 5,334,310, 5,453,185 and 5,728,457 disclose the material of weak anion exchange and reversed phase columns. The weak anion exchanger prepared had low resolution, low capacity, low rigidity, slow separation and very poor reproducibility. The reversed phase media has very little capacity, noh-ideal resolution, and very poor reproducibility. They can not be used in mobile phase with high water content such as less than 8% acetonitrile in water due to wall channeling effect resulting from shrinkage of the very hydrophobic media in this very polar mobile phase. This media is also compressed during separation and result in excess void volume in the head of the column. The above patents provide little guidance on how to prepare a weak cation exchanger, strong cation exchanger, strong anion exchanger, normal phase media and hydrophobic interaction media. These media based on membrane, beads or gels are known. However, the preparation are done by off-line and can not be used for in situ preparation of monolithic columns. The monolithic membrane prepared according to U.S. Pat. Nos. 2,889,632, 4,923,610 and 4,952,349 has low capacity and resolution.

SUMMARY OF THE INVENTION

Accordingly, it is an object of the invention to provide an improved separating system having synergistic relationships with a polymer having separation-effective openings.

It is a further object of the invention to provide an improved chromatographic column.

It is a still further object of the invention to provide an improved apparatus for making a chromatographic column.

It is a further object of the invention to provide an improved method for forming chromatographic columns.

It is a still further object of the invention to provide an improved permeable monolithic medium.

It is a still further object of the invention to provide a permeable monolithic column with improved resolution.

It is a still further object of the invention to provide a permeable monolithic column with improved capacity.

It is a still further object of the invention to provide a column with improved flow rate.

It is a still further object of the invention to provide a column with reduced tendency to swell when used with aqueous solvent.

It is a still further object of the invention to provide a column with improved reproducibility.

It is a still further object of the invention to provide an improved technique for the formation of permeable monolithic columns with controlled pore size selected for the purpose of improving capacity or resolution or flow rate.

It is a still further object of the invention to provide a method of preparing large diameter columns for preparative separations.

It is a still further object of the invention to provide a method of preparing polymeric materials including permeable polymer support using irradiation methods.

It is a still further object of the invention to provide an improved weak anion exchange column.

It is a still further object of the invention to provide an improved reverse phase column.

It is a still further object of the invention to provide a high performance strong anion exchange column.

It is a still further object of the invention to provide a high performance weak cation exchange column.

It is a still further object of the invention to provide a high performance strong cation exchange column.

It is a still further object of the invention to provide a high performance normal phase column.

It is a still further object of the invention to provide a method of avoiding a reduction in the quality of a separating medium caused by shrinkage during polymerization or swelling of the medium during washing or during separation.

It is a still further object of the invention to provide a chromatographic system in which an array of columns, in which the columns are very close in characteristics, are operated together.

It is a still further object of the invention to provide a novel process for making monolithic permeable solid support for applications in chromatography including liquid, gas and supercritical fluid chromatography, electrochromatography, catalytic reactor, filtration or others requiring permeable polymer supports or solid permeable polymer holders adjacent or positioned at least partly horizontally from a sample.

It is a further object of the invention to provide a novel high resolution media and novel method of obtaining it.

It is a further object of the invention to provide an improved permeable solid support with homogeneous separation-effective opening size distribution resulting from more homogeneous size and shape of the interconnected aggregated particles.

It is a further object of the invention to provide an improved permeable solid support with less or no micropore.

It is a further object of the invention to provide an improved permeable solid support with no voids on the wall of the polymeric support.

It is a further object of the invention to provide an method for improving the capacity of monolithic chromatography media.

It is a still further object of the invention to provide a permeable monolithic column with improved resolution.

It is a still further object of the invention to provide an improved technique for the formation of permeable monolithic columns with controlled size separation-effective openings selected for the purpose of improving capacity or resolution or flow rate.

It is a still further object of the invention to provide a method of preparing large diameter columns for preparative separations.

It is a still further object of the invention to provide a high performance catalytic reactor.

It is a still further object of the invention to provide a high performance solid phase extraction bed.

It is a still further object of the invention to provide an improved permeable monolithic medium with covalently bonded particles having a controlled minute thoroughly convoluted surface configuration but with few or no micropores.

It is still a further object of the invention to provide a monolithic chromatographic bed with negligible nonuniformities due to thermal effects during polymerization reaction.

It is a still further object of the invention to provide a novel method for controlling polymerization in a chromatographic column with reliance on conduction of heat into the column.

It is still a further object of the invention to control the rate of polymerization, and resulting thermal gradients, by means of controlled radiation impinging on the bed.

It is still a further object of the invention to control polymerization with a relatively safe radiation source such as those providing medium energy x-ray (e.g. below 200 kEV), UV or visible radiation.

It is a still further object of the invention to provide a permeable, high capacity, column with few or no micropores.

It is a still further object of the invention to provide a method of preparing columns with small diameters from nanometers to millimeters.

It is a still further object of the invention to provide a method of preparing chromatographically uniform columns with medium diameters up to 100 mm and large diameter columns up to 1000 mm.

In accordance with the above and further objects of the invention, a polymerization mixture is polymerized in place with a porogen or solvent to form a polymer plug that has separation effective openings. In this specification, "separation-effective openings" means pores or channels or other openings that play a role in separation processes such as for example chromatography. Pores generally means openings in the particles that are substantially round and may be through pores passing through particles (through pores) or openings into the particles or in some cases, openings into or through aggregates of particles. By being substantially round in cross-section, it is meant that the pores are not perfect circles and for example may be bounded by sectors of imperfect spheres with the pores being the open spaces between the adjacent spherical surfaces.

Some other terms are defined below as they are used in this specification. Separation factors includes those factors that effect retention and capacity or other factors that play a role in separation processes. The term "macroporous" in this specification is given its usual meaning in referring to monolithic materials in separation systems. Its usual meaning refers to pores or other voids between globules of particles, which pores or other voids have a diameter of over 50 nm. regardless of the length of an opening, rather than its literal connotation that would limit the openings to pores with a substantially circular cross section and no cross sectional dimension substantially longer than the other. The term "permeable" in this specification shall be interpreted in the same manner as "macroporous" with reference to monolithic materials in the separation arts but is used in preference to the term "macroporous" to distinguish materials having channels and other openings from those containing pores to avoid confusion with the literal meaning of the term "macroporous". In this specification the term "permeable non-porous" describes media having openings such as channels or the like but not containing pores as defined above.

In one embodiment of this invention, shrinkage during polymerization is compensated for and In another embodiment of this invention, swelling after polymerization, which might otherwise later result in shrinkage is avoided. Shrinkage results in enlarged voids on the polymer surface and may result in a lack of homogeneity of pore size distribution inside the polymer. The voids are believed to be created by decreased volume of orderly structured polymer compared to the volume of monomers prior to polymerization when created during polymerization. The voids are mostly located in between the column wall and polymer due to the difference in surface free energy. The voids are probably occupied by the nitrogen gas generated by azobisisobutyronitrile (AIBN), which is a common initiator for the polymerization.

In a first embodiment, the compensation for shrinkage is accomplished by applying sufficient pressure during polymerization to create uniformity in the distribution of separation-effective openings and to avoid wall effect voids. This pressure has been found to also control particle size and the nature and shape of the openings in the plug to some extent. Maintaining the column at atmospheric pressure during polymerization to accommodate shrinkage does reliably prevent the formation of voids. Generally 250 psi pressure is used for convenience but higher and lower pressures have been used successfully. The voids are removed when the plug stops shrinking when put under even modest amounts of pressure. In a second embodiment, shrinkage that otherwise would occur after polymerization is avoided. For example, some plugs tend to expand when exposed to some solutions such as organic solvent and then shrink later such as during a separating run in aqueous mobile phase, causing voids. In these embodiments, shrinkage is prevented by holding the column from shrinkage when exposed to the solutions. The application of pressure is one method of preventing shrinkage during exposure to the aqueous solutions. Other methods for compensated for shrinking and/or swelling, for reducing shrinking or for avoiding shrinking are also used as described in greater detail below. It is believed that the externally applied pressure overcomes uneven forces internal to the reacting polymerization mixture and between the polymerization mixture and internal wall of the column to maintain homogeneous separation effective factors, separation-effective opening size and distribution and uniform continuous contact of the polymer to the internal wall of the column.

Surprisingly, some types of polymer plugs contain no pores if they are subject to pressure during polymerization to compensate for shrinking or in the case of some reversed phase columns to compensate for shrinkage when exposed to hydrophillic solutions such as for example in the aqueous mobile phase Instead, they contain solid particles ca 2 micrometers in diameter, covalently bonded together with relatively large flow channels between them (separation-effective openings). The surprising thing is that, although these particles have no pores, the chromatographic capacity of the plug is high. This is believed to happen because of the unexpected formation of ca 50-200 nm deep and wide grooves or corrugations and other odd surface features. A typical particle resembles a telescopic view of a very small asteroid.

The pressure applied during polymerization is selected in accordance with the desired result and may be, for example, a linearly increasing pressure, a constant pressure or a step pressure gradient. In one embodiment, separation-effective opening size is controlled by selecting the type and proportion of porogen that generates the pores during polymerization and the porogen that must be washed out of the plug after polymerization. This proportion is selected by trial runs to obtain the desired characteristic. The total amount of porogen is also selected.

In another embodiment, some plugs tends to expand when exposed to some solutions such as organic washing solutions and then shrinks later such as during a separating run in the aqueous mobile phase, creating voids between column wall and polymer support and variations in separation-effective opening size distribution. For example, some reverse phase plugs with separation-effective openings may shrink when polymerized others may not, and after polymerization, some of the plugs that did not shrink during polymerization and some that did may shrink if exposed to water or some other polar solutions. In this case, the compensation for this shrinkage is the compression with a piston during polymerization and/or compression after polymerization during conditions that would normally cause shrinking equal or more than the shrinkage that could happen during the separation run to force reordering or repositioning or to compensate for the shrinking. In either case where shrinkage is compensated for with pressure or where shrinkage is prevented to avoid causing voids, non-fluidic pressure such as with a piston is preferred rather than pressure with fluid. The word "pressure" in this specification excludes and differentiates from the term "compression" if the word "compression" is used to indicate the application of salt solutions to gel monoliths to open the pores of such gel monoliths. Another way of solving this problem is to introduce hydrophilicity to the reversed phase media to result in swelling and prevent the shrikage of the polymer in a highly hydrophilic environment during the separation run.

More specifically, a polymerization mixture is applied to a column in the preferred embodiment or to some other suitable mold and polymerization is initiated within the column or mold. The column of mold is sufficiently sealed: (1) to avoid unplanned loss by evaporation if polymerization is in an oven; or (2) to avoid contamination or dilution if polymerization is in a water bath. During polymerization, pressure is applied to the polymerization solution. Preferably the pressure is maintained at a level above atmospheric pressure to prevent the formation of voids by shrinkage until polymerization has resulted in a solid plug of separating medium or polymerization is completed. The inner surface of the column or mold with which the polymerization solution is in contact during polymerization may be non-reactive or may be treated to increase adhesion to the surface of the plug.

The polymerization mixture in some embodiments includes: (1) selected monomers; (2) for some types of columns, an additive; (3) an initiator or catalyst; and (4) a porogen or porogens to form separation-effective openings. In some embodiments function groups can be added before or after polymerization. The porogen, initiator, functional group to be added, additives, and reaction conditions and the monomer and/or polymer are selected for a specific type of column such as reverse phase, weak cation, strong cation, weak anion, strong anion columns, affinity support, normal phase, solid phase extraction and catalytic bed. The selection of components of the polymerization mixture is made to provide the desired quality of column.

A chromatographic column in accordance with this invention preferably includes a casing having internal walls to receive a permeable monolithic polymeric plug in which the separation-effective openings or surface features are of a controlled size formed in the polymer by a porogen in the polymerization mixture and are controlled in size by pressure during polymerization. This plug serves as a support for a sample in chromatographic columns. The permeable monolithic polymeric plug has smooth walls with no visible discontinuity in the plug wall and substantially no discontinuity or opening within the plug. Discontinuity in this specification means a raised portion or opening or depression or other change from the normal smoothness or pattern sufficient in size to be visible with the unaided eye. In this specification, the term "size-compensated polymers" or "size-compensated polymeric" means monolithic polymeric permeable material having separation-effective openings in which discontinuities lack of homogeneity in the separation-effective openings have been prevented by the methods referred to in this specification such as for example applying pressure during polymerization or after polymerization during exposure to polar solutions in the case of some types of columns or by using a column that is prevented from further shrinkage in the presence of an aqueous solution by the application of pressure in the presence of the aqueous solution either during washing with an aqueous solution or during use in a separation operation using an aqueous solution.

One embodiment of column is made using a temperature controlled reaction chamber adapted to contain a polymerization mixture during polymerization and means for applying pressure to said polymerization mixture in said temperature controlled reaction chamber. The polymerization mixture comprises at least a polymer forming material and a porogen.

In one embodiment, the pressure is applied by a movable member having a smooth surface in contact with the polymerization mixture under external fluid or mechanical pressure, although pressure can be applied directly to the polymerization mixture with gas such as nitrogen gas or with a liquid under pressure.

An embodiment of reversed phase media have been formed with different hydrophobicity, and hydrophilicity from the prior art. The reversed phase media include polystyrenes, polymethacrylates and their combinations. These media are prepared by direct polymerization of monomers containing desired functionalities including phenyl, C4, C8, C12, C18 and hydroxyl groups or other combination of hydrophobic and hydrophilic groups to have different selectivity and wettability in aqueous mobile phase. The polymerization conditions and porogens are investigated and selected to give the high resolution separation of large molecules, in particular, the proteins, peptides, oligonucleotides and synthetic homopolymers. In one embodiment a reversed phase media is based on poly(styrene-co-divinylbenzene). In another embodiment of this patent, a reversed phase media is based on poly(stearyl methacrylate-co-divinylbenzene). In another embodiment, a reversed phase media is based on poly(butyl methacryalate-co-ethylene glycol dimethacrylate).

A reverse phase plug with exceptional characteristics is principally formed of copolymers of crosslinkers including divinylbenzene (DVB), and ethylene glycol dimethacrylate and monomers including styrene (ST) or methacrylates (MA) containing different carbon chain length. Generally, the best results are when the crosslinkers are greater than 40 percent by weight Preferably the ratio of divinylbenzene and styrene is a value of divinylbenzene in a range between 7 to 1 and 9 to 1 and preferably 4 to 1 by weight, but may instead be 64 DVB or 40 percent styrene and 72 percent by weight DVB or 1 g divinylbenzene, 1 g styrene. The column may also be in the range of ratios between 17 to 3 and 19 to 1 and preferably 9 parts divinylbenzene to 1 part styrene. Monomers with hydrophilic functional groups can be added to reduce shrinkage of the polymeric medium in aqueous mobile phase to prevent the wall effect during separations. The content of DVB in total monomers is preferably from 40% to 100%. In one preferred embodiment, the content of DVB is 80% (which is the highest commercially available) to improve the loading capacity of the column. The plug may also include methacrylates with hydrophobic surface groups or instead of being a vinyl compound including urea formaldehyde or silica.

Ion exchange plugs are formed principally of methacrylate polymers. A weak anion exchange plug is principally formed of polymers of glycidyl methacrylate (GMA) and of ethylene glycol dimethacrylate (EDMA). A strong anion exchanger plug is principally polymers of glycidyl methacrylate, 2-(acryloyloxyethyl) trimethylammonium methyl sulfate (ATMS), ethylene glycol dimethacrylate. The polymerization mixture may also include 1, 4-butanediol, propanol and AIBN. A weak cation exchanger plug is formed principally of glycidyl methacrylate, acrylic acid (M) and ethylene glycol dimethacrylate. A strong cation exchanger plug is formed principally of glycidyl methacrylate, 2-Acrylamido-2-methyl-1-propanesulfonic acid (AMPS) and ethylene glycol dimethacrylate. In all these ion exchangers, functional groups can be added before or after the plug is formed. The content of EDMA in total monomers is preferably from 40% to 80%.

An increase of the content of crosslinker, such as EDMA, increases the rigidity of the column by reducing the swelling of the media in aqueous phase. Each of the polymerization mixtures is modified under the pressurized polymerization to obtain high flow rate and high resolution at both high and low flow velocity. The coupling of copolymerization of the monomers containing desired functional groups for interaction and the controlled modification of other functional monomers to contain the desired interactive functional groups increases the capacity of the column while improving the rigidity of the separation media. This controlled modification may also improve the hydrophilicity of the columns in general by covering the potential hydrophobic surface area with hydrophilic functional groups. The modification conditions are chosen to not only provide the higher capacity and higher hydrophilicity of the media but also to prevent the swelling of polymer matrix in aqueous solution, which happens in other highly hydrophilic polymer matrices including both beads and monolith.

The polymer plugs may be formed in a column of any size or shape including conventional liquid chromatographic columns that may be circular cylinders, or coiled, bent or straight capillary tubes, or microchips or having any dimension or geometry. The sample or mixture to be separated into its components is injected into the column and the liquid phase is moved through the column to separate the sample into its components. The components may be detected and/or collected in a fraction collector and/or inserted into another device such as a gas chromatograph or mass spectrometer. In one embodiment, a plurality of columns is connected in parallel in a chromatographic system that includes a pumping system, solvent system and detecting system. The columns are permeable polymeric columns with high reproducibility so as to enable them to work together for related separations. In one embodiment, chromatographic discs or plugs having diameters much greater than 25 mm are produced.

In one embodiment, the reaction is controlled by independent means such as for example electromagnetic radiation such as for example UV-vis, X-ray, or γ-ray instead of or in addition to reliance only on time, temperature of a water bath and the reactants in the polymerization mixture. In one form of this embodiment, heat may be added from a heat source or removed by cooling means in contact with a significantly large portion of coolant of the thermal mass and in the reactor under the control of feedback to maintain the temperature of the reaction mass in the desired temperature range or to vary it during the reaction if desired. In another form, variable intensity or variable wavelength X-rays may be used to control the polymerization rates of the mixing reactions at a rate such that the exotherm is under control. X-ray radiation penetrates the column to impart energy throughout the column or at a selected location to increase of decrease polymerization rates. This may be done by irradiating the monomer sufficiently to disassociate its double bonds to make monomers free radicals and thus increase their reactivity. Another way is to use an initiator sensitive to the radiation that is activated by the radiation in the temperature region to be used for the reaction mass. The initiator is chosen to have an activation time and temperature considerably less than that of the monomers alone. Because the initiator forms free radicals only upon radiation of sufficient intensity, the radiation may be used to control the polymerization reaction independently of the other factors. Another way is to use the radiation sensitizers or scintillators in combine with photo initiators to initiate the polymerizations. The radiation sensitizers such as x-ray scintillators transfer the energy of radiations to photoinitiators by luminescence of the photos at the desired wavelength after absorbing the radiation energy transferred through the solvents. The wavelength of the luminescence should be the same as the absorption wavelength of the photoinitiator.

Polymerization using irradiation such as x-ray is used for preparing monolithic materials with cross sections from micrometers to meters. X-rays can penetrate the materials in depth. Both organic and inorganic polymers can be prepared using x-ray or γ-ray. High energy x-ray and γ-ray can travel the materials in high depth. Low energy to medium x-ray penetrates the materials in less depth resulting in a longer polymerization time but is safer to use. In one embodiment, a lower energy x-ray is used to initiate the polymerizations using the combination of x-ray scintillator and photo initiators. We have discovered that non-thermal (photoinitiation) control of polymerization times from less than 12 hours to more than one week provides satisfactory chromatographic columns. Thermal polymerization of columns usually suffers from runaway exothermic reaction and extreme temperature gradients with columns over 20 mm in diameter. This causes ununiformities which degrade chromatographic properties. The slower, controlled, polymerization rate available with x- or γ-rays, or even UV causes a slower polymerization with tolerable rates of exotherm while still maintaining reasonable rates of polymerization. Thermal gradients to exotherm maybe made small enough to not degrade the properties of columns over 1 meter in diameter.

Excessive rates of exotherm and resulting process (polymerization) temperature and temperature gradient may be prevented with choice of a stabilizing additive. This stabilizing additive should have properties such that the reaction can proceed freely up to rate at which the desired polymer is formed, but not at a higher rate producing too high a temperature. For example, with peroxide initiators Disterylhiodipropionate (DSTDP) quenches the hydroxyl radical which results from a side reaction, which later would go on to produce the further heat per event compared to the main reaction. Another approach is to use a stabilizer for the main reaction. This stabilizer is selected for limited solubility in the primary solvents or activity at the reaction temperature and more solubility above the reaction temperature. Under analogous conditions a stabilizer, preferentially soluble in the porogen and having a temperature dependent of solubility or activity may be used.

It is desirable to scale up the size of the column to have higher volume of media is highly desired in preparative chromatography and catalytic reactors. In one embodiment of the invention, the large diameter column is prepared by two staged polymerization inside the column. First, multiple thin cylindrical columns with the diameter smaller than that of the targeted column are prepared in a mold under pressure or without pressure. The thin columns are placed inside a large column filled with the same polymerization solution as used in formation of the thin columns. The thickness in one side of the thin column should not exceed the 8 mm which is the known maximum to prevent the formation of temperature gradient due to the difficulty in heat dissipation during exothermic polymerization. The temperature gradient results in vary inhomogeneous pore size distribution which is detrimental to chromatography use.

In making size-compensated polymers for use in separation systems, the characteristics for a given type of separation can be tailored with a given polymer to the application, by altering the amount of pressure applied during polymerization or and in the case of some polymers such as used in forming reverse phase separation media applying pressure when used or when otherwise brought into contact with a polar solvent such as an aqueous solvent or washing fluid. After the nature of the polymer itself has been selected for a class of applications, columns can be made and tested. Based on the tests, the characteristics can be altered in some columns by applying pressure. It is believed that the application of pressure in some columns increases the uniformity of particle size and either because of the change in particle size of for other reasons, the size distribution and uniformity of separation effective openings throughout the polymer is increased. The increase in homogeniety of the particle size and pore size improves resolution. An increase in pressure generally improves capacity and resolution and the pressure-time gradient. It is believed that in some columns micropores are greatly reduced or eliminated thus reducing zone spreading by the application of pressure during polymerization and/ or during use or washing of the polymer with polar solutions.

From the above description it can be understood that the novel monolithic solid support of this invention has several advantages, such as for example: (1) it provides chromatograms in a manner superior to the prior art; (2) it can be made simply and inexpensively; (3) it provides higher flow rates for some separations than the prior art separations, thus reducing the time of some separations; (4) it provides high resolution separations for some separation processes at lower pressures than some prior art processes; (5) it provides high resolution with disposable columns by reducing the cost of the columns; (6) it permits column of many different shapes to be easily prepared, such as for example annular columns for annular chromatography and prepared in any dimensions especially small dimensions such as for microchips and capillaries and for mass spectroscopy injectors using monolithic permeable polymeric tips; (7) it separates both small and large molecules rapidly; (8) it can provide a superior separating medium for many processes including among others extraction, chromatography, electrophoresis, supercritical fluid chromatography and solid support for catalysis, TLC and integrated CEC separations or chemical reaction; (9) it can provide better characteristics to certain known permeable monolithic separating media; (10) it provides a novel approach for the preparation of large diameter columns with homogeneous separation-effective opening size distribution; (11) it provides a separation media with no wall effect in highly aqueous mobile phase and with improved column efficiency: (11) it improves separation effective factors; and (12) it reduces the problems of swelling and shrinking in reverse phase columns.

BRIEF DESCRIPTION OF THE DRAWINGS

The above noted and other features of the invention will be better understood from the following detailed description, when considered with reference to the accompanying drawings in which:

FIG. 3 is an assembly of another fixture for applying pressure to a stainless steel column during polymerization;

FIG. 4 is an assembly of still another fixture for applying pressure to a glass column during polymerization;

DETAILED DESCRIPTION

Figure 1:
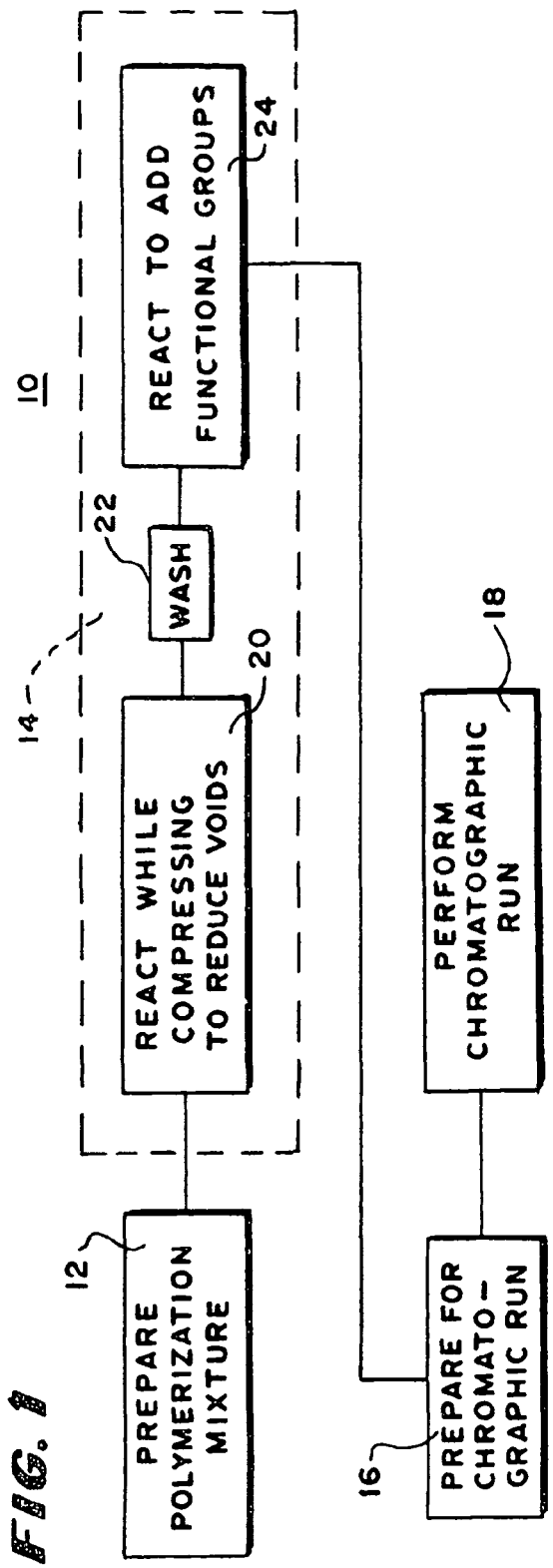
FIG. 1 is a schematic diagram of one embodiment of a process for making a chromatographic column in accordance with an embodiment of the invention.

Broadly, a polymerizable mixture is placed in a container with a porogen or solvent and polymerized to form a plug having separation-effective openings for use in a separation system such as for example a chromatographic column. Advantageously, the polymerization is done in a container in which the plug is to be used such as a chromatographic column or extraction chamber or the like. In one embodiment of the invention, the mixture is polymerized while compensating for the effect of shrinkage during poly merization to form a size compensated polymeric plug. In other embodiments shrinkage is avoided by applying pressure to materials that tend to swell in the presence of water to form another embodiment of size compensated polymeric plug. In still other embodiments separation-effective opening size and distribution is controlled by pressure and/or by selection of the ingredients of the polymerization mixture and/or by processes using external influences such as electromagnetic radiation. Shrinking is compensated for or avoided because it may causes enlarged voids adjacent to the wall of the container and have a deleterious effect on pore size distribution within the column.

In a preferred embodiment, the compensation is accomplished by applying pressure during polymerization to at least maintain the integrity of the material having separation-effective openings as it shrinks during polymerization. Maintaining the column at atmospheric pressure to accommodate shrinkage may not prevent the formation of voids in every case and may provide poor reproducibility. The polymers, monomers, initiators and porogens have been selected to improve the characteristics of the column and may be used with the embodiments of polymerization under pressure during polymerization or with other processes. In another embodiment, pressure is applied to the plug after it has been formed and after or during swelling caused by other reactions such as washing with an aqueous solution after polymerization in the case of some reverse phase plugs. The surface of the column or mold with which the polymerization solution is in contact during polymerization may be non-reactive or may be treated to increase adhesion.

In one embodiment, the polymerization mixture includes at least one vinyl compound and a porogen. An initiator is included in the polymerization mixture or an initiation process is applied to a vinyl monomer and a porogen to form a monolithic plug for a chromatographic column or other device using a polymeric plug for separation. Generally the polymerization mixture includes, in addition to the vinyl monomer, a vinyl polymer, or mixture of monomers and polymers, an initiator and a porogen. However, other approaches to polymerization without incorporating an initiator in the polymerization mixture are known in the art and can be used, such as radiation to form polymers. Moreover, some of the aspects of this invention may be applied to monomers and polymers in a polymerization reaction other than vinyl groups such as for example urea formaldehyde or silica to form urea formaldehyde or silica plugs.

A chromatographic column formed by these processes includes a support having internal walls to receive a permeable monolithic polymeric plug having separation-effective openings of a preselected size distribution formed during polymerization and controlled in size partly by pressure during polymerization and partly by selection of the components and proportions of the components of the polymerization mixture. For example, separation-effective opening size is controlled by the amount and type of porogen in the polymerization mixture in proportion to the amount of some of the other ingredients. The pressures may be selected in a range of slightly above atmospheric pressure to a value within the strength of the walls of the column. The permeable monolithic polymeric plug has smooth walls and substantially no micropores within the plug. The plugs may have surface functional groups. For example, hydrophobic surface groups such as phenolic groups may be added to decrease swelling with aqueous based solvents in reverse phase plugs but capacity may also be decreased in this case. Similarly, hydrophillic surface groups may be added to increase capacity in reverse phase plugs.

One embodiment of permeable, monolithic, polymeric plug that is free of micropores or channeling openings in the walls over is formed principally of vinyl polymers although many other polymers may be used in practicing the invention. A weak ion exchange permeable monolithic polymeric plug is principally formed of polymers of methacrylate such as glycidyl methacrylate and ethylene dimethacrylate in the ratios by weight of a value in the range between 2.5 and 3.5 to a value between 1.8 and 2.2 and preferably 3 to 2. A reverse phase permeable monolithic polymeric plug with exceptional characteristics is principally formed of polymers of divinylbenzene, and of styrene. Preferably the ratio of divinylbenzene and styrene is approximately in a range of a value between 3.5 and 4.5 to a value between 0.8 and 1.2 and preferably 4 to 1 by weight, but may instead be 64 DVB (divinylbenzene) or 40 percent styrene and 72 percent by weight DVB or in the ratio of divinylbenzene to styrene in the range of a ratio of 2 to 3 and a ratio of 3 to 2 or preferably 1 to 1. The column may also be in the ratio of divinylbenzene to styrene in a range of the ratio of 8 to 1 and 10 to 1 and preferably 9 to 1. One hundred percent DVB is also preferred.

In FIG. 1 there is shown a block diagram of one embodiment 10 of a method for making chromatographic columns comprising the step 12 of preparing a polymerization mixture, the step 14 of polymerizing the mixture, the step 16 of preparing the column for chromatographic run and the step 18 of performing a chromatographic run. The polymerization mixture used in step 14 of polymerizing a mixture includes a monomer and or polymer capable of polymerization, an initiator or initiation process such as radiation, and a porogen, many of which are known in the art. The step 12 of preparing the chromatographic mixture, the step 14 of polymerizing, the step 16 of preparing for a chromatographic run and the step 18 of performing the chromatographic run all may take different forms. Some of these variations will be described hereinafter.

In the step 14 includes the substeps 20 of reacting the polymerization compound while compressing it to reduce voids, the substep 22 of washing the polymer, and in some embodiments, the step 24 of reacting the polymer to add certain functional groups. While a workable column may be obtained without compressing the polymerization mixture while polymerizing, significant improvements have been obtained by applying this compression. These improvements have been significant enough so as to make the difference between a competitive commercial column and one which would not be competitive in some types of columns and for some applications The voids and inhomogeneous separation-effective openings that are prevented from forming by this compression may result from the inhomogeneous distribution of the empty space created by shrinkage of the polymer during polymerization in a sealed container. The inhomogeneous distribution of the empty space may be due to the differences in surface tension between the column wall surface, polymer surface, nitrogen and porogens. The compression must be sufficient to take up this shrinkage and thus reduce the total volume of the column during polymerization. This process may also affect the separation-effective opening size in the column and can be used in a step by step process to create variations in separation-effective opening size if desired.

The washing step 22 is a conventional step intended to remove porogens and unreacted monomers or other ingredients that may be used for a specific column but are not intended to remain in the column. This step may be followed by reacting in a manner to add functional groups such as the groups described above that are important if the column is intended to separate proteins. In some embodiments, the washing step causes swelling of the plug followed by later shrinkage. Because the shrinkage may cause channeling voids, pressure is applied to the swollen plug in one embodiment to prevent the formation of voids during shrinking.

Figure 2:
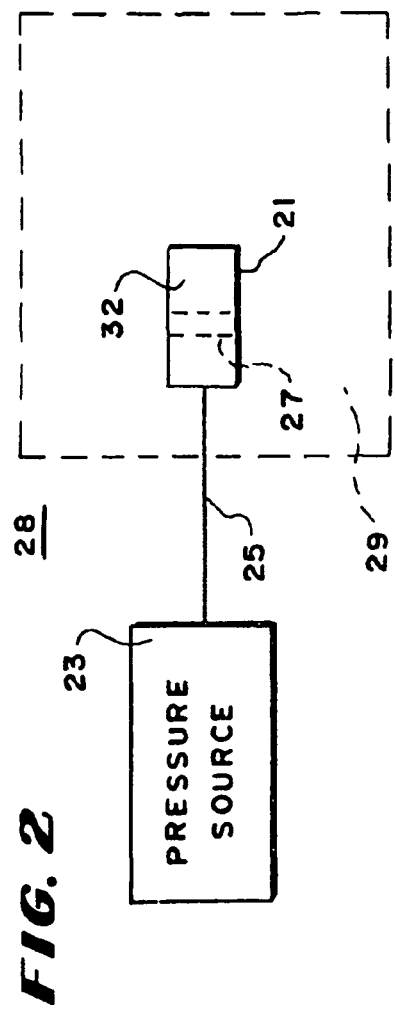
FIG. 2 is an assembly of a fixture for applying pressure to a glass column during polymerization.

In FIG. 2, there is shown a block diagram of a polymerizing apparatus 28 having a pressure source 23, a pressure transfer mechanism 25 for applying pressure to a polymerization mixture 32 compression piston 27 and a confinement vessel 21. In the preferred embodiment, the source of pressure 23 is a regulated source of constant hydraulic pressure but other sources such as a spring or source of air or of an inert gas may be used. Similarly, in the preferred embodiment, the mechanism 25 is a piston with a smooth surface to provide a smooth surface to the polymerized plug that the piston surface has pressed against during polymerization but other sources such as a gas applied directly to the permeable monolithic polymeric plug may be used. In the preferred embodiment, the compression piston 27 moves inwardly into the column department 21 to exert pressure on the polymerization mixture within the compartment 32 during the polymerization reaction. When the polymerization reaction is complete, the porogen can be removed by a solvent pumped through the column. The polymerization occurs in a temperature controlled environment 29, which is the preferred embodiment is a water bath but can be any such temperature control mechanism such as a heated chamber. The materials for this device can be any conventional materials know in the art.

In FIG. 3 there is shown a sectional view of one embodiment of the polymerizing apparatus 28 having a metal column casing 1022, a confinement vessel 88, a transfer mechanism 25, a compression piston 112 and a pressure cap 80. The metal column 1022 is tightly held against the confinement vessel 88 with a seal 1021 between them. Compression of the seal 1021 is provided by a shoulder 1052 in the barrel 122 and wrench flats 1023 of the apparatus, which is attached to the column 1022 with threads 1053, thus providing a leak free connection between the column 1022 and the confinement vessel 88. A transfer mechanism 25 consisting of a compression piston 112, an o-ring 110, a rod 106, a retaining collar 104, another o-ring 100, and a hydraulic piston head 602, all of which are arranged and fitted into the barrel 122 such that the compression piston 112 and o-ring 110 form a tight seal inside the confinement vessel 88. The pressure cap 80 contains a fluid inlet port 33 fitted to the barrel 122, with a gasket 94 between them.

The pressure cap 80 and the barrel 122 are tightly connected, preventing the leakage of pressurized fluid applied through the fluid inlet 33. The transfer mechanism 25 is then positioned as shown, creating a volume in the confinement vessel 88. The square of the ratios of the inside diameter of the barrel 122 at o-ring 100 to inside diameter of confinement vessel 88 provides a pressure multiplication factor. The opposite end of the column 1022 is filled with the polymerization reactants in the column compartment 32, and a containment plug 1024 is fitted in the opening. A containment cap 604 is threaded onto the column 1022, forcing the containment plug to seal the opening. Although the preferred embodiment here shows a tight fitting plug 1024 to provide the sealing, an alternate sealing arrangement, such as an,o-ring, could as easily be used to provide either a face seal or a radial seal. The fluid inlet 33 is connected to a controlled pressure source, such as a controllable fluid pump or regulated bottle of compressed gas.

This description of the preferred embodiment employs a fluid source; either compressed gas or compressed liquid applied through the fluid inlet 33, however the compressive force could as easily be supplied by alternate means; such as, but not limited to a spring pressing on the transfer mechanism 25, weights stacked on the transfer mechanism 25 utilizing gravity to provide the compression, or centripetal force arranged to cause the transfer mechanism 25 to compress the monolithic polymeric column material inside the column compartment 32.

Once assembled, the apparatus 28 is placed in a temperature-controlled environment 27, which is a thermally controlled water bath in the preferred embodiment. Fluid pressure is then applied through the fluid inlet port 33, which is contained by the pressure cap 80, the gasket 94 the hydraulic piston head 602 and the o-ring 100. This applied force causes the hydraulic piston head 602 to move away from the pressure cap 80, and exerts force on the end of the rod 106. This rod 106 communicates the force to the compression piston, applying compressive pressure to the monolithic polymeric column material, preferably at the smooth surface 1101. This smooth surface causes a continuous, uniform surface to be created on the monolithic polymeric material exposed to the analytical fluids in the ultimate application and reduces the adhesion of the monolithic polymeric column material to the compression piston 112.

The containment plug 1024, column 1022, seal 1021 confinement vessel 88, and the compression piston 112 confine the monolithic polymeric material. As the chemical reaction proceeds, the volume of the monolithic polymeric material decreases, and the transfer mechanism 25 moves further into the confinement vessel 88. Air trapped between the o-ring 100 and the o-ring 110 is allowed to escape through an air escape opening 603 in the barrel 122. The compression of the reactant materials in this manner prevents the formation of undesirable voids in the monolithic polymeric material and eliminates wall effects between the monolithic polymeric material, and the column 1022, which would reduce the performance of the column in use.

As the reaction proceeds and the monolithic polymeric material volume reduces, the compression piston moves closer to the column 1022. Near the end of the polymerization, the retaining collar 104 contacts the shoulder 608 in the barrel 122, halting the forward motion of the transfer mechanism 25. Crushing of the newly formed monolithic polymeric material is prevented by this action. At this position, the smooth surface 1101 of the compression piston 112 is approximately even with the end of the column, and the monolithic polymeric material fills the column 1022 without undesired voids in the material or wall effects between the material and the column 1022. Using the wrench flats 1023 and 604, the polymer apparatus 28 is separated from the column 1022 as an assembly. Chromatographic fittings are then installed on both ends.

In FIG. 4 there is shown a sectional view of another embodiment of polymerizing apparatus 28A similar to the embodiment of polymerizing apparatus 28 having a glass column casing 922, a piston head assembly 401, a displacement piston 40 and a containment plug 923. In some analytical chemistry applications, the wetted surfaces must not contain metal components. Although the present discussion of this preferred embodiment refers to a glass column 922 and plastic pieces, any non-metallic material; such as, but not limited to glass, ceramic, or plastic which provides acceptable mechanical properties can be used. Further, the discussion here refers to the pressure applied being provided by a suitable fluid pressure source, alternative means of providing compression; including, but not limited to springs, weights, or mechanical means could as easily be used.

The piston head assembly 401 comprises a piston 76, an o-ring 38 and an intermediate portion 50, assembled and filted into the column 922. A plunger assembly 20 consisting of the displacement piston 40 and an o-ring 64 are assembled and fitted into the hydraulic cylinder portion 21 such that the recess 92 is away from the fluid inlet port 33 in the hydraulic cylinder portion 21. This plunger assembly 30 is pushed fully into the displacement chamber 60.

The hydraulic cylinder portion 21 and plunger assembly 30 are then threaded onto the column 922. Using a suitable tool, the piston assembly 401 is pushed into the hydraulic cylinder portion 21 until the annular shoulder 42 contacts the displacement piston 40, with the reduced diameter neck 48 fitting into the recess 42. The column 922 is filled with the reactant, and the containment plug 923 is inserted into the open end of the column 922. A containment cap 924 is then threaded onto the end of the column 922, tightly holding the containment plug 923 to the column 922. Although this embodiment utilizes a tight fit between the containment plug 923 and the column 922, alternate methods; including, but not limited to an o-ring creating a face or radial seal can as easily be used.

A fluid pressure source is then applied through the fluid inlet port 33. The fluid is contained within the displacement chamber 60 by the hydraulic cylinder portion 21, the displacement piston 40 and the o-ring 64. The assembled components are then placed in a temperature-controlled environment 27. For this embodiment, a thermally controlled water bath was used, but any suitable method of controlling the reaction temperature can be employed.

The application of such fluid pressure causes the displacement piston 40 to move away from the fluid inlet port 33. This movement of the displacement piston 40 applies force to the annular shoulder 42 of the intermediate portion 50, which then applies pressure to the monolithic polymeric material in the column 922 through the piston 76. As the reactant chemicals polymerize, the volume decreases. With the controlled application of pressure to the monolithic polymeric material prevents the formation of undesirable voids within the monolithic polymeric material and the formation of wall effects between the monolithic polymeric material and the wall of the column 922. As the reaction progresses, the piston 76 moves further into the column 922 to displace this reduction in volume. A smooth surface 74 on the piston creates a uniform surface of the monolithic polymeric material to provide a consistent interface to the analytic fluids in its final use, and to prevent the monolithic polymeric material from adhering to the surface of the piston 76.

Near the end of the reaction, the annular shoulder 42 comes in contact with the end of the column 922, preventing any further movement of the intermediate portion 50 into the column 922. This prevents the crushing of the monolithic polymeric material after the voids and wall effects have been eliminated. This annular shoulder 42 also limits the distance that the piston can travel, allowing control the porosity and size of the resultant monolithic polymeric material in the column 922.

After the polymerization is completed, the hydraulic cylinder portion 21 is removed from the column 922, together with the displacement piston 40 and its o-ring 64. The confinement cap 924 and confinement plug 923 are then removed, and finally the piston head assembly 401 is removed. Chromatographic fittings are then installed on both ends.

It is also possible to provide compression on the reactant chemicals by the direct application of compressed gas directly to the reactant chemical's surface. Such a method is considered inferior to the above techniques because the surface of the resultant monolithic polymeric material will not be smooth or even, and may be more porous than the body of the monolithic polymeric material, when particular column formats are chosen. In other column formats the direct application of gas may be more applicable. It may be necessary to cut off the end of the polymer rod to achieve high resolution separation.

Figure 5:
FIG. 5 is a Scanning Electron Microscopy (SEM) picture of the strong cation exchanger polymerized inside a cylinder column under 120 psi hydraulic pressure.

In FIG. 5 there is shown a Scanning Electron Microscopy (SEM) picture of a strong cation exchanger polymerized inside a column casing under 120 psi hydraulic pressure magnified 9,000 times to show globules of particles with no pores but with channels between them having high surface area because of the irregular surface area and to a lesser extent the more stacked-plate like configurations of the globules of particles. The rough surface area of the particles with projections covering their surface area shows signs that may indicate growth by accretion.

Figure 6:
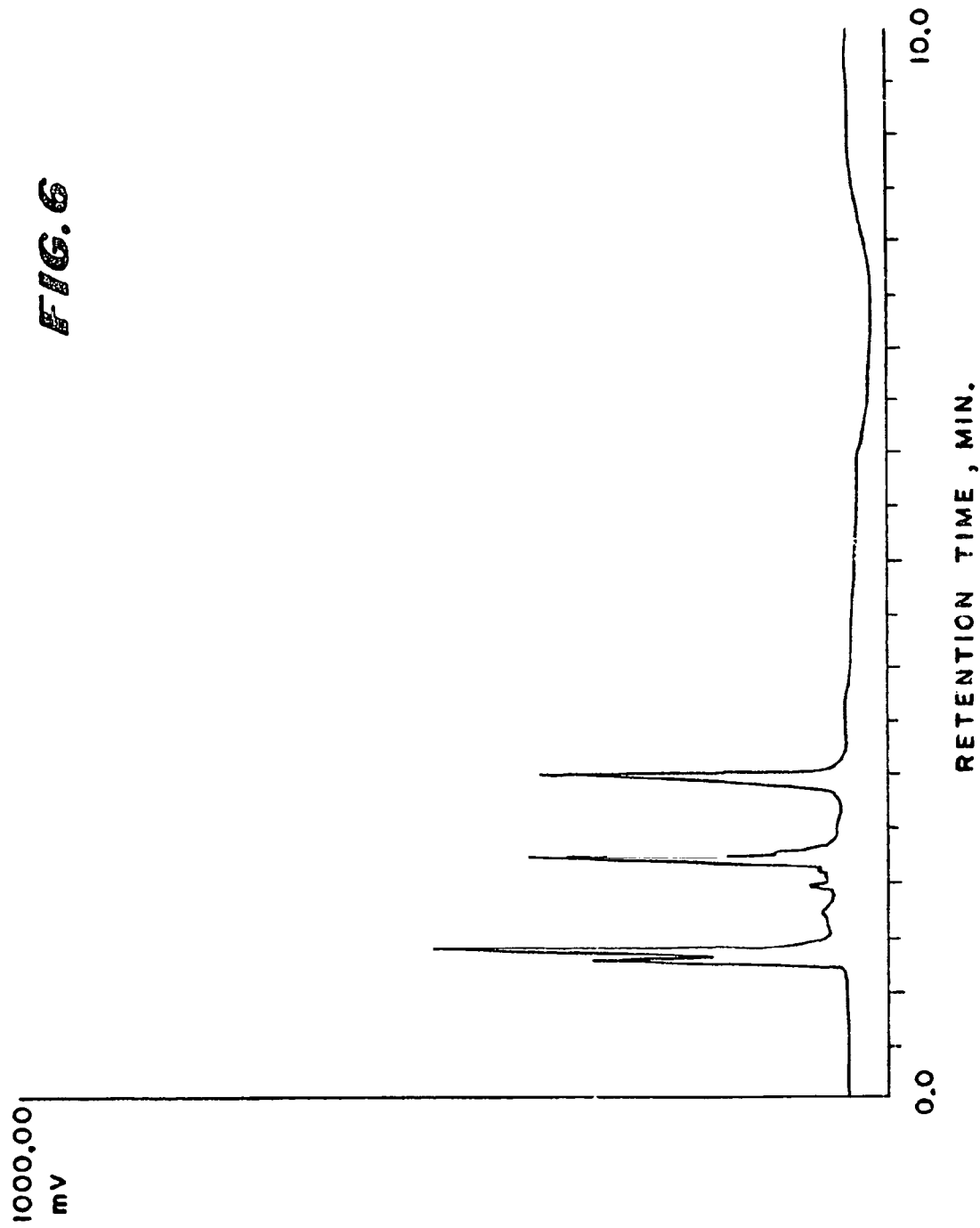
FIG. 6 is a chromatogram showing peaks from a protein sample with a column in which distortions have been avoided by pressure during polymerization.

In FIG. 6, there is shown a chromatogram having peaks from a protein sample separated in a column in which the problems of swelling and shrinking avoided by the application of pressurel. The peaks are distinctive and relatively high with good resolution. This particular chromatogram is for gradient elusion at a flow rate of 3 ml/min on a protein sample of conalbumin, ovalbumin and tripsin inhibitor using a 0.01 MTris buffer of pH 7.6 as one solvent and a 1 M sodium chloride as the other solvent with a gradient of 0 to 50 percent the second solvent in 5 minutes time. The back pressure is 250 pounds per square inch in this column whereas a column without such compensation would be expected to have a higher back pressure for the same gradient.

Figure 7:
FIG. 7 is a photograph showing three columns with the one on the left made with pressure during polymerization and the two on the right polymerized without pressure.

In FIG. 7, there is shown three plugs with the one on the left made with pressure during polymerization and the two on the right polymerized without pressure. FIG. 7 illustrates the discontinuities formed on the surface of columns caused by shrinkage during formation of the column. There are similar discontinuities inside the column in the form of relatively large openings unpredictably spaced. These figures also illustrate that the discontinuities can be removed, resulting in better reproducibility between columns of the same composition and the same size and improved resolution during chromatographic runs.

Figure 8:
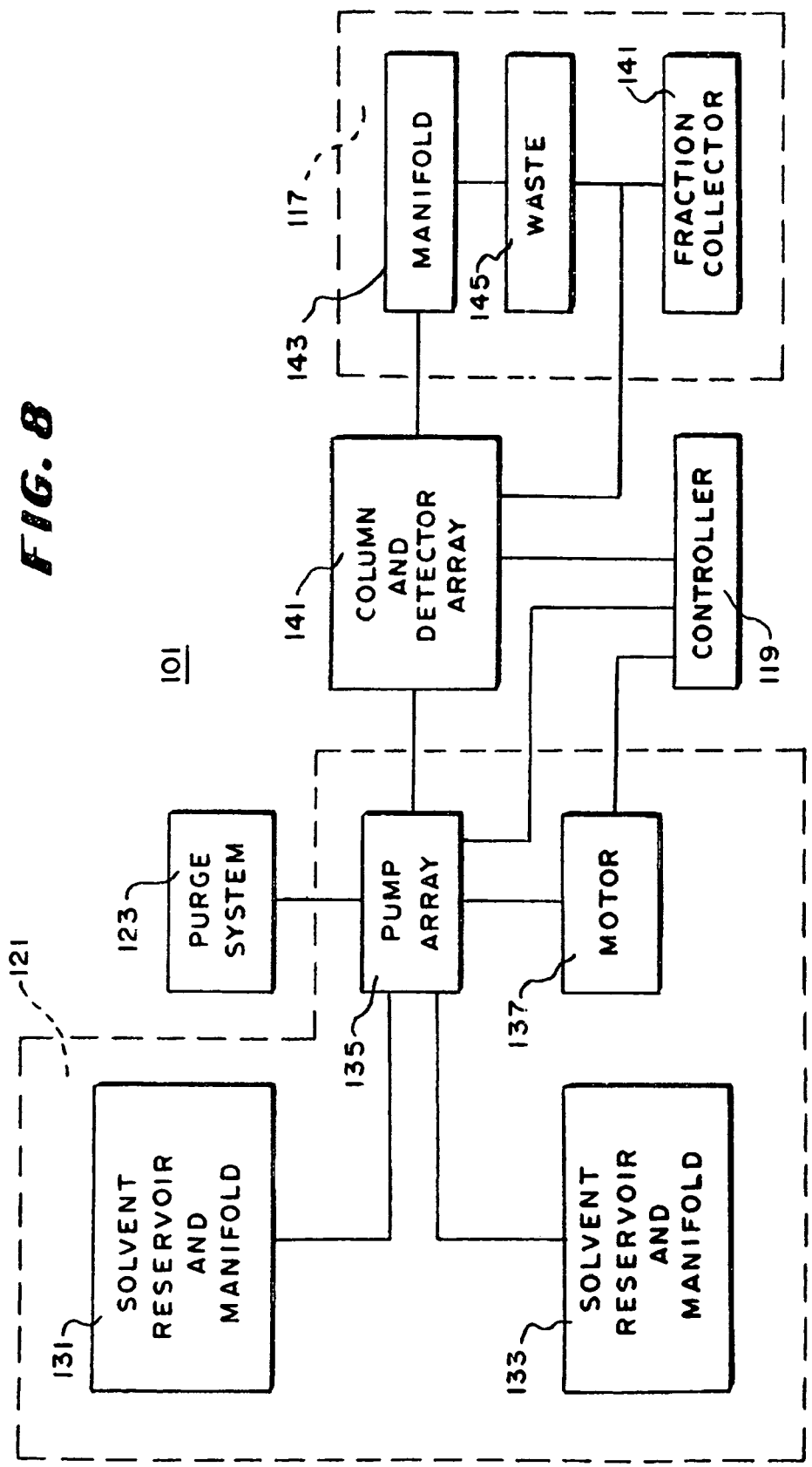
FIG. 8 is a block diagram of a chromatographic system with an array of columns and having reproducible characteristics which are similar to each other in the array.

In FIG. 8, there is shown a block diagram of a preparatory liquid chromatographic system 101 having a pumping system 121, a column and detector array 141, a collector system 117, a controller 119, and a purge system 123. The column and detector array 141 includes a plurality of columns with permeable plugs in them. Preferably the plugs are size-compensated polymeric plugs. The pumping system 121 supplies solvent to the column and detector array 141 under the control of the controller 119. The purge system 123 communicates with a pump array 135 to purge the pumps and the lines between the pumps and the columns between chromatographic runs. The pump array 135 supplies solvent to the column and detector array 141 from which effluent flows into the collector system 117 under the control of the controller 119. The controller 119 receives signals from detectors in the column and detector array 141 indicating bands of solute and activates the fraction collector system 117 accordingly in a manner known in the art. One suitable fraction collector system is the FOXY7 200 fraction collector available from Isco, Inc., 4700 Superior Street, Lincoln, Nebr. 68504.

To supply solvent to the pump array 135, the pumping system 121 includes a plurality of solvent reservoirs and manifolds, a first and second of which are indicated at 131 and 133 respectively, a pump array 135 and a motor 137 which is driven under the control of the controller 119 to operate the array of pumps 135. The controller 119 also controls the valves in the pump array 135 to control the flow of solvent and the formation of gradients as the motor actuates the pistons of the reciprocating pumps in the pump array 135 simultaneously to pump solvent from a plurality of pumps in the array and to draw solvent from the solvent reservoirs and manifolds such as 131 and 133.

While in the preferred embodiment, an array of reciprocating piston pumps are used, any type of pump is suitable whether reciprocating or not and whether piston type or not. A large number of different pumps and pumping principles are known in the art and to persons of ordinary skill in the art and any such known pump or pumping principle may be adaptable to the invention disclosed herein with routine engineering in most cases. While two solvents are disclosed in the embodiment of FIG. 1, only one solvent may be used or more than two solvents.

To process the effluent, the collector system 117 includes a fraction collector 141 to collect solute, a manifold 143 and a waste depository 145 to handle waste from the manifold 143. One or more fraction collectors communicate with a column and detector array 143 to receive the solute from the columns, either with a manifold or not. A manifold may be used to combine solute from more than one column and deposit them together in a single receptacle or each column may deposit solute in its own receptacle or some of the columns each may deposit solute in its own corresponding receptacle and others may combine solute in the same receptacles. The manifold 143 communicates with the column and detector array 141 to channel effluent from each column and deposit it in the waste depository 145.

Because the system of FIG. 8 includes an array of columns each involved in a similar task, reproducibility of the column is particularly important since it is desirable for each column performing a single task to have characteristics as similar to all of the other columns performing that task as possible. Consequently, there is a substantial advantage in any group of columns that are intended to cooperate in the performing of a separation of samples closely related to each other, the permeable polymeric columns of this invention have particular application.

To make a column or other device having a polymeric plug as a separating medium without openings in the side walls or large openings in the body of the plug, one embodiment of polymerization equipment includes a temperature controlled reaction chamber adapted to contain a polymerization mixture during polymerization and means for applying pressure to said polymerization mixture in said temperature controlled reaction chamber. The polymerization mixture comprises a monomer, polymer and a porogen. In a preferred embodiment the means for applying pressure is a means for applying pressure with a movable member. The polymerization mixture comprises includes a cross-linking reagent and a cross-linking monomer. The rigidity, capacity and separation-effective opening distribution are controlled by the amount of cross-linking reagent, monomer, and pressure.

The polymerization takes place in a closed container to avoid loss of solvent in the case or an oven or to avoid dilution or contamination of the mixture with water in the case of a water bath reaction chamber. Pressure is applied during polymerization of some mixtures such as mixtures for ion exchange columns to balance vacuum formed by shrinkage. The polymer plug is washed after polymerization to remove the porogen. In the case of some polymer, the plug may have a tendency to swell during washing or during a chromatographic run if aqueous solutions are applied such as if the plug is a reverse phase plug.

To separate a mixture into its components, a permeable polymeric plug is formed as described above. It may be formed in a column of any size or shape including conventional liquid chromatographic columns that are right regular tubular cylinders, or capillary tubes, or microchips or having any dimension or geometry. A sample is located in juxtaposition with the plug and the components of the sample are separated one from the other as they are moved through the plug.

For example, to separate proteins from a mixture of proteins in a sample by liquid chromatography, a column is formed as a plug and polymerized in place with a porogen. Shrinkage is compensated for before use. The sample is injected into the column and a solvent caused to flow through the column, whereby the sample is separated into its components as it is carried through the plug. In one embodiment, a plurality of samples are separated simultaneously in separate columns with high reproducibility.

One embodiment of chromatographic columns used in separation processes have a chromatographic casing with internal casing walls and have a permeable monolithic polymeric plug in the casing walls. The plug is a polymer having separation-effective openings which may be of a controlled size formed in the polymer by a porogen in the polymerization mixture before polymerization and controlled in size at least partly by pressure during polymerization. The permeable monolithic polymeric plug has smooth walls and substantially no pores within the permeable monolithic polymeric plug. In the preferred embodiment, the plug is formed of vinyl polymers but may be formed of others such as urea formaldehyde or silica. The may include surface groups such as hydrophobic groups to reduce swelling with aqueous solvents or hydrophillic groups to increase capacity.

Some examples of the proportions of the ingredients in polymerization mixtures and the ingredients in different plugs are illustrative. For example, a weak ion exchanger permeable monolithic polymeric plug that is free of channeling openings is formed principally of methacrylate polymer. Advantageously, his permeable monolithic polymeric plug is principally formed of polymers of glycidyl methacrylate and of ethylene dimethacrylate in the ratio by weight in a range of ratios between 1 to 1 and 7 to 3 and preferably 3 to 2.

A strong anion exchanger includes as its principal ingredients glycidyl methacrylate (GMA) and ethylene divinyl methacrylate (EDMA) in the ratio of a value in the range of 0.8 to 1.2 to a value in the range of 2.8 to 3.2 and preferably a ratio of 1 to 3. The polymerization solution in the preferred embodiment includes 0.4 grams GMA, 0.5 grams of 2-(acryloyloxyethyl) trimethylammonium methyl sulfate, 1.2 grams EDMA, 1.5 grams of 1,4-butanediol, 1.35 grams propanol, 0.15 grams water and 0.02 grams AIBN.

A weak cation exchanger included a polymerization solution of methyl methacrylate (MMA), GMA and EDMA in the ratio of a value of MMA in the range of 4.5 to 5.5 to a value of GMA in the range of 0.8 to 1.2 to a value of EDMA in a range of 11 to 13, and preferably a ratio of 5 to 1 to 12. The polymerization solution includes 0.2 grams M, 0.5 grams methyl methacrylate (MMA), 0.1 grams GMA, 1.2 grams EDMA, 2.55 grams dodecanol, 0.45 grams cyclohexanol and 0.02 grams AIBN. After polymerization, this column is hydrolyzed in a 0.25 M sodium chloroacetate in 5 M (molar) sodium hydroxide NaOH at 60° C. for six hours.

Other examples are: (1) glycidyl methacrylate and of ethylene dimethacrylate in a ratio by weight in the range of from 1 to 1 and 2 to 1; or (2) divinylbenzene and styrene in a ratio in the range of 3 to 1 and 9 to 1; or (3) divinylbenzene and styrene in a ratio in the range of 4 to 1 or with the amount divinylbenzene being in the range of 35 percent and 80 percent by weight divinylbenzene and preferably 64 percent by weight divinylbenzene; or (4) divinylbenzene, styrene and porogen are in the ratio of 8 to 2 to 15 respectively; or (5) divinylbenzene, styrene and dodecanol in a proportion within the range of 7 to 9 units of divinylbenzene to 1.5 to 2.5 units of styrene to 13-17 units of dodecanol combined with an initiator, or (6) divinylbenzene, styrene and dodecanol in the range of 8 to 2 to 15 respectively combined with an initiator; or (7) divinylbenzene, styrene dodecanol and toluene in the proportions of 7-9 to 1.5-2.5 to 9-13 to 2.5-3.5 respectively, combined with an initiator; or (8) divinylbenzene, styrene dodecanol and toluene combined in the proportions of of 8 to 2 to 11 to 3 respectively, combined with an initiator; or (8) glycidyl methacrylate, ethylene dimethacrylate, cyclohexanol and dodecanol in the proportions of 0.5-0.7 to 0.3-0.5 to 1-2 to 0.1-2.5, combined with an initiator; or (9) glycidyl methacrylate, ethylene dimethacrylate, cyclohexanol and dodecanol in the proportions of 0.6 to 0.4 to 1.325 to 0.175 respectively.

In general, a process of preparing a monolithic polymer support having separation-effective openings for a targeted application may include the following steps: (1) preparing a polymerization mixture with a selected formula; (2) placing the mixture in a container, sometimes referred to as a column in the embodiments of this inventions, with desired shape and size; (3) sealing the column with pressurizing filtings or non-pressure sealing; (4) polymerizing the polymerization mixture in a heating bath or oven with controlled temperature under selected pressure or without pressure; (5) taking the columns from the heating bath or oven and applying selected or specially designed fittings for the desired function; (6) washing the porogens and soluble materials out of the columns with selected solvent preferably by programmed flow; (7) in some embodiments, pumping a formulated modification solutions to obtain the desired functionality for interaction; (8) performing special modification in a heating bath or oven under controlled conditions; (9) washing the modification solutions out of the columns preferably with a programmed flow; (10) stabilizing, assembling and conditioning the column for its use at desired conditions with high resolution; (11) characterizing the columns with sample separation in the target application; (12) replacing the liquid in the column with selected storage solution. Steps 7 to 9 areas optional or repetitive depending on the functionality of the media to be used. Steps 1 to 5 are modified and repeated in the two or multiple staged polymerization process.

In some of the embodiments of this invention, a polymerization mixture includes single or plurality of: (1) monomers; (2) porogens; (3) initiators or catalysts; and/or (4) additives or fillers (optional). The polymerization mixture may be degassed with helium for more than 15 minutes, or by vacuum, or by combination of both prior to be filled or injected to the column. The goal of this degassing is to get rid of the oxygen inside the mixture. The oxygen can act as an inhibitor or initiator at different situation resulting in some unpredictable behavior of the polymerization, which is detrimental to the resolution and reproducibility of the columns.

The suitable monomers for the above process comprise mono, di and multiple functional monomers known in the art, preferably monomers containing the vinyl or hydroxyl silica functional groups, which might be generated in situ as an intermediate. The typical monovinyl monomers include styrene and its derivatives containing hydroxyl, halogen, amino, sulfonic acid, carboxylic acid, nitro groups and different alkyl chain such as c4, c8, c12 and c18, or their protected format which could be used to generate those functionalities before or after polymerization; and include acrylates, methacrylates, acrylamides, methacrylamides, vinylpyrolidones, vinylacetates, acrylic acids, methacrylic acids, vinyl sulfonic acids, and the derivatives or these groups which could be used to generate these compounds in situ. The mixture of these monomers can be used. Siloxanes with hydroxyl group, vinyl groups, alkyl groups or their derivative and mixture thereof are preferred. The amount of the monofunctional monomers are varied from 2% to 60% of the total monomers in the embodiments of this invention. They vary dramatically depend on the type of media.

The typical di or multifunctional monomers are preferably the di or multiple vinyl-containing monomers with a bridging moiety such as benzene, naphthalene, pyridine, alkyl ethylene glycol or its oligoes. Examples of these polyvinyl compounds are divinylbenzene, divinylnaphthalene, alkylene diacrylates, dimethacrylates, diacrylamides and dimethacrylamide, divinylpiridine, ethylene glycol dimethacrylates and diacrylates, polyethylene glycol dimethacrylates and acrylates, pentaerythritol di-, tri-, or tetramethacrylate and acrylate, trimethylopropane trimethacrylate and acrylate, and the mixture of these compounds. Siloxanes with di, tri and tetrahydroxyl groups, which are often generated in situ are also preferred in this invention. The typical amount of the multifunctional monomers are from 40% to 80% in the embodiments of this invention.

The initiators comprise all the initiators known in the art such as azo compounds, peroxides. Example of the typical intiators are azobisisobutylonitrile, benzoyl peroxide, 2,2'-azobis(isobutyramide)dehydrate, 2,2'-azobis(2-amidinopropane)dihydrochloride. The typical amount of the initiator is from 0.5% to 2% of the total monomers in the embodiments of this invention. When siloxane is used, a catalyst such as an acid is used instead of an initiator. The amount of catalyst is from milimoles to moles per liter of polymerization mixture. Other approaches to polymerization without incorporating an initiator in the polymerization mixture are known in the art and can be used, such as radiation to form polymers.

The porogen is any material or compound which can be removed after polymerization to generate separation-effective opening structures. The typical porogens may be used are organic solvents, water, oligomers, polymers, decomposable or soluble polymers. Some example of the organic solvents are alcohols, esters, ethers, aliphatic and aromatic hydrocarbons, ketones, di, tri, tetraethylene glycols, butane diols, glycerols or the combination of these solvents. The choice of porogens depends on the separation-effective opening size and separation-effective opening distribution needed.

In some embodiments, a single or a combination of porogenic solvents which are mixable with the monomers and initiators to form a homogeneous solution but have poor solvating power to the polymers formed is chosen. The polymerization usually starts from the initiator. The formation of oligomers is followed by crosslinking forming crosslinked polymer or nuclei, and the continuous growth of the polymer or nuclei. These polymer chains and nuclei precipitate out of the solution at the size allowed by the solvating power of the porogenic solvents. These polymer chains and nucleis are suspended in the solution first and form small particle through collision and crosslinking. The small particles are swelled by the porogens and monomers, and continue to grow by both polymerization and aggregation with other nucleis or particles. The larger particles aggregate together by collision and held in place by crosslinking. The time and speed of the precipitation of the polymer and nuclei dramatically affect the size of particles, aggregates or clusters and the separation-effective opening size formed among these particles and aggregates as well as the separation-effective opening size distribution.

It has been discovered that the combination of a very poor solvent and a fairly good solvent are usually better to tune the solubility or swellability of the polymer in the solution, which result in desired porosity and separation-effective opening size distribution. The choice of poor solvent is more important since generation of the large separation-effective opening is the most important. After the generation of large separation-effective opening, it is always easier to find a good or fairly good solvent to tune the separation-effective opening size down. It has been discovered that the alcohols or the neutral compounds containing a hydroxyl group or multiple hydroxyl groups are the better choice of the poor solvents for the media made of polystyrenes, polymethacrylates, polyacrylates, polyacrylamides and polymethacrylamides. The solubility or solvation power can be easily tuned to using alcohols of different chain length and number of hydroxyl groups. A good solvent for the polymers can be chosen from many conventional good solvents such as toluene, tetrahydrofuran, acetonitrile, formamide, acetamide, DMSO. They typical amount of the porogens vary from 20% to 80%, more preferably 40% to 60% in the embodiments of this invention.

The additives or fillers used in this invention are those materials which can add a specifically desired feature to the media. One important characteristic of polymers having separation-effective openings is the rigidity of the polymer. Insoluble rigid polymer particles, silica particles, or other inorganic particles can be added into the polymerization mixture to strengthen the polymer having separation-effective openings after the polymerization. Polymers with a very large number or amount of separation-effective openings usually do not have good strength or toughness. They are fragile most of the time. The rigid particles can act as framework for the polymers. In another embodiment, the resolution of the large columns and reduce the problem of heat transfer during the preparation of large diameter columns are reduced by adding very mono-dispersed nonporous particles to the polymerization mixture for. Quite often, a large diameter column is required for high flow preparative chromatography or catalytic bed to allow high flow rate with only low back pressure.

In an embodiment of polymer having separation-effective openings, mono-dispersed large non-porous particles or beads are packed tightly with the pattern of close to dense packing. The polymerization mixture is filled into the interstitial space of the large beads and polymerized in these spaces. The flow pattern and column efficiency are improved by the densely packed monodispersed beads. Materials with a very large number of or amount of separation-effective openings can be prepared in this large diameter columns without fear of collapse of the media with low rigidity since the large monodispersed beads are the supporting materials for the large columns. High flow rate can be achieved owing to the large number or amount of separation-effective openings but robust structure of the polymer.

In another embodiment, the heat dissipation problem is avoided in preparation of the large columns with two or multiple staged polymerization incorporating polymers having separation-effective openings as fillers. In one embodiment of the invention, multiple thin columns having separation-effective openings prepared from the same polymerization mixture are used as a filler to reduce the heat dissipation problem during in situ preparation of the large columns. In another embodiment of the invention, a polymer rod is used as the filler for the same purpose. In one embodiment of this invention, the filler material is large non-porous silica beads.

The polymers, monomers, initiators, porogens, additives and polymerization temperature are selected to improve the characteristics of the column and may be used with an embodiment of polymerization using pressure during polymerization or with other processes. Some of the aspects of this process may be applied to monomers and polymers formed in a polymerization reaction other than free radical reactions such as the polycondensation reactions and sol gel process which form silica monolith.

The column hardware in one embodiment of the invention includes rigid tubes to be used as chromatographic columns, with various shapes including cylindrical, conical, rectangular, and polygonal or an assembly of these tubes. The tube may be made from any conventional materials know in the art including metal, glass, silica, plastic or other polymers, more preferably the stainless steel or glass. The inner dimension of this tube can be from micrometers to meters in diameter, thickness, width, or depth. The permeable solid material may span the entire cross-section area of the tube where the separation of the samples take place by passing through the tube axially or radially (Lee, W-C, et al, "Radial Flow Affinity Chromatography for Trypsin Purification", Protein Purification (book), ACS Symposium Series 427, Chapter 8, American Chemical Society, Washington, D.C., 1990.) depending on the mode of separation, more specifically the axial or direct flow chromatography or the radial flow chromatography. The inner surface of the column or mold with which the polymerization solution is in contact during polymerization may be non-reactive or may be treated to increase adhesion to the surface of the plug. The tube can incorporate any usable fittings know in the art to connect it with other instruments, more specifically chromatography instruments.

In an embodiment of this invention, the monolithic permeable solid polymer is formed in a capillary tube, which can be for example a capillary tube with an internal diameter if 150 micons. In another, very significant, embodiment, the monolithic permeable rigid material is formed and sealed, often under pressure, in a removable 80.mm i.d. Teflon® sealing ring. This ring and column may be sold as a low-cost, reliable, high capacity, high resolution, very fast, easily replaceable, replacement chromatographic column. In another embodiment, the diameter of the tube is 10 mm. In another embodiment, the tube diameter is 4.6 mm and the material is stainless steel. In another embodiment of this invention, a plastic syringe barrel is used as a column. In another embodiment, the monolithic matrix is formed in a mold containing a metal container, a sealing plate and an insert with multiple cylindrical holes. The thickness of the insert varies from 1 to 10 mm. A mold can be a micro device with plurality of channels or grooves on a plate made of silica or rigid polymers. The monolithic materials can be formed in any sizes and shapes make it suitable for a specially designed micro-sized device, for example a micro-titer plates with multiple wells containing the subject media and optionally having a small elution port in the bottom. There is no limit for the designed shape and size or the applications with these devices.

The polymerization mixture is filled or injected into a column with desired shape and size depending on the final use of the product to be polymerized to form a plug having separation-effective opening for use as a solid support. Advantageously, the polymerization is done in a column in which the plug is to be used such as a chromatographic column, catalytic bed, extraction chamber or the like. In one embodiment of the invention, the positive pressure is exerted to the polymerization mixture during polymerization to control the particle size of the aggregates and to compensate for volume shrinkage during polymerization. The particle size of the aggregate has been found to be more homogeneous and larger than that from non-pressurized polymerization. The volume shrinkage during polymerization is compensated by a positive air pressure or a moving piston with positive pressure.

More specifically, a polymerization mixture is applied to a column in the preferred embodiment or to some other suitable mold. Polymerization is initiated within the column or mold. The column or mold is sufficiently sealed to avoid unplanned loss by evaporation of porogens or monomers if the polymerization is in an oven, or to avoid contamination or dilution if polymerization is in a water bath. During polymerization, pressure is applied to the polymerization solution. Preferably the pressure is maintained at a level above atmospheric pressure to control the size of the aggregates and its distribution in the polymer, and to prevent the formation of voids on the polymer wall surface and inside the media by shrinkage, and to prevent the media from separating from the wall of the column which forms alternative fluid path through the gap or wall channels, until polymerization has been completed. Maintaining the column at atmospheric pressure to accommodate shrinkage did not prevent the formation of voids in every case and provided poor reproducibility. The pressure source can be a gas pressure, a pressure from non-compatible liquid, a piston driven by air pressure, sprint force or hydraulic pressure.

In one embodiment of the invention any number of pressurized molds (tubes) can be kept at constant or controlled temperature in a single water bath, and identically pressurized from a single (e.g. nitrogen, water, etc.) manifold. This increases both uniformity and speed of production.

In another embodiment of the invention, a selected pressure is exerted on the polymerization mixture by high pressure nitrogen. In still another embodiment of the invention, a selected pressure is exerted on the polymerization mixture during polymerization by a pressurization device shown in FIG. 2,3 or 4. The column is sealed in one end and the polymerization mixture is filled into this column. The other end is sealed by the device shown in FIG. 2,3 or 4. The whole assembly of the polymerization fixture including the column is shown in FIG. 2,3 or 4. The pressure is applied to the polymerization by a piston with a smooth Teflon plug driven by a hydraulic pressure from a syringe pump. The polymerization mixture was sealed in the column by the Teflon plug and an O-ring. When a constant positive pressure is applied to the polymerization mixture, the actual pressure is the difference between the hydraulic pressure and the friction. During the polymerization, the piston moves into the column upon the conversion of the monomers to polymers to compensate the voids generated due to the shrinkage of the polymers. This prevents any negative pressure and void space generated inside the sealed column due to this shrinkage thus improves the column efficiency.

It is believed that the shrinkage is in every direction. The resulting voids are probably occupied by the nitrogen gas generated by AIBN or by solvent vapor with negative pressure inside the column. The voids can be a large irregular dents on the polymer wall or small irregular dents spreading the entire polymer surface. The voids can also be distributed inside the polymer resulting in inhomogeneity of the separation-effective opening size distribution. These irregular voids and gaps result in the wall effect or zone spreading of the column. They are detrimental to the column efficiency and lower the resolution of the column. These voids and gaps also result in low reproducibility of the column performance from one to the other in the same batch of production or from batch to batch of the productions.

In one embodiment of the invention, a selected pressure is exerted to the polymerization mixture to control the size of the aggregates and the separation-effective opening size distribution. The particle size changes with the change of the pressure on the polymerization mixture during polymerization. The particle size is larger at higher pressure. Under the positive pressure, the shrinkage of the polymer during polymerization happens only at the direction of the pressure force. This prevents the formation of voids inside the polymer and the voids/gaps on the wall surface adjacent to the column wall.

During the polymerization process, the monomer concentration continues to decrease with the increasing conversion of the monomers to polymers. The crosslinked polymers continue to precipitate out of the solution and aggregate with each other to form larger particles or clusters. These particles precipitate and linked to each other by crosslinking agents such as an active polymer chain with a vinyl group. These interconnected particles sediment to the bottom of the column, which result in the lower monomer concentration at the top part of the column.

The separation-effective opening size is highly affected by the total monomer concentration and their ratios. An in-homogeneous separation-effective opening size gradient is formed along the direction of gravity, which results in zone spreading. Since the particle size is partly controlled by the pressure of polymerization, the gradient of separation-effective opening size can be corrected by adjusting the pressure during the polymerization. In one embodiment, the linearly increased pressure is exerted to the polymerization mixture during polymerization. In another preferred embodiment, the step pressure gradient is exerted to the polymerization mixture during polymerization. The speed and pattern of increasing/decreasing the pressure is chosen to control the particle size of the aggregates and its distribution during the entire polymerization process. When a linear gradient of separation-effective opening size distribution is desired, it can also be achieved by changing the pressure during the polymerization with different speed and different maximum pressure.

The polymerization temperature depends on the choice of initiator. When AIBN and Benzoyl Peroxide are used, the typical temperature range is from 50 to 90 degree C. The heating source can be any known in the art. The preferred ways are temperature controlled heating bath or oven. The reaction time can be from 0.5 to 48 hours depending on the choice of initiator and reaction temperature. In one embodiment of this invention, the polymerization is carried out in a temperature controlled water bath at 60° C. for 20 hours.

Irradiation, such as IR, UV-vis or X-ray, is used as the source for polymerization when light sensitive initiator is used. In one embodiment the reaction starts by thermal activation of the initiator. In another it starts by the application of energetic radiation such as x-rays, either with or without a chemical initiator. If x-rays are used the initiator should selected to thermally activate at temperatures well above, the polymerization temperature. On the other hand the initiator activates when under x-ray irradiation at temperatures in the given region desirable for the reaction mass to receive activation. The initiator is also selected so that activation time and temperature for dissociation is considerably less than for the monomers alone. The production of active initiator (free radical) is controlled only by the X-rays intensity. Since the X-ray intensity is controllable, the reaction rate is controllable and won't "run away" or overheat. Moreover, the initiator may be chosen to activate when under X-ray irradiation at temperatures in the given region desirable for the reaction mass to receive activation.

In one embodiment, x-rays are used as the energy source for polymerization. Energy of the x-ray photons are varied with the preparation of the polymers with difference thickness or cross-sections. Lower energy x-ray is used for preparation of smaller diameter polymer rods and higher energy x-ray or exposure to lower energy x-ray for a longer period of time may be used for preparation of large diameter polymer rods. In the preferred embodiment, the polymerization temperature is controlled by switching the x-ray on/off. When x-ray is switched off, the polymerization is quickly shut off. within several seconds since the lifetime of the free radical is typically around one second.

In one embodiment, photo initiator is used to initiate the polymerization using x-ray as the energy source. The photo initiators are the typical photo initiators used in photo polymerizations- in the polymer field including γ-ray, x-ray, UV, Visible and IR sensitive photoinitiators. The photo initiators include azo compounds such as azobisisobutylonitrile, peroxides such as Diphenyl (2,4,6,-Trimethyl Benzoyl) Phosphine Oxide, ketones such as phenanthrenequinone, 2-chlorothioxanthen-9-one, 4,4'-bis(dimethylamino) benzophenone, 4,4'-bis(diethylamino)benzophenone, 4,4'-bis(dimethylamino)bezebophenone, 2-chlorothioxanthen-9-one, Benzil Dimethyl ketal, Organic metallic complexes. These photo initiators include the ones used in both cationic and free radical polymerizations. In one embodiment, AIBN is used as the photo initiator. In another embodiment, phenanthrenequinone is used as the photo initiator.

In one embodiment, x-ray sensitizer or scintillator is used in combination with the photo initiator. The scintillators which can be used include all the luminescence materials in the prior art. The scintillators include the compounds -containing benzene rings such as terphenyls, quarter phenyls, naphthalenes, anthracenes, compounds containing heterocycles, compounds with a carbonyl group, compounds with two or more lurorophors and organometallic compounds, and inorganic compounds such as $ZnTe$, $ZnSe$, $ZnS$, $CsI$, $Gd_2O_2S$ and $CaWO_4$. In some embodiments, 2,5-diphenyloxazole (PPO), 2-phenyl-5-(4-biphenylyl) 1,3,4-oxadiazole (PBD), 2-(1-Naphthyl)-5-phenyloxazole (á-NPO are used as scintillators. In one embodiment, terphenyl is used as the scintillator. In another embodiment, ZnSe is used as the scintillator. The mechanism of the initiation using the combination of scintillators and photoinitiators is believed to be a multiple step initiation process. First, the x-rays activate the solvent molecules to form electronically excited solvent molecules. The excited solvent molecules rapidly transfer their excitation energy to the scintillator forming electronically excited scintillator. Then, the excited state of the scintillator relax to ground state by emission of photons. The emitted photons were absorbed by the photo initiators and forming active free radicals. The free initiator free radicals contact the vinyl function groups of the monomers and start the polymerization process. The process can be depicted as followings:

X-ray hγ—excited solvent molecule*—excited scintillator molecules*—UV or Visible hγ'—excited initiator molecules*—initiator free radicals-polymer radicals x-ray irradiated polymerization can be used for preparing homopolymers such as polystyrene, polytetrahydrofuran, resins such epoxy or other crosslinked materials, and porous polymer support such as separation media in the shape of columns, membranes, or materials in any other housings. The method can be used for preparation of molded parts in any shape. In one embodiment, polystyrene is prepared by using x-ray irradiation as energy source. Polystyrene is prepared in a mold of a glass vial with narrow opening and in a shape of a cylinder. Both solution polymerization and bulk polymerization are used to prepare homopolystyrene materials. In another embodiment, polyglycidylmethacrylate resin is prepared by using the same method. In another embodiment, porous poly(styrene-co-divinylbenzene) is prepared. In another embodiment, porous poly(glycidyl methacrylate-co-ethylene glycol dimethacrylate) polymer support is prepared.

X-rays can be used for preparing porous monolithic polymer supports with cross sections from micrometers to meters, and the particle-shaped polymer supports as well. X-ray irradiated polymerizations are used to prepared monolithic liquid chromatography columns including capillary and microbore analytical columns, conventional analytical columns, and preparative and process columns, In one embodiment, porous monolithic support in a glass column with inner diameter of 1 cm is prepared. The column is characterized by SEM, porosimetry and chromatography. The poly(styrene-co-divinylbenzene) monolithic column in this glass housing shows excellent separation of peptides. X-rays can penetrate the materials in depth. Both organic and inorganic polymers can be prepared using x-ray or γ-ray. High energy x-ray and γ-ray can travel the materials in high depth. If a greater such depth is required, the unpolymerized mixture can be placed in the x-ray beam, and rotated and translated in a way chosen that the overall, time-averaged irradiation is sufficiently uniform throughout the body being polymerized. Note that radiation aligned in the intended direction of chromatographic flow does not cause significant chromatographic nonuniformity in the bed because of absorbance of the radiation beam. Axial nonuniformities do not necessarily degrade performance as radial nonuniformities do. Low energy x-ray penetrates the materials in less depth but is safer to use. In one embodiment, low energy x-ray was used to prepare a porous monolithic support in a glass column with the diameter of 3.5 cm. In another embodiment, a monolithic support in a polymeric columns housing with 88 mm diameter is prepared. The temperature of polymerization is controlled by controlling the intensities and energies of the x-ray photons and by a water jacket so at least one side of the reaction mixture. Preferably such water cooling cools the column in its axial direction but not the radial direction to avoid thermal gradient and resulting inhomogeneity. All flow paths experience the same inhomogenuity in the direction of chromatographic flow, and thus have no effect upon the separation. The polymerization temperature in the center of this large diameter column is about the same as the polymerization temperature on the edge of the column during the whole polymerization process. The conversions of the monomers are completed after 4 days of polymerization.

X-ray irradiated polymerization can be combined with thermal polymerization. Polymerization rate and porosities can be controlled by the rate of polymerization, which can be controlled by the energies and intensities of x-ray, and the temperature of polymerization. In consideration of the economy and safety of irradiated polymerization process, lower energy and intensity x-ray is preferably used in preparation of large diameter monolithic polymer support. The conversion of monomers is more than 70% complete after 48 hours of polymerization in the 3.5 cm diameter column. In order to speed up the polymerization rate and finish the conversion in a short time, thermal polymerization at desired temperature corresponding to the initiators is used. In one embodiment, porous poly(styrene-co-divinylbenzene) is prepared by using x-ray irradiation followed by thermal polymerization at 70° C. after the x-ray irradiated polymerization. The porosity of the polymer can be controlled by monomer compositions, x-ray intensity and energy, choice of initiator and scintillator combination, and the polymerization temperature in both x-ray irradiated polymerization and thermal polymerization. The porogenic solvents used in this polymerization process is the same as those used in pure thermal polymerization described earlier. Excellent polymer support is obtained for liquid chromatography use.

Ultraviolet and visible light radiation has been used in the past for preparing polymers including homopolymers, slab-shaped polymer resins and porous polymer surface coatings but not the polymer materials in this invention. Both UV and visible light can penetrate thin, solid, clear materials. Ultraviolet and visible lights have been used to prepare thin, clear materials such as membranes. The homogeneity of a porous polymer becomes more of a problem when the thickness of materials increases. This is due to the scattering and attenuation of lights through the porous solid materials. The depth that the light can travel through the solid materials decreases quickly depending on the functional groups and the refractive indexes of the materials. Consider an acrylic, dry porous column, made of two phases: acrylic resin refractive index about 1.5 and air with refractive index of 1.00. This scatters light so completely that this material looks like chalk, white and opaque. Heretofore then these apparent differences have prevented the use of UV or visible light for polymerization. This patent application discloses a method of using ultraviolet and visible lights to prepare polymer materials including materials listed above with high homogeneity. This patent application also discloses a method of preparing polymer materials many inches thick.

In this invention, a solvent of very similar or the same refractive index to the targeted polymer resins at the selected wavelength of light is chosen for the polymerizations. The lights at the selected wavelength can travel though the polymers during the polymerization due to the little used Christiansen Effect, wherein the targeted porous resin becomes quite translucent or transparent. Light in a particular wavelength range show transparency because the pores are full of solvent. Preferably, monochromatic light, of which the indices of the refraction in both the polymer solid and solvents are very close, is chosen for the polymerization. An initiator activated by light rather than heat is used with a photoinitiator. If white light is used, the transmitted light corresponds to the particular wavelength at which the refractive indexes of the light in both polymer solid and the solvent or solvent combinations are very close. A photo initiator is chosen to absorb and be activated by light in the near transparent polymer and solvent wavelength range. The initiator absorbs this wavelength range. Preferably, when a photoinitiator is activated it breaks up onto fragments lacking in the original chromophores. Such fragments have no absorption in the range of selected wavelength of the light. When a light ray is absorbed by the chromophore in a photo initiating molecule the result is local polymerization at the surface. If the chromophores survive this reaction they will be there to block the next ray of light from activating the next photo initiator molecule, hence limiting polymerization to the original surface. Therefore, the light can travel through the polymer mixture in more depth and the transmission of the light increases. This effect is known as Bleaching Effect. It has been found that a good photo initiator in this respect is 2,4,6-trimethylbenzoyidiphenylphosphine oxide. The bleaching effect and the Christiansen effect are synergistic in the production of very thick layer, or deep, porous polymers by photoinitiation or e-ray initiation. In the latter case x-rays excite the solvent which then transmits secondary energy to a so-called "sensitizer" which then fluoresces to activate the initiator. It can also be seen that if the solvent when excited by x-ray also in itself fluoresces, an additional degree of synergy exists. However, often the use of p-terphenyl as a sensitizer for x-ray polymerizations. Fluorescing solvents that are used include many aryl compounds such as toluene, o-, m-, or p-xylene, or the 1,2,3 (or other isomers of) mestylene. In one embodiment, homopoly(glycidyl methacrylate) is prepared by ordinary solution polymerization using o-xylene as the porogenic solvent. The refractive indexes of 0-xylene, the monomer and especially the polymer are close. The resulted polymer in solution is close to transparent but a little translucent due to minor scattering of the white light.

The refractive indexes of target polymers are measured. Both the good and poor solvents are selected to have the refractive indexes close to the refractive indexes of the target polymers. By tuning the ratio of the solvents, the refractive indexes of the solvent mixture will be almost the same as the polymer. Therefore, the transmission of the light through the polymer swelled by the solvents can reach the maximum. In one embodiment porous polymethacrylate based monolith is prepared by using the combination of solvents.

The resulting permeable polymer may have more than one suitable configuration. One has a desired separation-effective opening size distribution for target applications. In general, it includes small separation openings less than 300 nm in at least one direction which provide high surface area for separation, and large separation openings such as larger than 500 nm for the majority mobile phase to go through. Preferably the sizes of large separation-effective opening are between 2 to 5 microns for medium and low pressure separation media, and 0.6 to 2 microns for high and medium pressure separation. The separation-effective opening size distribution and the irregular feature size distribution can be controlled by the types and amount of porogens, monomers, initiators and polymerization temperature, time and pressure. In one embodiment, the monomers are selected not only to have desired functionality, but also to help improve the column efficiency by changing the kinetics of polymerization and polymer structure, which leads to more ideal separation-effective opening size distribution. The ratio of monomers is selected for the same purpose. The type and amount of porogens are selected after careful investigation for the generation of the desired separation-effective opening size distribution. The use and selection of pressure during polymerization is particularly important for the generation of the desired separation-effective opening size distribution and the homogeneity of the separation-effective opening size distribution through out the whole column. It also prevents the formation of irregular voids and wall channels which happened in conventional sealed or open polymerization.

It has been found that the formation of micropores can be drastically reduced or prevented by using pressure during polymerization and the careful tuning of the other polymerization conditions and reagents. From Scanning Electron Microscopy (SEM) studies of this polymer having separation-effective openings, it is found that the polymer particle morphology is similar to some form of coral. The coral-like polymer is formed of interconnected corrugated particles which apparently have grown by accretion. The interior of these particles are non-porous. The surface is highly corrugated and contains huge number of small open shallow grooves with various sizes of openings. In SEM study of one of the polymers the particles are core-shell structured with short depth of the openings. These unusual corrugated polymer structures and core-shell particle structures without through pores in the individual particles greatly improve the capacity of the monolith compared to regular non-porous separation media while avoiding the mass transfer problem in conventional macroporous media containing a large number of micropores and mesopores inside the particle or beads. These structures are also dramatically different from so called "Perfusion Beads" or monoliths with though pores disclosed in the literatures. The aggregates of particles in some columns conditioned by the application of pressure or by holding the volume against expansion when internal forces tend to swell or expand the polymer results in stacked generally flat or nested configuration rather than the aggregated substantially round aggregates of particles.

The monolith in this invention combines the advantages of high resolution in non-porous particle packing and the high capacity of macroporous packing while avoiding their problems. These corrugated particles may grow by accretion from polymer nucleus which are swelled and surrounded by monomers and active oligomers, and merging with other polymer nucleus. These particles aggregate with each other and are reinforced by crosslinking. This structure improves the column efficiency greatly by prevention of the trapping of sample molecules in the micropores, and in the pores inside the particles, which are one of the major reasons for zone spreading according to the theoretical model. The size of the particles, aggregates or clusters can be finely tuned to be more homogeneous, and the separation-effective opening size distribution can be improved to give high resolution separation by careful control of pressure in combining with the selections of other factors discussed earlier.

Satisfactory separation of more hydrophilic compounds in liquid chromatography often requires the starting mobile phase to be 100% water with no organic solvent. This type of separation can not be achieved to a satisfactory extent with reversed phase media based on pure styrene/divinylbenzene, polymethacrylates and their derivatives containing C4, C8, C12 and C18, which are very hydrophobic. The polymers shrink in aqueous mobile phase with low organic solvent contents. The shrinkage results in void space between the column wall and the polymer media, which leads to so called "wall channeling" in chromatography. As the consequence, the sample and mobile phase bypass the media and go through wall channels instead of the media. The sample is not retained or partly retained which results in multiple peaks for each pure sample.

In one embodiment, wall effect is avoided by first shrinking the media down to the maximum extent by passing pure water or salt solution through the media, and then followed by compression of the media with piston fittings until the void space between the wall and polymer media is sealed. The piston is held in place by a nut fitting. The fittings are shown in FIGS. 3 and 4. The shrinkage and sealing of the wall void can be monitored by first decreasing then increasing the back pressure of the column. This process prevents the formation of the "wall channeling" during the separation process. In one embodiment, the polymer is shrunk in pure water and compressed with PEEK piston fittings. In another embodiment of this invention, the polymer is shrunk in 1 mol/l NaCl solution and compressed with PEEK piston fittings.

In highly polar environments, the linear polymer chain, and the chains of C4, C8, C12, C18 on the polymer surface collapse to the surface resulting in poor interaction between the sample molecules and the surface of the media. Also, the bed is very poorly wetted by the mobile phase due to the extreme difference in polarity of the media and mobile phase. The mass transport and interactions between the sample and stationary phase is very poor, which result in low column efficiency and resolution. These problems and the problem of "wall channeling" are reduced by increasing the hydrophilicity of the polymer matrix while maintaining the desired hydrophobicity for sample retention and separation.

The polymer matrix contains hydrophilic functional groups such as hydroxyl, amide, carbamide or hydrophilic moieties in the polymer repeating units. The polymer can be wetted and swelled by water due to the hydrophilicity of the polymer matrix. The surface of the polymer media still contain highly hydrophobic polystyrene chain, or C4, C8, C12 and C18 chains for the hydrophobic interation in reversed phase chromatography. The shrinkage of the polymer in water is reduced or completely prevented, which also solve the problem of wall channeling. The hydrophilicity can be improved by direct copolymerization of monomers containing hydrophilicity moieties, or by modification of polymers to incorporate the hydrophilic moieties.

In one embodiment of this invention, hydrophilic hydroxylethyl methacrylate is copolymerized with styrene and divinylbenzene for the prevention of "wall channeling" and collapse of the hydrophobic interaction chains in water. In one embodiment of this invention, stearyl acrylamide is copolymerized with stearyl methacrylate and ethylene glycol dimethacrylate. The addition of hydrophilic monomers also may decrease protein denaturation in reversed phase columns. In one preferred embodiment, acrylonitrile is copolymerized with styrene and divinylbenzene. The polymers swell more and more with the increase of the hydrophilicity of the hydrophilic monomers. The reverse phase separation media constructed with the polymer containing hydrophilic moieties will swell in both aqueous and non-aqueous solutions. This enlarges the applicability of reversed phase separation media in aqueous mobile phase.

In Situ polymerization can be used to prepare the columns with any sizes and shapes. In one embodiment, a capillary column with cylindrical shape of inner diameter of 75 µm was prepared. In another embodiment, a column with 4.6 mm ID was prepared. In another embodiment, a column with 88 mm ID was prepared. In another embodiment, a square capillary column with cross-section of 100 µm and on up to 700 µm was prepared. In another embodiment, a polymer disk with 3 mm thickness and 1 cm inner diameter was prepared. In another embodiment, a donut shape monolith with 1 cm outer diameter and 4.6 mm inner diameter was prepared. In another embodiment, a microchip column with 100 µm inner diameter grooves was prepared.

Hydrophobic interaction chromatography requires very hydrophilic separation media with mild hydrophobicity. Upon further increase of the hydrophilicity of the matrix with less hydrophobic carbon chain or polymer chain, the reversed phase media can be turned into hydrophobic interaction media.

Normal phase chromatography requires hydrophilic media, whose surface is fully covered by hydrophilic functional groups. Hydrolysis of the epoxy group in poly(glycidyl methacrylate-co-ethylene glycol dimethacrylate) was used in prior art to obtain normal phase separation media. The Normal Phase separation media is prepared by in situ direct polymerization of hydrophilic monomers containing hydrophilic functional groups such as hydroxyl and amide. In one embodiment hydroxyethyl methacrylate is copolymerized with a crosslinker, such as EDMA, to obtain normal phase media. In one embodiment of this invention, the column hardware is a polypropylene barrel reinforced with glass fibers.

The reversed phase monolithic media prepared according to prior art has extremely low capacity and is compressed during separation. The loading capacity of the liquid chromatography media and the rigidity of the media is increased by increasing the crosslinking density of the media. The crosslinking density is increased by using higher amount of crosslinker, such as divinylbenzene, in poly(styrene-co-divinylbenzene) monolith. In one embodiment of this invention, 100% of divinylbenzene (80% purity. The rest of them are mostly ethylstyrene. It is the highest purity grade available commercially.) in total monomer is used. The capacity is six times higher than the monolith prepared in the prior art. The high capacity monolith prepared under pressurized polymerization has high resolution as well as high capacity. In one embodiment of this invention, 90% of the divinylbenzene (80% purity) in total monomer is used. In another embodiment, 80% of the divinylbenzene (80% purity) in total monomer is used.

Another method of improving the rigidity and resolution of the media is by increasing the total polymer density in the column. The total polymer content is increased by increasing the total monomer content in the mixture. By increasing the total monomer content in the polymerization mixture, the resolution of column is improved as well. The separation-effective opening size and its distribution are highly affected by the total monomer concentration in the polymerization mixture. In one embodiment of this invention, 46% weight percent of total monomers is used to improve the rigidity and resolution of the media.

The monolithic media prepared in the prior art has poor resolution, low speed of separation, low rigidity and extremely low capacity. The prior-art monolithic polymethacrylate based weak anion exchanger was prepared by modification of poly(glycidyl methacrylate-co-ethylene glycol dimethacrylate) with neat diethylamine. It swells extensively in water and can not be used at high flow velocity. This medium has very low rigidity and is not stable at flow velocities more than 6 cm/min. The back pressure of the column keeps increasing during the runs. Two methods of improving the rigidity of the hydrophilic medium are provided.

First, the rigidity of the medium can be improved by increasing the crosslinking density of the polymer matrix. At low crosslinking density, there are a lot of non-cross linked linear polymer chains which are solvated by water and extend out to the solvents. The polymer matrix expands due to this extensive solvation. The expansion of polymer matrix in a polymer narrows the size of the separation-effective openings and interstitial spaces between the interconnected particles. The porosity is also decreased. These result in high back pressure. The highly solvated porous polymer has characteristics of soft gel. Under a pressure, the soft polymer can be compressed easily and leads to higher pressure. The increase of pressure will further compress the medium and lead to even higher pressure. The cycle of pressure increase and compression make the prior art monolith not useful for the application in high speed separation.

Upon the increase of crosslinking density, the swellable linear polymer chains are shortened and the swelling is reduced. The polymer with separation-effective openings becomes more rigid. The structure with separation effective openings is maintained in aqueous solvents. High porosity and larger separation-effective opening size can be obtained with highly crosslinked polymer matrix, which allows higher flow rate to be used without the detrimental cycles of the compression and pressure increase. High speed separation can be achieved by using high flow rate.

In one embodiment of this invention, the cross linking density of the ion exchanger is greatly improved by using 70% crosslinker, ethylene glycol dimethacryalte (EDMA). In a preferred embodiment, the amount of EDMA is 50%. In another preferred embodiment, the amount of EDMA is 60%. EDMA is more hydrophobic than its copolymers containing ion exchange groups. By increasing the amount of EDMA, the hydrophilicity of the polymer matrix is reduced. This results in decrease of swelling and improves the rigidity. This is the additional advantage from using more hydrophobic cross linker instead of hydrophilic crosslinker when high rigidity of the polymer in aqueous phase is highly desired.

Second, the rigidity and column efficiency of the polymer separation media are both improved by controlled modification in this invention. The glycidyl methacrylate (GMA) is hydrophobic before it is modified to contain ion exchange functional groups. The GMA in prior art monolithic weak anion exchanger (WAX) is modified by reaction with neat diethylamine at 60° C. for 3 hours. Neat diethylamine can swell the polymer and diffuse into the polymer particles to access the GMA epoxide groups. This modification reaction modifies not only the GMA moieties on the separation-effective opening surface of the polymer but also those inside the polymer matrix. The hydrophilic moieties containing the ion exchange functional groups intermingle with hydrophobic backbone both inside and outside the separation-effective openings after modification. This non-selective modification makes the whole polymer matrix swell extensively in water while some hydrophobic backbones are exposed on the surface of the separation effective openings. The hydrophobic patches on the surface of the separation openings can result in secondary hydrophobic interaction during ion exchange chromatography separations, which leads to zone-broadening.

A controlled modification of the GMA on the surface of the polymer particles can keep the internal part of the particle more hydrophobic and less swellable in water. After modification of the surface GMA, the surfaces of the particles become much more hydrophilic and attract the water molecules. Those more hydrophobic backbones retreat to inner part of the polymer particles to stay with more hydrophobic cores of the particles, and get away from the very polar buffer environment during chromatography separation. This increases the coverage of surface with hydrophilic ion exchange groups and prevents the zone-broadening from secondary hydrophobic interaction. The controlled surface modification is accomplished by catalyzed modification reaction in aqueous solution at lower temperature. The catalyst is preferably an acid or reagent which can generate protons in situ.

In the preferred embodiments of this invention, a dialkyl amine hydrogen chloride salt is used as a catalyst. The salt solution is very polar and has less tendency to swell the hydrophobic polymer. The ionic catalyst tends to stay in solution instead of diffusing into the very hydrodrophobic internal matrix. The lower reaction temperature reduces the swellability of the polymer. Diethyl amine might diffuse into the polymer matrix but the reaction of diethyl amine with GMA at low temperature is very slow and insignificant. In one embodiment of this invention, the dialkyl amine hydrogen chloride catalyst is diethyl amine hydrogen chloride. In another embodiment of this invention, the catalyst is trimethyl amine hydrogen chloride. In one embodiment of this invention, the reaction temperature is 25° C. In another embodiment of the invention, the modification temperature is 30° C.

The prior art processes for the synthesis of monolithic weak cation exchangers are based on membrane, beads and gels and none of them can be used directly in the in situ preparation process of monolithic columns. Seven methods for preparing a weak cation exchanger a described below. All the modification reactions in these methods are carried out by pumping the modification solution through the column continuously at a selected temperature, or the reagents are sealed inside the column and heated in a heating bath or oven after the reagents are pumped into the column.

The first method is the two-step modification of poly(glycidyl methacrylate-co-ethylene glycol dimethacrylate) (PG-MAEDMA) with chloroacetate salt. Sodium chloroacetate has been used to modify hydroxylethyl methacrylate based material to obtain carboxylic acid groups in the literature. In order to take advantage of the above reaction for the modification of monolith, the epoxide ring in GMA is first opened to obtain hydroxyl group by hydrolysis using 1 M $H_2SO_4$ aqueous solution. In the second step, chloroacetate couples with the hydroxyl group in the polymer to attach the carboxylic group to the polymer. This reaction is catalyzed by strong base such as sodium hydroxide. The reaction temperature is from 40 to 80° C., preferably from 50 to 70° C. The reaction time is varied from 1 to 24 hours, preferably less than six hours. In one embodiment of this invention, the modification reaction takes place by pumping 5 M sodium hydroxide aqueous solution through the monolithic column at 60° C. for 2 hours. The capacity of this media is not ideal although the column efficiency is good. The capacity can be increased by longer reaction and higher reaction temperature. However, the separation medium becomes soft due to the side hydrolysis reaction of the esters in the polymer. The crosslinking density is lowered since the crosslinker EDMA is hydrolyzed as well.

The second method is a one-step modification of the GMA in the polymer to obtain the carboxylic functional groups using glycolic acid as reagent. Glycolic acid is reacted with PGMEDMA at temperature between 40 to 90° C. for 1 to 24 hours. This reaction is a self catalyzed reaction since glycolic acid is a catalyst itself. The reaction can be catalyzed by other stronger acid such trifluroacetic acid (TFA). The reaction is simple but the capacity of the weak cation exchanger is low due to a parrarel side reaction. The epoxide ring can be opened by hydrolysis reactions as the side reaction. In order to prevent this reaction, the non aqueous solvent is used. Preferably, solvent containing protons is used. In one embodiment of this invention, glycolic acid solution in formic acid containing TFA catalyst is pumped through the column for 3 hours at 80° C.

The third method is a double modification of the PGMEDMA with both glycolic acid and choroacetate. There are several advantages of the double modification reactions. First, they can all be performed in aqueous solution; Second, both reaction steps lead to desired product; Third, the side reaction of the first step leads to the desired functional group for the second step modification; Fourth, the conditions of double modification reaction can be milder than the single reaction to obtain the same or higher capacity while avoiding the hydrolysis of the backbone which maintains the rigidity of the matrix. In one embodiment of this invention, the first reaction is performed in glycolic acid aqueous solution containing TFA as catalyst, and the second reaction is the substitution reaction of chloroacetate by NaOH aqueous solution.

The fourth method is a one-pot reaction of glycolic acid and chloroacetate. Instead of the double sequential reactions, both reagents are put into the solution together during reaction. The reaction with glycolic acid is base-catalyzed instead of acid-catalyzed. This method has the the advantage of the third method but with lower capacity due to less reactivity of the base-catalyzed ring-opening reactions by glycolic acid in water.

The fifth method is a hydrolysis reaction of acrylates or methacrylates. The hydrolysis of the ester groups leads to the carboxylic functional groups. The direct hydrolysis of PGMEDMA membrane or beads is known in the prior art. However, the resulting media did not have either good capacity or separation. It is discovered in our work that both the resolution and capacity can be dramatically improved by hybriding the hydrophilic and hydrophobic acrylates or methacrylates. The hydrolysis reaction is much more efficient since the water molecule can diffuse into the surface of the particles and wet the surface much better due to the hydrophilic moieties of the acrylates. The reaction can be catalyzed by both acid and base, such as TFA or NaOH aqueous solution. In one embodiment of this invention, poly(methyl methacrylate-co-hydroxylethyl methacrylate-co-ethylene glycol diemthacrylate) is prepared and hydrolyzed to obtain weak cation exchanger. In another embodiment of this invention, poly(hydroxylethyl methacrylate-co-ethylene glycol dimethacrylate) is hydrolyzed. In another embodiment of this invention, PGMEDMA is hydrolyzed by acid first and base in the second step. The weak cation exchanger obtained in this method is softer due to the hydrolysis of the backbone crosslinker.

The sixth method is a direct copolymerization of acrylic or methacrylic acid. The direct copolymerization of the acid leads to the weak cation exchanger in one step. This method greatly simplifies the preparation method. The capacity of the weak cation exchanger is relatively higher than the modification method but still not ideal. The ratio of the acidic monomer to crosslinking monomer is between 2% to 30%, preferably 5% to 15%. With the higher content of the acid monomer, the capacity is higher but the media is softer. The direct polymerization method is applicable to the preparation of monolithic membranes, columns, chips, tubes or any format known in the art.

The seventh method is the combination of direct copolymerization and the controlled modification. It was discovered in this invention that this combination leads to high capacity while maintains the rigidity of the media. The resulting media can be used for high-throughput separation using high flow velocity. The improved capacity by direct polymerization of acrylic or methacrylic acid reaches a limit due to the softness of the media containing high amount of the acid. The acidic monomers are randomly polymerized and dispersed throughout these matrixes. These acids are converted to salts in buffer and resulted in extensive swelling of the media in aqueous mobile phase. Also, the hydrophobic backbone consists of carbon chains and esters are exposed on the surface resulting in secondary hydrophobic interaction during ion exchange chromatography separations. This leads to zone-broadening and tailing. The hydrophobic surface can be further modified to become hydrophilic while improving the capacity. The controlled modification improves the capacity and hydrophilicity of the media while preventing the softness of the media. Over modified media will leads to the modification inside the particles besides the modification on the surface. As discussed in the preparation of weak anion exchanger, the modification inside the particle results in extensive swelling which blocks the separation-effective opening or changing of the morphology which leads to detrimental cycle of pressure increase and compression. In one embodiment of this invention, weak cation exchanger is prepared by copolymerization of acrylic acid, methyl methacrylate (MMA) and EDMA in the first step, and hydrolysis of the methyl methacrylate in the second step. The hydrolysis of MMA is base-catalyzed and accelerated by the presence of very hydrophilic acrylate salt, which is the conversion product of the acrylic acid after reaction with NaOH.

This methodology of combining direct polymerization and modification is applicable to the preparation of all hydrophilic polymer supports which require high number of functional groups and rigidity of the matrix at the same time. It is applicable in preparation of monolithic tubes or columns, monolithic membranes, monolithic capillary and chips or any other monolith in different format, as well as polymeric particles, gels, membranes or any other type of polymeric separation media. In particular, the resolution and capacity of monolithic membrane can be improved with this method. The improvement can be achieved by in situ process of by off-line process. The monoliths or beads obtained by direct polymerization can be modified by pumping the reaction solution through the packed columns or membranes, or immerge them into the modification solution. The beads can be suspended in the modification solution. By using this methodology, we developed high capacity strong anion exchanger (SAX) and strong cation exchanger (SCX).

The prior art processes for making monolithic strong anion exchangers are based on membrane, beads and gels and are not applicable to the manufacture of monolithic strong anion exchange column. Three methods of preparing monolithic strong anion exchange column in situ are provided below.

Method one is the combination of highly rigid polymer and controlled modification of the surface. Modification of PGMEDMA with trimethylamine hydrogen chloride has been used to obtained membrane and bead based strong anion exchanger. When the reaction is used for preparation of monolithic strong anion exchangers, the resulting media is soft and can not be used for high speed separation. The rigidity is improved in two ways as in the preparation of monolithic weak anion exchanger in this invention: High crosslinking density and Controlled Modification reaction.

The basic polymer for SAX is formulated to contain high crosslinking density by using higher ratio of crosslinking monomer to functional monomer. The amount of crosslinker is increased to more than 50% of the total monomers in the polymer. In one embodiment of this invention, 60% EDMA in total monomers is used. The porogens and their ratios are selected to offer optimal resolution at relatively low pressure.

The controlled modification is accomplished by catalyzed amination of the PGMEDMA. The catalyst can be any base known in the art. In one embodiment of this invention, trimethyl amine is used as catalyst. The amount of the catalyst is from 1% to 50% volume of the solution, preferably between 10% and 30%. The reaction temperature is between 10 to 60° C., preferably between 20 to 50° C. The reaction time is between 10 minutes to 24 hours, preferably between 1 to 4 hours. The selected catalytic reaction modifies the surface of the particles more than the internal part of the particles, which results in the media to be used at high flow rate. In one embodiment of this invention, the reaction is carried out at 40° C. for 3 hours.

Method two is the direct copolymerization of monomers containing the quarternary amine, or their intermediate which can generate the quaternary amine in situ. In one embodiment of this invention, the functional monomer containing quaternary amine is 2-(acryloyloxyethyl] trimethylammonium methyl sulfate (ATMS). The polymer has high crosslinking density. The ratio of the crosslinking monomer in the total monomers is between 50% to 70%. In one embodiment of this invention, 60% EDMA is used. The amount of ATMS is between 2% to 20%, preferably between 5% to 15%. The third monomer which makes up the rest of monomer is preferred to be hydrophilic monomers such as HEMA although hydrophobic monomer can be used as well.

Method three is the combination of direct polymerization and controlled surface modification shown in method two and one. The strong anion exchanger obtained by method one is rigid and have high resolution. However, it suffers from non-ideal capacity. Method two improves the capacity but not sufficient and suffers from lower resolution. The combination of direct polymerization and controlled surface modification doubles the capacity and improves the resolution and recovery. The recovery of proteins is improved since the surface is fully covered by hydrophilic protein benign groups. Secondary hydrophobic interaction, which is the main reason for lower protein recovery, is minimized. The porogens are researched and selected to offer the desired flow rate. In one preferred embodiment of this invention, the combination of butanediol, propanol and water is used as porogens. The polymerization mixture and conditions are formulated to offer the optimal resolution at the desired flow rate.

Prior art processes for preparing monolithic strong cation exchangers are based on membrane, beads and gels and are not transferable to the in situ preparation of monolithic strong cation exchange columns. Three methods for preparing monolithic strong cation exchange columns in situ are provided below.

Method one is the modification of PGMEDMA with butane sultone or propane sultone catalyzed by strong base soluble in organic solvent. Modification of PGMEDMA with propane sultone using NaOH solution as the catalyst has been used to prepared membrane or bead-based strong cation exchanger. The reaction was a two-phase reaction since propane sultone is not soluble in NaOH aqueous solution. The two-phase reaction mixture can not be pumped through the column to carry out the modification. Several approaches have been taken to carry out the modification reaction. Approach one is a two-step modification reactions consist of activation of the media with strong base such as potassium t-butoxide in the first step followed by nucleophilic ring-opening reaction with butane sultone. Butane sultone is preferred since it is a liquid but propane sultone is a solid at room temperature. Potassium t-butoxide is preferred since it has higher solubility than it sodium counterpart. The solvent is a good solvent of the reagent such as dimethylsulfone (DMSO). The modification solution has to be homogeneous in order to be pumped through the column for in situ modification. Approach two is a one-pot reaction consist of both activation and modification steps. Both strong base and butane sultone are dissolved in a strong solvent. The solution is pumped through the column continuously or sealed at a selected temperature for several hours. The reaction temperature is preferably between 80 and 120° C. In one embodiment of this invention, 90° C. is used. In another embodiment of this invention, 120° C is used.

Method two is a direct polymerization of monomers containing strong cation exchange group. In the preferred embodiment of this invention, 2-Acrylamido-2-methyl-1-propanesulfonic acid (AMPS) is used as the functional monomer containing sulfonic group. The amount of AMPS is between 2% to 20%, preferably 5% to 15%. The capacity of this polymer is greatly improved comparing to the first method. The polymerization mixture is formulated to offer the optimal resolution at desired flow rate.

Method three is the combination of direct polymerization and controlled modification. In one embodiment of this invention, AMPS is copolymerized with GMA and EDMA. The polymer is further modified by controlled modification as described in method 1. Both the capacity-and resolution is greatly improved comparing to the method 1 and 2. The amount of EDMA is preferably to be between 50% to 70%. The amount of AMPS is preferably between 2% to 15%. The rest of the monomer is GMA. In another embodiment of this invention, the AMPS is copolymerized with HEMA and EDMA. The porogens are researched and selected to offer the desired flow rate. The polymerization mixture and conditions are improved to offer high resolution and high speed chromatography.

Preparation of large diameter monolithic columns for effective chromatography separation by in situ polymerization method has been a very difficult task due to the heat isolating effect of polymer formed by exothermic polymerization. It was found that the heat transfer is fast enough to prevent the inhomogeneity of the polymerization temperature as long as the shortest distance (defined as radius in this writing) between the center of the monolith to the surface of the monolith is less than 8 mm depending on the materials of column hardware.

To prepare large diameter monolithic columns, with reduced heat of polymerization problems, multiple staged polymerizations are used. The resulting polymer monoliths in each stage of polymerization have radius up to 8 mm if the mold for polymerization is made of good heat transferring material. This is accomplished by first preparing columns with radius less than 8 mm and using them as fillers for the second stage polymerization, in which the radius of the polymerization solutions between the fillers and the column wall is also less than 8 mm, and the distance between the fillers is less than 2 mm. It is found in this work that the thickness of the polymerization solution between the fillers less than 2 mm has insignificant effect on the variations of the polymerization temperature. Multiple thin polymer columns are filled into a large diameter column and filled with the second stage polymerization mixture. The column is sealed with regular fittings or fittings to allow pressurization during polymerization. The large diameter column is then placed into a temperature controlled heating bath or oven to carry out the second stage polymerization.

The thin columns are prepared by the process disclosed above with pressurized or non-pressurized polymerization. The thin monolithic columns prepared in the first stage polymerization are preferably preserved without washing and further modification. A polymerization mixture for the second stage polymerization is the same or different from the polymerization mixture of the first stage polymerization depending on the types of media. The thin columns with radius less than 8 mm can be solid rods, discs, hollow tubes with thickness of the cylinder wall less than 8 mm, or a membrane. The shapes of the above thin columns can be any shape known in the art, such as round, rectangular, triangle, etc. It is perceivable that the fillers can be other particles described in the section of filler materials in this specification.

In one embodiment of this invention, multiple thin columns with radius of 5 mm are used. In one preferred embodiment of this invention, monolithic polymer rods with size of 50 mm×10 mm I.D. are used as fillers. In another preferred embodiment of this invention, monolithic polymer rods with size of 10 mm×34 mm I.D. are used as fillers. In another preferred embodiment of this invention, the monolithic polymer cylinder with various inner and outer diameters are used as fillers.

The performance of capillary columns can be improved by our inventions described earlier. One method is to choose right combination of porogenic solvents to generate separation media with and without pressure. The choice of solvents with right polarity and solventing power of the polymers can result in porous polymer support with no micropores or small pores which can affect separation efficiency of the column. Exertion of pressure during polymerization will further improve the uniformity of the media and avoid the formation of micropores. In one embodiment, the capillary columns of internal diameter 320 µm is prepared with the combination of solvents including chlorocyclohexane and 1-decanol to generate the monolithic porous polymer support containing no micropores or small pores which result in poor mass transfer of the sample molecules with and without the pressure of 120 psi. In another embodiment, the combination of solvents including 1-ethylhexanoic acid and mineral oil has been used to prepare monolithic porous materials containing no micropores with and without pressure.

The employment of x-ray, UV-vis can improve the performance of capillary greatly. X-ray can penetrate materials low energy and intensity loss. X-ray can penetrate a capillary with almost no intensity loss. Sensitizers or scintillators can absorb x-ray energy transferred by the solvents effectively and emit fluorescence or phosphorescence light homogeneously in the solutions. The homogeneous fluorescence and phosphorescence light can be absorbed by initiators which initiate the polymerization homogeneously in the polymerization solutions. This leads to homogeneity of the porous structure of the porous polymer support including monolithic separation media and particles. This improves the column efficiency of the monolithic capillary greatly. The low temperature polymerization using x-ray as energy source results in slow polymerization rate due to the lower polymerization temperature. Fine tuning the intensity and energy of x-ray results in the desired polymerization rate which can lead to the formation of homogeneous separation media. The employment of x-ray, scintillators/sensitizers, solvents with right solventing powers and the pressure during polymerization can leads to the formation of separation media with no micropores or small pores with similar size to the sample molecules which leads to greatly improved performance. In one embodiment, capillary columns have been prepared using x-ray as energy source. In another embodiment, microchip columns have been prepared with x-ray as energy source.

The right choice of solvents with reflective index very close to the polymers allows the light to travel through the capillary with little loss of intensity of the light, which is known as Christiansen Effect and described earlier. The use of initiators having Bleaching Effect allows the UV-vis light to travel through the capillary columns with negligible loss of intensity. The lights are homogeneous in the polymerization solutions. The absorptions of the homogeneous light result in homogeneous initiations of the polymerization which is unlike the initiation promoted by thermal heating or the UV-vis initiated polymerization without the consideration Christiansen and bleaching effect. This leads to the formation of homogeneous polymerization in the solution. As the result, more homogeneous porous structure can be formed. This leads to the much improved performance of the capillary columns. The combination of the above method with solvents of good solvating power, pressurized polymerization can lead to formation of the homogeneous media containing no micropores or small pores with having no impact on column performance. In one embodiment, capillary columns have been prepared using UV-visible light. In another embodiment, microchip columns have been prepared using UV-vis light.

EXAMPLES

While many other values of the variables in the following examples can be selected from this description with predictable results, the following non-limiting examples illustrate the inventions:

General

In general, the preparation of each type of media in the following examples include three major steps, which are:(1) preparation of polymer matrix; (2) modification of the polymer matrix to contain desired functional groups; and (3) characterization of the media.

Firstly, the preparation major step, includes several sub-steps, which are: (1a) formulation of the polymerization mixture by varying the types and amount of monomers, porogens and initiators; (1b) degassing the polymerization mixture by vacuum and helium purge. (1c) assembly of the empty column with different diameter and material of tubing as a mold, frequently with one end of the column sealed with a cap or stopper; (1d) filling the column with the polymerization mixture; (1e) sealing the other end of the mold with a cap or a specially designed fitting to add pressure during the polymerization; (1f) preheating the solution in the mold with one open end if a glass column is used and applying a selected pressure using various pressure sources including hydraulic pressure, air pressure or mechanic pressure; (1g) placing the mold in a temperature-controlled heating bath or oven at a selected temperature; (1h) polymerizing for various amount of time; (1i) taking the column out of the heating bath after polymerization and replacing the sealing cap or pressurization device with column fittings for pumping the washing liquid through; (1j) washing the column with organic solvents and/or water.

Secondly, the modification process includes: (2a) formulating the modification reaction mixture with various types and amount of reactants and catalysts; (2b) pumping more than 5 bed volume modification solution through the column and sealing it, or pumping more solution continuously. (2c) carrying out the modification reaction at various temperature and time in a temperature-controlled heating bath; (2d) washing the column with organic and water.

The columns are characterized using varieties of methods including liquid chromatography separation, porosimetry, BET surface area measurement, Scanning Electron Microscopy, UV spectroscopy and visual observation. Liquid chromatography characterization includes various modes of separation at different speeds. The commonly used devices, processes and methods are described in the following preceding the specific examples.

Degassing of the Polymerization Solution

The polymerization mixture is degassed by vacuum generated by water aspirator for 5 minutes using an ultrasonic degasser. It is followed by purging the solution for minimum of 20 minutes.

Stabilizing and Conditioning Methods

The ion exchange columns were subject to a stabilizing and conditioning procedure following the washing step after modification reaction. The stabilizing and conditioning procedure for a glass column (100×10 mm I.D.) of strong anion exchanger was as following: The flow rate of 0.01 mol/l Tris.HCl buffer at pH 7.6 was increased linearly from 0 ml/min to 20 ml/min in 1 minute, and kept for 0.5 minutes. The compression liquid was changed to 1 mol/l NaCl in the same buffer by gradient in 2 minutes, kept for 0.5 minutes. The stabilizing and conditioning procedure for a PEEK-lined stainless steel column is the same as above except the maximum flow rate was 5 ml/min instead of 20 ml/min. The procedures for other ion exchange columns depend on the maximum flow rate allowed.

Characterization Procedures

1. Characterizations with Liquid Chromatography (LC) Separations

1a. LC Characterization Method 1: Liquid Chromatography Separation of Proteins and Peptides Mobile phases:

Mobile phase A (or Buffer A):

Anion Exchange Chromatography: 0.01 M Tris.HCl (pH 7.6)

Cation Exchange Chromatography: 0.01 M sodium phosphate (pH 7.0)

Reversed Phase Chromatography: 0.15% Trifluoroacetic acid (TFA) in water

Mobile phase B (or Buffer B):

Ion Exchange Chromatography: 1 M NaCl in Buffer A

Reversed Phase Chromatography: 0.15% TFA in acetonitrile (ACN) chromatography Samples:

Anion Exchange Chromatography:

0.6 mg/ml myoglobin, 1 mg/ml conalbumin, 1 mg/ml ovalbumin and 1 mg/ml trypsin inhibitor.

Cation Exchange Chromatography:

1 mg/ml connalbumin, 1 mg/ml ovalbumin and 1 mg/ml trypsin inhibitor.

Reversed Phase Chromatography for proteins:

1.5 mg/ml Ribonuclease A, 0.5 mg/ml Cytochrome C, 1.5 mg/ml BSA, 0.9 mg/ml Carbonic Anhydrase, 1.5 mg/ml Ovalbumin.

Reversed phase chromatography for peptides:

33 ?g/ml Met-Enkephalin, Let-Enkephalin, Angiotensin II, Physalaemin, Substance P Sample Preparation:

Filled 8 ml of buffer A in a 15 ml graduated plastic sample tube; Weighed appropriate amount of protein samples and placed them into this sample tube; Sealed the tube with cap and tumbled the tube gently until all the proteins dissolved; Added in more buffer solution until the 10 ml mark on the sample tube was reached.

A column was characterized by protein separation according to the following procedure: The column was attached to an Isco 2350 Two Pump System. Pump A contained 0.01 mol/l Tris.HCl buffer (Buffer A) and Pump B contained 1 mol/l NaCl in Buffer A (Buffer B). The mobile phases were degassed with helium purging for more than 20 minutes before use. The UV detector was set at 0.05 sensitivity and 280 nm wavelength for protein separation (214 nm for peptide separation). The volume of the sample injection was 20 micro liters. The column was first cleaned by 20 bed volume of Buffer B and conditioned by 15 bed volume of Buffer A at the 3 m/min for 4.6 mm I.D. column (10 ml/min for 10 mm I.D. column). The separation was achieved by a gradient from 0 to 50% Buffer B for 20 bed volume at the flow rate of 3 ml/min for 4.6 mm I.D. column and 10 ml/min for 10 mm I.D. column.

1b. LC Characterization Method 2: Binding Capacity Measurement

The binding capacity of an ion exchange column was measured by frontal analysis. The column was cleaned with 20 bed volume of Buffer B and conditioned with 15 bed volume of Buffer A. This columns was saturated with the sample protein by pumping 5 mg/ml BSA or lysozyme solution (BSA for anion exchanger and reversed phase, and lysozyme for cation exchanger) in Buffer A through the column until no further increase of the absorbance of the eluent, followed by cleaning the non-adsorbed proteins with 100% Buffer A. The protein bound to the columns was eluted by a gradient from 0 to 50% Buffer B for 20 bed volume. The eluted protein was collected in a sample vial and the protein concentration was determined by UV spectrometer at 280 nm. The total binding capacity of the column was calculated by multiplying the concentration of collected protein with the volume of collection.

1c. LC Characterization Method 3: Hydrophobic Interaction Chromatography

This column was characterized for hydrophobic interaction chromatography of proteins. A mixture of proteins containing Ribonuclease, Cytochrome C, Lysozyme, Bovine Serum Albumin and Carbonic Anhydrase (1, 0.3, 0.2, 1 and 0.5 mg/ml in 0.01 M Tris.HCl buffer solution at pH 7.0.) was separated by a 15 minute gradient of 0.5 moldi NaCl in 0.01 mol/I Tris.HCl buffer (pH 7.6) to the same buffer at the flow rate of 1 ml/min.

1d. LC Characterization Method 4: Polymer Molecular Weight Determination by Precipitation-Redissolution Chromatography Characterization method 6 was used for polymer molecular weight determination using Precipitation/Redissolution Chromatography. Seven polymerstandards(Mp: 12,900, 20,650, 34,500, 50,400, 96,000, 214,500, 982,000) were separated by a 6 minute gradient from 15% to 80% THF in methanol at the flow rate of 2.6 ml/min. The polymer standards were dissolved in 50% THF in methanol with the total concentration of 56 mg/ml. The injection volume was 20 Fl.

1e. LC Separation of Nucleotides

A sample of Pd(A)$_{12-18}$ (2.4 mg/ml in water) was separated by a gradient from 30% to 60% Buffer B in Buffer A (A=20% acetonitrile and 80% 20 mmol/l sodium phosphate; B=1 mol/l NaCl in A) at the flow rate of 1 ml/min.

1f. LC Separation of Nucleotides with Anion Exchanger

A sample of AMP, ADP and ATP (0.4, 0.8, 0.8 mg/ml in water respectively) was separated in a gradient of 0 to 50% Buffer B in Buffer A as specified in LC Characterization Method 1.

Numbered Examples

Example 1

A polymerization solution was prepared as following: Weighed 1.2 g of glycidyl methacrylate (GMA), 0.80 g of ethylene dimethacrylate (EDMA) (polymerization mixture 1) and 0.02 g of 2,2=-azobisisobutyronitrile (AIBN) into a 20 ml sample vial and shook the mixture gently until it became a homogeneous solution; Weighed 2.55 g of cyclohexanol (CHOH) and 0.45 g of dodecanol (DODOH) into this solution and shook it until it is homogeneous. The polymerization mixture was degassed as in Degassing Procedure.

An empty stainless steel column (4.6 mm inner i.d. and 50 mm length), one end of which was sealed by a pressuring device shown in FIG. 4, was filled with this solution until the column is full. A PEEK-plug contained in the stainless steel screw cap, which was the original cap for the column shown in the same figure, was used to seal the other end of the column. The device of FIG. 3 was connected to a syringe pump. Water was used as the medium to generate the pressure of 120 psi. No air was inside the column. This column was placed into a water bath upright at 60?C and kept for 20 hours. After polymerization, the column was taken out of the water bath and cooled to room temperature.

The device of FIG. 3 was detached from the syringe pump after the pressure was released. The device of FIG. 3 was opened and carefully removed from the column. White polymer extended outside the column. The length of the polymer was found to be about 2 mm shorter than the height of the polymerization solution inside the column and the device of FIG. 3. This extended part of polymer was removed by razor blade. The column was then fitted with the original HPLC column fittings. The column was connected to a HPLC pump and washed with acetonitrile at 0.5 ml/min for 20 minutes at 45?C.

The fillings from one end of the column were detached and the media was pressed out of the column by pumping 10 m/min acetonitrile into the column through the other end. The wall surface of the polymer media was found to be smooth. The top of polymer was flat.

Comparative Versions of Example 1

A polymerization solution was prepared as following: Weighed 1.2 g of glycidyl methacrylate (GMA), 0.80 g of ethylene dimethacrylate (EDMA) (polymerization mixture 1) and 0.02 g of 2,2=-azobisisobutyronitrile (AIBN) into a 20 ml sample vial and shook the mixture gently until it became a homogeneous solution; Weighed 2.55 g of cyclohexanol (CHOH) and 0.45 g of dodecanol (DODOH) into this solution and shook it until it is homogeneous. The polymerization solution was degassed with the above Degassing Procedure.

An empty stainless steel column (4.6 mm inner i.d. and 50 mm length), one end of which was sealed by a PEEK-plug contained in the stainless steel screw cap which was the original cap for the column. This column was filled with the above solution until it was full. A PEEK-plug was carefully placed on the top of column and sealed with another screw cap. No air should be kept inside the column. This column was placed into a water bath upright at 60?C and kept for 20 hours. After polymerization, the column was taken out of the water bath and cooled to room temperature.

The PEEK-plugs were detached and white polymer was observed in the column. The column was then fitted with the original HPLC column fittings. The column was connected to a HPLC pump and washed with tetrahydrofuran (THF) at 0.5 ml/min for 20 minutes.

The fitting from one end of the column was detached and the media was pressed out of the column by pumping 10 ml/min acetonitrile (ACN) into the column through the other end. The wall surface of the media was found to contain many small irregular dents.

Other columns were prepared using different monomers. Irregular voids were found on the wall surface of the polymer rods. Pictures of two of these rods and one rod made under pressure were taken and shown in the FIG. 7.

Alternative Versions of Example 1

The procedure of Example 1 was followed except that different polymerization mixtures were used having different proportions and combinations of the functional monomers and crosslinkers. The functional monomers used includes glycidyl methacrylate (GMA), 2-hydroethyl methacrylate (HEMA), methyl methacrylate (MMA), 2-(acryloyloxy-ethyl)trimethylammonium methyl sulfate (ATMS), acrylic acid (AA), 2-Acrylamido-2-methyl-1-propanesulfonic acid (AMPS), stearyl methacrylate (SMA), lauryl methacrylate (LMA), butyl methacrylate (BMA), styrene (ST) and 4-ethylstyrene (EST). The crosslinking monomers (crosslinkers) used include ethyleneglycol dimethacrylate (EDMA), divinyle benzene (DVB). Different proportions of functional monomers, crosslinking monomers and porogens were used. The porogens includes different alcohols such as cyclohexanol, dodecanol, decanol, 1-hexadecanol, butanol, propanol, iso-propanol, ethanol, methanol, 1,4-butanediol and others such as toluene, N,N-Dimethyl acetamide, acetonitrile, 1,2-dimethoxyethane, 1,2-dichloroethane, dimethyl phthalate, 2,2,4-trimethylpentane, 1,4-dixane, 2-methyloxyethanol, 1,4-butanediol, m-xylene, diisobutyl phthalate, tetra(ethylene glycol) dimethyl ether, tetra(ethylene glycol), poly(propylene glycol) (F.W. 1000), poly(propylene glycol) monobutyl ether (F.W. 340, 1000, 2500). The initiators used included 2,2-prime-azobisobutyronitrile (AIBN) and benzoyl peroxide.

For each of the combinations of monomers and porogens, columns were prepared, examined and characterized.

Several columns were made with each polymerization mixtures under several pressure conditions. The pressure conditions include: (1) the column opened to the atmosphere during polymerization; (2) the column sealed during polymerization; (3) pressure being applied to the column with gas applied directly to the polymerization mixture using nitrogen as the gas; (4) each of rubber, plastic and metal pistons being in contact with the polymerization mixture and applying pressure from either a spring, hydraulic pressure, gas pressure or by threading the piston downwardly using the device described above or the modified device when the mechanical force such as spring was used.

The results were: (1) for cases when atmospheric pressure was present there were discontinuities on the surface of a high percentage of columns. Column efficiencies and resolutions were not reproducible; (2) for pressure conditions in which the column was sealed, a higher percentage of columns had discontinuities on the surface, column efficiencies and resolutions were not reproducible; (3) for columns in which gas pressure was applied, the top end surfaces of the columns were soft and irregular, and the wall surfaces were smooth. The separation chromatograms had better reproducibility. The elution peaks are sharper than when pressure was not applied; (4) reproducibility was very high when pistons were used and the resolution was better than all the above methods used.

Example 2

A polymerization solution was prepared as Example 1 with the following polymerization solution: 2.0 g GMA, 2.5 g 2-(acryloyloxyethyl)trimethylammonium methyl sulfate (ATMS, 80%), 6.0 g EDMA, 7.5 g 1,4-butariediol, 6.75 g propanol, 0.75 g water and 0.1 g AIBN.

An empty glass column (10 mm inner i.d. and 100 mm length), one end of which was sealed by a pressuring device shown in FIG. 4, was filled with this solution until the column is full. A TEFLON-plug contained in the PEEK screw cap shown in the same figure, was used to seal the other end of the column. The device of FIG. 4 was connected to a syringe pump. No air was inside the column. This column was placed into a water bath upright at 60?C and kept for 15 minutes. Then the column was pressurized to 120 psi by syringe pump using water as the medium, and kept for 20 hours. After polymerization, the column was taken out of the water bath and cooled to room temperature.

The device of FIG. 4 was detached from the syringe pump after the pressure was released. The device of FIG. 4 was opened and carefully removed from the column. It was found that the height of the polymer rod was 4 mm shorter than the height of the polymerization solution inside the column. The column was then fitted with the original HPLC column fittings. The column was connected to a HPLC pump and washed with acetonitrile at 2 ml/min for 20 minutes at 45?C.

The fittings from one end of the column were detached and the media was pressed out of the column by pumping 10 ml/min acetonitrile into the column through the other end. The wall surface of the polymer media was found to be smooth. The top of polymer was flat.

Alternative Versions of Example 2

The method of Example 2 was followed with the change of pressures and methods of applying the pressures. Different constant pressures were used during polymerization. The pressures used include 80 psi, 150 psi, 180 psi, 200 psi, 240 psi and 300 psi. The back pressures of these columns are different. The Scanning Electron Microscopy examination of the polymer structure revealed that the particle sizes of these polymers are also different.

A step gradient of pressure was applied to the polymerization mixture during polymerization. The gradient is as following: 4 psi/min increase from 10 psi for 5 min, 2 psi/min increase for 10 min, 1 psi/min increase for 20 min, 0.8 psi/min increase for 30 min and then increase the pressure to 180 psi within an hour. The final pressure of 180 psi was kept for 20 hours during polymerization.

A linear gradient from 15 psi to 180 psi for 2 hours was used to pressurize the reaction at early stage of polymerization. 180 psi was kept for another 18 hours during the rest of polymerization.

All these columns were modified by pumping in 5 ml solution of 0.45 g/ml trimethylamine hydrochloride in trimethylamine aqueous solution (50% volume). The columns were sealed and heated in a water bath at 40° C. for 3 hours. They were washed with 20 bed volume of water right after modification. These columns were subjected to Bed Stabilization and Conditioning as described above. They were characterized as above LC Characterization Method for ion exchangers. The back pressures, particle sizes and separation resolutions of these columns all varied with the pressurization methods.

Different polymerization time was also used. A column was prepared as in example 2 except that the polymerization time was 44 hours instead of 20 hours.

Ten columns were prepared in parallel using a ten channel manifold with only one pressure source. The columns prepared have better reproducibility than individual preparation process.

The polymer morphologies and the internal structures of the particles were examined with Scanning Electron Microscopy (SEM). It was found that the internal structures of these particles are non-porous instead of porous in the other monolithic media known in the art.

Example 3

Two columns were prepared as in Example 1 and 2 with the following solution: 17.5 g DVB, 19.8 g tetra(ethylene glycol), 10.2 g tetra(ethylene glycol) dimethyl ether, and 0.18 g AIBN. After wash with acetonitrile, the column was further washed with 20 bed volume of water at the flow rate of 16 ml/min. The manually positioned pistons in both ends were compressed into the column. This column was then washed with acetonitrile containing 0.15% trifluoroacetic acid and characterized by LC characterization method 1a and 1b. The resolutions of these columns for both protein and peptide separation were improved greatly over the columns made in the Comparative Examples. The capacities were more than 5 times higher. The back pressures of these columns were low. High resolutions were achieved with the mobile phase gradient starting from 100% water containing 0.15% TFA. No wall effect was found in these columns. The proteins and peptides pre-eluted out of the column in the columns from Comparative Examples due to wall effect in aqueous phase.

Comparative Versions of Example 3

A polymerization solution was prepared as Comparative Example of Example 1 with the following reagents: 3 ml styrene, 2 ml divinylbenzene, 7.5 ml dodecanol and 0.5 g AIBN. The column was characterized with reversed-phase protein and peptide separation described as LC Characterization 1a and 1b.

Alternative Versions of Example 3

Example 3 was followed with different combinations of porogens, different monomers containing different carbon chain length, different amount of total monomer contents, different initiators and different shrinkage solvents.

The porogens used includes: alcohols containing C1 to C12, N,N-Dimethyl acetamide, acetonitrile, 1,2-dimethoxyethane, 1,2-dichloroethane, dimethyl phthalate, 2,2,4-trimethylpentane, 1,4-dixane, 2-methyloxyethanol, 1,4-butanediol, toluene, m-xylene, diisobutyl phthalate, tetra(ethylene glycol) dimethyl ether, tetra(ethylene glycol), poly(propylene glycol) (F.W. 1000), poly(propylene glycol) monobutyl ether (F.W. 340, 1000, 2500). The combination of some of these solvents led to high resolution columns as well. The alcohols and their combinations can provide large channels for mobile phase to flow through with low back pressure while providing high resolutions. The resolution can be finely tuned with other good solvents as well.

The monomers used include butyl methacrylate and stearyl methacrylate with the above combination of porogens. One column was prepared with the following polymerization solution: 7 g SMA, 10.5 g DVB, 19.5 g ethanol, 13.0 g butanol and 0.18 g AIBN. Another column was prepared with the following polymerization solution: 7 g lauryl methacrylate (LMA), 1 g HEMA, 12 g EDMA, 30 g dodecanol and 0.2 g AIBN. Another column was prepared with the following polymerization solution: 7 g butyl methacrylate (BMA), 1 g HEMA, 12 g EDMA, 3 g water, 16.5 g propanol, 10.5 g 1,4-butanediol and 0.2 g AIBN. The combinations of these monomers containing different carbon chain length provide different hydrophobicity and interaction, which offer high resolution and recovery toward samples with different hydrophobicity and characteristics. For example, the butyl methacrylate based media was used for more hydrophobic protein separation and the stearyl methacrylate based media can be used for more hydrophilic protein, peptide or oligonuleotide separations.

Different ratios of monomer to crosslinker were also used to tune the selectivity and resolution. One column was prepared with the following polymerization solution: 1.05 g SMA, 0.7 g DVB, 3.25 g ethanol and 0.018 g AIBN.

Different initiator was also used. A column was prepared with the following polymerization solution: 10 ml divinylbenzene (80% purity), 30 ml dodecanol, 10 ml styrene and 0.20 g benzoyl peroxide.

Different polymerization time was also used. A column was prepared as in example 3 except that the polymerization time was 44 hours instead of 20 hours.

Different polar solvents were used to shrink the polymer before compression. A column was prepared as Example 3 and washed with 20 bed volume of 1 M NaCl after water wash. Manually positioned pistons were compressed into the column after the salt wash. The column show no wall effect when 0.1 M $NaH_2PO_4$ (pH 4.0) was used as the starting mobile phase.

These experiments were repeated with different washing solutions and different catalysts with and without pressure in the presence of an aqueous solution after the plug was polymerized as well as with different pressures. In each case, when no pressure was applied, there were discontinuities in the outer wall, and upon characterization, there was a lack of repeatability and the peaks of the chromatograms were less pronounced when no pressure was applied after swelling by washing with an aqueous solution.

Tests have been run at a plurality of pressures both low pressures and high pressures including 60 psi (pounds per square inch) and 120 psi and 600 psi with good results. It is believed that the amount of pressure needed will vary with the diameter of the column and the particular polymerization mixture but satisfactory results can be obtained at a very low pressure in all cases. The upper limit on pressure is the strength of the column walls and fittings.

The amount of pressure also affects the pore size so that the pressure should be selected together with desired pore size, distribution and reproducibility of the column.

Example 4

A column was prepared as Example 2 with the following solution: Nine g of glycidyl methacrylate, 9 g of ethylene dimethacrylate, 0.18 g, 21.6 g of cyclohexanol and 6.3 g of dodecanol. The length of the polymer was found to be about 7 mm shorter than the height of the polymerization solution inside the column. The column was then fitted with the original column fittings. The column was connected to a HPLC pump and washed with acetonitrile at 4 ml/min for 20 minutes at 45?C. The column was further modified as following:

A solution containing 570 mg trimethylamine hydrochloride, 24 ml diethylamine and 6 ml water was pumped into these columns at the flow rate of 2 ml/min for 18 minutes. These columns were then placed in a water bath at 30?C for 3 hour. Each column was washed with 100 ml water. The columns were further washed with 0.01 mol Tris.HCl buffer at pH 7.6 at 4 ml/min for 30 minutes. The column was stabilized and conditioned by STABILIZING AND CONDITIONING METHODS. The pistons from original column fittings were compressed in completely after the wash. The column back pressures were about 360 psi at 10 ml/min in this buffer. The column was characterized as LC Characterization Method described above.

Example 5

A polymerization solution was prepared by mixing 1 g styrene, 1 g divinylbenzene (DVB) (80% divinyl benzene and 20% ethylstyrene (EST)), 3 g dodecanol and 0.02 g AIBN.

This solution was degassed by $N_2$ purging for 20 minutes and filled into a stainless steel column (50×4.6 mm i.d.), one end of which was sealed with a PEEK plug inside the screw cap from the column fittings. The other end of the column was sealed with another PEEK plug. It was polymerized at 70 degrees C. in a water bath for 24 hours. This column was fitted with the original column fittings and washed with THF at the flow rate of 1 ml/min for 10 minutes before it was used for separation of proteins. The back pressure of this column was about 230 psi at the flow rate of 10 ml/min. The compression of the polymer at 10 ml/min of acetonitrile was about 2.9 mm. This column was used for reversed phase protein and peptide separation as LC Characterization Method 1a and 1b.

Alternative Versions of Example 5

Another column was prepared as in example 5 but with higher total monomer contents. The polymerization solution contained 1.2 g styrene, 1.2 g divinylbenzene, and 2.6 g dodecanol and 0.024 g AIBN. The back pressure of the column was 220 psi at 10 ml/min acetonitrile and the compression of the polymer was only 0.9 mm. The higher total monomer content makes the column less compressible.

Columns of different diameters including 22 mm, 1 5 mm, 10 mm, 8 mm, 2.1 mm, 1 mm, 542 ?m, and 320 ?m were prepared as in Example 4. Shorter columns with the size of 10 mm×2.1 mm i.d. were also prepared. These columns were characterized with reversed phase protein separation by LC Characterization Method but at the same flow velocity corresponding to the diameters of the columns. The in situ polymerization method is applicable in columns with different diameters. It is especially useful for smaller diameter columns or micro fluid channels since there is no other packing step involved.

Example 6

Another column was prepared according to Example 5. This column was fitted with the original column fittings containing a piston and washed with acetonitrile at the flow rate of 1 ml/min for 10 minutes. The column was further washed with water for 10 minutes. The pistons in both ends were compressed into the column. This column was characterized by LC Characterization Method. The compression of the polymer in water by piston and held by this piston after compression avoid the wall effect resulted from the shrinkage of polymer in water.

Alternative Versions of Example 6

Another column was prepared as Example 5 with the following solution: 1.8 g divinylbenzene, 0.2 g of styrene, 2.3375 g dodecanol, 0.6625 g toulene, 0.02 g of AIBN and 3.0 g of dodecanol. All the reagents were degassed by vacuum using aspirator for five minutes, followed by purging with Helium for 20 minutes, before weighing. The polymerization solution was filled into a stainless steel column (50×4.6 mm i.d.), one end of which was sealed by PEEK-plug contained in the screw cap. The other end of the column was sealed with another PEEK plug. It was polymerized at 66 degrees C. in a water bath for 24 hours. This column was fitted with the original column fittings containing a piston and washed with acetonitrile at the flow rate of 1 ml/min for 10 minutes. The column was further washed with water for 10 minutes. The pistons in both ends were compressed into the column. This column was characterized by the LC Characterization Method. The higher content of crosslinker improved the compacity. This version of a column has more than 3 times higher capacity than the some other columns prepared in accordance with Example 6.

Another column was prepared with the following polymerization solution: 10 ml divinylbenzene (80% purity), 10 ml styrene and 0.20 g benzoyl peroxide.

This polymerization solution was purged by $N_2$ for 20 minutes. It was filled into a stainless steel column (50×4.6 mm i.d.), one end of which was sealed by PEEK-plug contained in the screw cap. The other end of the column was sealed with another PEEK plug. It was polymerized at 70?C in a water bath for 24 hours. This column was fitted with the original column fittings and washed with tetrahydrofuran at the flow rate of 1 ml/min for 10 minutes. It was characterized by reversed phase protein and peptide separation as described in LC Characterization Method. Different initiators such as benzoyl is also effective in making the monolithic media.

A stainless column of smaller size (50×2.1 mm i.d.) and a PEEK column (50×4.6 mm i.d.) were prepared and characterized 8 as above example.

Example 7

A column was prepared as in Example 6 with the following solution: divinylbenzene, 0.2 g of hydroxylethylmethacrylate and 0.02 g of AIBN. It was polymerized at 70?C in a water bath for 24 hours. This column was fitted with the original column fittings containing pistons. It was washed with acetonitrile at the flow rate of 1 ml/min for 10 minutes, and further washed with water and 0.5 mol/l NaCl in 0.01 mol/l Tris.HCl buffer (pH 7.6). This column was characterized by reversed-phase protein separation as in LC Characterization Method.

Alternative Versions of Example 7

A column was prepared and characterized according to the above procedure except the weight of hydroxylethylmethacrylate and divinylbenzene were changed to 0.4 g and 1.6 g.

Another column was prepared and characterized according to the above procedure except the weight of hydroxylethylmethacrylate and divinylbenzene were changed to 1 g and 1 g.

Another column was prepared as in Example 7 with the following polymerization solution: −1.8 g divinylbenzene, 0.16 g styrene, 0.04 g of hydroxylethylmethacrylate, and 0.02 g of AIBN and This column was fitted with the original column fittings containing pistons after polymerization. It was washed with acetonitrile at the flow rate of 1 ml/min for 10 minutes, and further washed with water and 0.5 mol/l NaCl in 0.01 mol/l Tris.HCl buffer (pH 7.6). This column was compressed with pistons and characterized by reversed phase separations of proteins and peptides as in LC Characterization Method.

Example 8

An empty syringe barrel (70×12 mm i.d. Redisep barrel for Combiflash chromatography from Isco, Inc., 4700 Superior Street, Lincoln, Nebr. 68504) was sealed at one end and filled with the following polymerization solution: 1.6 g hydroxylethyl methacrylate, 6.4 g divinylbenzene, 89 mg AIBN, 12 g dodecanol after degassing with $N_2$ for 20 minutes. The tip of the barrel was sealed with a blocked needle. This barrel was heated in a water bath at 70?C for 24 hours. It was connected to a HPLC pump and washed with THF at the flow rate of 1 ml/min for 30 minutes. It was then used for both normal phase and reversed phase separation of phenolic compounds.

Example 9

A polymerization solution was prepared as following: Weighed 1 g of hydroxyethyl methacrylate, 1 g of ethylene dimethacrylate and 0.02 g of AIBN into a 20 ml sample vial and shook the mixture gently until it became a homogeneous solution; Weighed 1 g of cyclohexanol and 2 g of dodecanol into this solution and shook it until it is homogeneous. All the reagents were degassed by vacuum using aspirator for five minutes, followed by purging with Helium for 20 minutes, before weighing.

An empty stainless steel column (4.6 mm inner i.d. and 50 mm length), one end of which was sealed by a device of FIG. 4 was filled with this solution until the column is full. A PEEK-plug contained in the stainless steel screw cap, which was the original cap for the column, was used to seal the other end of the column. The device of FIG. 4 was connected to a syringe pump. Water was used as the medium to generate the pressure of 120 psi. No air should be kept inside the column. This column was placed into a water bath upright at 60?C and kept for 20 hours. After polymerization, the column was taken out of the water bath and cooled to room temperature. The column was connected to a HPLC pump and washed with dry THF (dried by molecular sieve) at 0.5 ml/min for 20 minutes. The column was used for Normal Phase separation of drugs.

Alternative Versions of Example 9

A column was prepared as in Example 9 with the following polymerization solution: 0.5 g GMA, 0.5 g HEMA, 1 g EDMA, 1.8 g cyclohexanol, 1.2 g dodecanol, 0.02 g AIBN.

The columns were washed with water after THF wash at the flow rate of 0.5 ml/min for 20 minutes. 10 ml of 1.0 mol/l sulfuric acid in water was pumped through the columns. The columns were sealed with column plugs and placed into a water bath at 80?C for 3 hours. They were washed with 20 ml water after the modification reaction and further washed with dry THF before characterization with Normal Phase separation.

Another column was prepared with the following polymerization solution: 1 g glycidyl methacrylate, 1 g ethylene dimethacrylate, 2.4 g cyclohexanol, 0.6 g dodecanol, 0.02 g AIBN.

The columns were washed with water after THF wash at the flow rate of 0.5 ml/min for 20 minutes. 10 ml of 1.0 mol/l sulfuric acid in water was pumped through the columns. The columns were sealed with column plugs and placed into a water bath at 80?C for 3 hours. They were washed with 20 ml water after the modification reaction and further washed with dry THF before characterization with Normal Phase separation.

Example 10

A stainless steel column (50×4.6 mm i.d.) was prepared as in Example 3 with the following polymerization solution contained 0.7 g lauryl methacrylate (LMA), 0.1 g HEMA, 1.2 g EDMA, 3 g dodecanol and 0.02 g AIBN.

Alternative Versions of Example 10

A column was prepared with the following polymerization solution contained 0.8 g lauryl methacrylate (LMA), 1.2 g EDMA, 3 g dodecanol and 0.02 g AIBN. Another column was prepared with the following polymerization solution containing 0.175 g stearyl methacrylate (SMA), 1.575 g DVB (80% pure), 3.25 g 1-hexadecanol and 0.018 mg AIBN to form a mixture with a ratio SMA/DVB=10/90. Another column was prepared with the following polymerization solution containing 0.7 g SMA, 1.05 g DVB, 3.25 g octanol and 0.018 g AIBN to provide a ratio of 40/60 SMA/DVB.

Another column was prepared with the following polymerization solution containing 1.05 g SMA, 0.7 g DVB, 3.25 g ethanol and 0.018 g AIBN to provide a ratio of 60/40 SMA/DVB.

Another column was prepared with the following polymerization solution containing 0.7 SMA, 1.05 g DVB, 1.95 g ethanol, 1.30 g butanol and 0.018 g AIBN to provide a ratio of 40/60 SMA/DVB.

Other columns were prepared as above using tetradecanol, decanol, octanol, hexanol, butanol, propanol, ethanol and methanol and their combinations as porogenic solvents.

Another column was prepared as above with the following polymerization solution: 0.7 SMA, 1.05 g DVB, 2.925 g ethanol, 0.33 g methanol, 0.33 g isopropanol and 0.018 g AIBN to provide ratio of 40/60 SMA/DVB.

Another column was prepared as above with the following polymerization solution: 0.7 SMA, 1.05 g DVB, 2.6 g ethanol, 0.33 g methanol, 0.33 g propanol, 0.33 g butanol and 0.018 g AIBN to provide a ratio of 40/60 SMA/DVB.

Another column was prepared as above with the following polymerization solution: 0.7 SMA, 1.05 g DVB, 2.762 g ethanol, 0.33 g methanol, 0.33 g propanol, 0.33 g butanol, 0.33 g hexanol and 0.018 g AIBN to provide a ratio of 40/60 SMA/DVB.

Another column was prepared as above with the following polymerization solution: 0.7 SMA, 1.05 g DVB, 2.435 g ethanol, 0.33 g methanol, 0.33 g propanol, 0.33 g butanol, 0.33 g hexanol, 0.33 g octanol and 0.01 8 g AIBN to provide a ratio of 40/60 SMA/DVB.

Another column was prepared as above with the following polymerization solution: 1.05 g DVB, 3.08 g ethanol, 0.0.16 g ethyl ester and 0.018 g AIBN. This column was used for peptide separation as in Example 10, to provide a ratio of 40/60 SMA/DVB.

Another column was prepared as above with the following polymerization solution: 1.75 g DVB, 3.25 g dodecanol and 0.018 g AIBN. This column was used for peptide separation as in the first version of example 10. A series of columns with alcohols containing C1 to C12 were prepared as above and characterized with peptide separation.

A series of columns were prepared as above using the following porogens instead of dodecanol: iso-propanol, N,N-Dimethyl acetamide, acetonitrile, 1,2-dimethoxyethane, 1,2-dichloroethane, dimethyl phthalate, 2,2,4-trimethylpentane, 1,4-dixane, 2-methyloxyethanol, 1,4-butanediol, toluene, m-xylene, diisobutyl phthalate, tetra(ethylene glycol) dimethyl ether, tetra(ethylene glycol), poly(propylene glycol) (F.W. 1000), poly(propylene glycol) monobutyl ether (F.W. 340, 1000, 2500).

Another column was prepared as above with the following polymerization solution: 1.75 g DVB, 2.925 g isopropanol, 0.325 g 1,4-butanediol and 0.018 g AIBN. Another column was prepared as above with the following polymerization solution: 1.75 g DVB, 2.275 g isopropanol, 0.975 g 2-methyloxyethanol and 0.018 g AIBN.

Another column was prepared as above with the following polymerization solution: 1.75 g DVB, 2.60 g isopropanol, 0.65 dimethyl phthalate and 0.018 g AIBN. Another column was prepared as above with the following polymerization solution: 1.75 g DVB, 2.7 g tetraethylene glycol, 0.3 g diethylene glycol and 0.018 g AIBN.

Another column was prepared as above with the following polymerization solution: 1.75 g DVB, 2.7 g tetra(ethylene glycol), 0.3 g glycerol and 0.018 g AIBN. Another column was prepared as above with the following polymerization solution: 1.75 g DVB, 1.98 g tetra(ethylene glycol), 1.02 g tetra(ethylene glycol) dimethyl ether, and 0.018 g AIBN.

Another column was prepared as above with the following polymerization solution: 1.75 g DVB, 1.98 g tetra(ethylene glycol), 1.02 g tetra(ethylene glycol) dimethyl ether, and 0.018 g AIBN.

Example 11

A column (50×4.6 mm i.d. stainless steel, which is 50 mm length and 4.6 mm inner i.d.) was prepared as Example 1 with the following polymerization solution containing 1 g methyl methacrylate (MMA), 1 g EDMA, 1.8 g cyclohexanol, 1.2 g dodecanol and 0.02 g AIBN It was connected to a HPLC pump and washed with THF and water at 0.5 ml/min for 20 minutes in sequence.

This column was subjected to a hydrolysis reaction as following: 2 ml 6 mol/l NaOH was pumped through the column at the flow rate of 0.5 ml/min; The column was sealed by two column plugs and placed in a water bath at 80?C for 1 hour. It was washed with 20 ml water at the flow rate of 0.5 ml/min and characterized with protein separation and binding capacity measurement described in LC Characterization Method.

Alternative Versions of Example 11

A column was prepared as Example 11 with the following polymerization solution: 0.1 g acrylic acid (M), 0.9 g methyl methacrylate (MMA), 1 g EDMA, 3 g dodecanol and 0.02 g AIBN. The capacity of the column was measured before and after hydrolysis. The capacity before hydrolysis was about 10 mg lysozyme per ml column volume. It was about 30 mg after hydrolysis.

Another column was prepared as Example 11 with the following polymerization solution: 0.2 g AA, 0.8 g MMA, 1 g EDMA, 3 g dodecanol and 0.02 g AIBN. The capacity of the column was measured as in characterization method 11. The capacity before hydrolysis was about 27 mg lysozyme per ml column volume. It was about 50 mg after hydrolysis.

Another column was prepared as Example 11 with the following polymerization solution: 0.3 g AA, 0.7 g MMA, 1 g EDMA, 3 g dodecanol and 0.02 g AIBN. The capacity of the column was measured before and after hydrolysis The capacity before hydrolysis was about 43 mg lysozyme per ml column volume. The capacity was more than 60 mg after hydrolysis.

Another column was prepared as above with the following polymerization solution: 0.4 g AA, 0.6 g MMA, 1 g EDMA, 3 g dodecanol and 0.02 g AIBN.

Another column was prepared as above with the following polymerization solution: 0.1 g M, 0.9 g tert-butyl acrylate, 1 g EDMA, 3 g dodecanol and 0.02 g AIBN.

Another column was prepared as above with the following polymerization solution: 0.3 g M, 0.3 g MMA, 1.4 g EDMA, 3 g dodecanol and 0.02 g AIBN.

Another column was prepared as above with the following polymerization solution: 0.2 g M, 0.7 g MMA, 0.1 g HEMA, 1 g EDMA, 2.85 g dodecanol, 0.15 g cyclohexanol and 0.02 g AIBN. Another column was prepared as above with the following polymerization solution: 0.4 g M, 1.6 g DVB, 3 g dodecanol and 0.02 g AIBN.

Another column was prepared as above with the following polymerization solution: 1 g GMA, 1 g EDMA, 2.4 g cyclohexanol, 0.6 g dodecanol, 0.02 g AIBN. This column was subjected to an acid-catalyzed ring opening reaction as in a Alternative versions of Example 9 before base-catalyzed hydrolysis reaction as in Example 11.

Another column was prepared as above with the following polymerization solution: 0.5 g GMA, 0.5 g HEMA, 1 g EDMA, 1.8 g cyclohexanol, 1.2 g dodecanol, 0.02 g AIBN.

Another column was prepared as above with the following polymerization solution: 0.2 g M, 0.6 g MMA, 0.2 g GMA, 1 g EDMA, 3 g dodecanol and 0.02 g AIBN. This column was subjected to an acid-catalyzed ring opening reaction before base-catalyzed hydrolysis reaction as above. It was further hydrolyzed with the following solution: 0.25M Sodium chloroacetate in 5M NaOH at 60° C. for 6 hours.

Another column was prepared as above with the following polymerization solution: 0.2 g M, 0.5 g MMA, 0.1 g GMA, 1.2 g EDMA, 2.55 g dodecanol, 0.45 g cyclohexanol and 0.02 g AIBN. It was hydrolyzed by 0.25M Sodium chloroacetate in 5M NaOH at 60?C for 6 hours.

All these columns were subjected to Bed Stabilization and Compression Method and characterized with protein separation and binding capacity measurement as in LC Characterization Method described above.

Example 12

A column (PEEK-lined stainless steel, 50×4.6 mm ID) was prepared as Example 1 with the following polymerization solution: 3 g GMA, 3 g EDMA, 6.9 g cyclohexanol, 2.1 g dodecanol and 0.06 g AIBN.

This column was first modified with ring-opening reaction under acidic condition. Five bed volume of the solution of 0.5 M sulfuric acid in water was pumped through the columns. The column was sealed and heated in a water bath at 50° C. for 4 hours. It was washed with 20 bed volume of water after modification.

This column was further modified with a etherification reaction. Five bed volume of a solution containing 20 g sodium chloroacetate, 20 g NaOH and 64 ml water was pumped through the column. The column was sealed with column plugs and heated in a water bath at 60° C. for 2.5 hours. It was washed with water, stabilized and conditioned as Stabilization and Conditioning Methods. This column was characterized as in LC Characterization Method.

Alternative Versions of Example 12

The Example 12 was followed with different modification methods.

A column prepared as in Example 12 was modified by a ring-opening reaction with the following solution: 6 mol/l glycolic acid and 0.5 M TFI in water for 3 hours.

Another column was modified with the above ring-opening reaction and hydrolysis reaction in 5 M NaOH solution at 60° C. for 2.5 hours.

Another column was first modified by ring-opening reaction with the following solution containing 40 g glycolic acid, 60 ml 0.5 M trifuoroacetic acid (TFA) for 2 hours. It was further modified with a solution containing 20 g ClCH$_2$COONa and 60 ml 5M NaOH for 3 hours.

Example 13

Thirty columns were prepared as Example 2 with the following solution: 12 g AA, 30 g MMA, 6 g GMA, 72 g EDMA, 27 g cyclohexanol, 153 g dodecanol and 1.2 g AIBN. These columns were prepared by parallel synthesis at the same time using three manifolds connecting to one syringe pump to obtain 120 psi pressure during polymerization. After polymerization, polymers were pushed out of the columns by a syringe piston (about 9 mm i.d.) for the following uses.

One polymer rod from above was trimmed to be smaller with the diameter about 8 mm. It was cut to 1 cm thick discs. These discs were used as fillers for a second stage polymerization to prepare another column. 1.8 ml solution was filled into a glass column (100×10 mm i.d.), one end of which was sealed by pressurization device shown in FIG. 3. Six polymer discs were filled into the column one by one. All these discs should be covered by the solution. A Teflon stopper was used to seal the other end of the column. This pressurization device was connected to a syringe pump which was used to add 120 psi pressure to polymerization solution at constant pressure mode. The column was heated in a water bath at 60° C. for 20 hours. After polymerization, the column was taken out of the water bath. The pressurization device was detached from the syringe pump after the pressure was released. The pressurization device was opened and slowly removed from the column while the column is still warm. This column was washed with 20 bed volume of acetonitrile and water at the flow rate of 1 ml/min in sequence. It was stabilized and conditioned as in Stabilization and Conditioning Method. This column was modified with 0.25 mol/l Sodium chloroacetate in 5M NaOH at 60° C. for 6 hours. It was characterized as in LC Characterization method.

Alternative Examples of Example 13

Another column (100 mm×35 mm ID, glass) was prepared with the two stage polymerization method with the polymer rods as the fillers. This column was sealed with TEFLON plug in one end. The other end of the column was connected to N$_2$ tank. The polymerization was under 120psi for 20 hours at 60° C.

Example 14

Eight short polymer rods (10 mm×34 mm ID) were prepared with the following solution: 8 g acrylic acid, 20 g methyl methacrylate, 4 g glycidyl methacrylate, 48 g ethylene glycol dimethacrylate, 102 g dodecanol, 18 g cyclohexanol and 0.8 g AIBN. The polymer rods were prepared under 120 psi N$_2$ pressure. The rods were used as fillers for the preparation of a large diameter long column using the two stage polymerization method as in Example 12. A glass column (100 mm×35 mm ID) was filled with the short columns and the same polymerization as above. One end of the column was sealed with a TEFLON plug and the other end was connected with a N$_2$ tank. The polymerization was carried out under 120 psi pressure at 60° C. for 20 hours. The column was washed with 20 bed volume acetonitrile and water. It was subjected to hydrolysis reaction as following: 0.25M Sodium chloroacetate in 5M NaOH at 60?C for 6 hours. The column was characterized as LC Characterization Method described above.

Example 15

A column (PEEK-lined stainless steel, 50 mm×4.6 mm ID) was prepared as in Example 1 with the following solution: 4 g GMA, 4 g EDMA, 2.8 g dodecanol, 9.2 g cycohexnanol and 0.08 g AIBN.

This column was first hydrolyzed by 1 M $H_2SO_4$ solution at 40° C. for 3 hours. After hydrolysis, it was activated by pumping 5 bed volume of 5% sodium t-butoxide solution in DMSO through the column and heated in a water bath at 90° C. for 1 hour. Then it was modified with the solution containing 20% of the activation solution and 80% of butane sultone at 80° C. for 20 hours.

Alternative Versions of Example 15

A column was prepared as in Example 15 except that propane sultone was used instead of butane sultone.

Another column was prepared as in Example 15 except the modification and activation temperature was 120° C. instead of 90° C. in an oil bath.

Another column was prepared as in Example 15 with the following solution: 4 g HEMA, 4 g EDMA, 9.4 g dodecanol, 2.6 cyclohexanol and 0.08 g AIBN. It was modified as in Example 15.

Another column was prepared as in Example 1 with the following solution: 0.55 g GMA, 1.2 g EDMA, 0.25 g 2-Acrylamido-2-methyl-1-propanesulfonic acid (AMPS), 0.48 g NaOH, 0.5 g water, 1.86 g propanol, 0.64 g butanediol and 0.02 g AIBN.

Another column was prepared by direct copolymerization of AMPS as above but was further modified with the modification method described in Example 15.

All these columns were characterized with the strong cation exchange protein separation and binding capacity measurement described in LC Characterization Method.

Example 16

A column was prepared as Example 1 with the following polymerization solution: 45 ml tetramethoxysilane, 100 ml of 0.01 mol/l aqueous acetic acid, 9 g urea and 11.5 g poly(ethylene oxide) (MW 10000). This solution was prepared by stirring this mixture in ice bath for 30 minutes. The polymerization was carried out in the column under 600 psi pressure and at 40° C. for 24 hours. The column was then washed with 20 ml water at the flow rate of 0.5 ml/min and pumped in 5 ml of 0.01 mol/I aqueous ammonium hydroxide solution. The column was sealed and kept at 120° C. for 3 hours followed by ethanol wash.

Example 17

The inhibitors such as methyl ether hydroquinone or tert-butylcatecol were removed from monomers by distillation or normal phase chromatography before uses.

A polymerization solution was prepared as Example 1, but with the following polymerization solution: 240 mg p-terphenyl, 800 mg AIBN, 16 g styrene and 16 g divinylbenzene (80%), 26.4 g mineral oil, and 21.6 g 2-ethylhexanoic acid.

An empty glass column (10 mm inner i.d. and 100 mm length), one end of which was sealed by a pressuring device shown in FIG. 4, was filled with this solution until the column was full. A TEFLON-plug contained in the PEEK screw cap shown in the same figure, was used to seal the other end of the column. The polymerization was allowed to expose to x-ray with a dosage of 600 R/hour for 72 hours at an x-ray tube voltage of 111 kVp. The obtained column was further heated to 70° C. for 2 hours. Then the column was washed with hexane followed by hexane/acetone (50/50), acetone, acetonitrile, respectively with 20 bed volume of each solvent.

The device of FIG. 4 was detached from the syringe pump after the pressure was released. The device of FIG. 4 was opened and carefully removed from the column. It was found that the height of the polymer rod was 4 mm shorter than the height of the polymerization solution inside the column. The column was then fitted with the original HPLC column fittings. The column was connected to a HPLC pump and washed with acetonitrile at 2 ml/min for 20 minutes at 45 degrees C.

The prepared column was further washed with 20 bed volume of water and compressed with the piston to get rid of the void volume. The column was then characterized using LC characterization method described in 1a. The chromatogram is attached in FIG. 9.

Alternative Versions of Example 17

Figure 9:
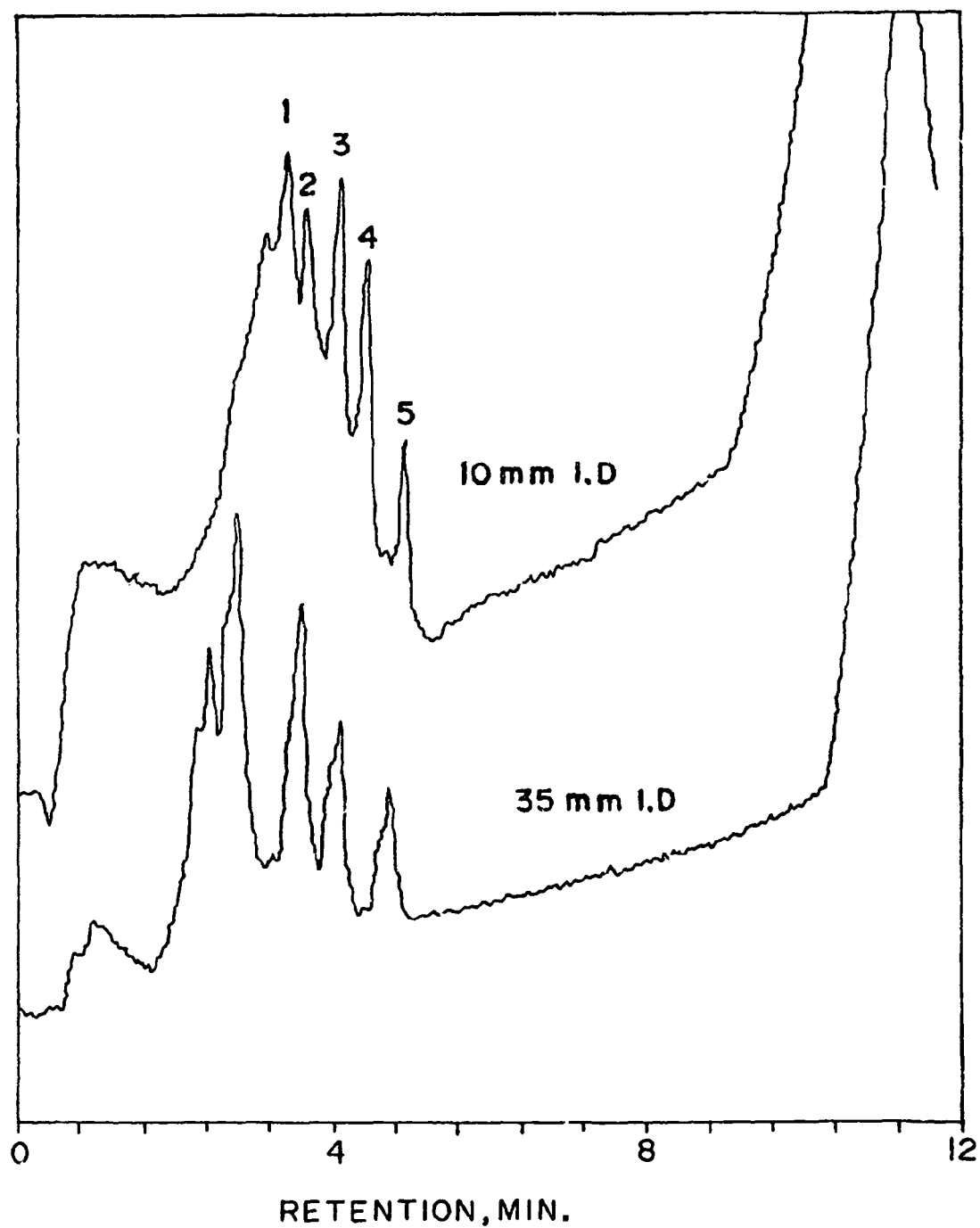
FIG. 9 is a chromatogram showing the chromatography separation achieved with medium energy (110 kEV)x-ray irradiated polymerization.

Another column was prepared as in example 17 in a glass column (35 mm i.d.×100 mm length) with the following mixture: 30 g styrene, 30 g divinylbenzene, 38.05 g mineral oil and 22.18 g 2-ethylhexanoic acid, 0.518 g p-terphenyl and 1.31 g AIBN. The columns was washed with 20 bed volume of acetonitrile and water respectively. It is characterized with LC characterization method la. The separation is shown in FIG. 9.

Another column was prepared as in example 17. The fittings from one end of the column were detached and the media was pressed out of the column by pumping 10 ml/min acetonitrile into the column through the other end. The separation media was submitted for porosimetry studies using SEM and mercury porosimeter after drying in vaccum at 50° C. for 24 hours.

Another column was prepared as in example 17 using larger diameter glass column (35 mm i.d.×100 mm length). The column was sealed with two TEFLON-plug contained in the TEFLON screw caps instead of the device in FIG. 4. The polymer was pushed out of the column and dried as above example. The polymer was submitted for SEM and porosimetry studies.

Another column was prepared as above example using large diameter column (35 mm×100 mm) but using the following polymerization solution: 240 mg p-terphenyl, 800 mg AIBN, 3.2139 g styrene, 28.8088 g divinylbenzene (80% pure), 37.4060 g 1-dodecanol, 13.25 g toluene.

Another column was prepared as above example using large diameter column (35 mm×100 mm) but using the following polymerization solution: 240 mg p-terphenyl and 800 mg AIBN was dissolved in the monomer mixture of 32.0034 g divinylbenzene (80%). Into the monomer mixture, 31.6926 g tetraethylene glycol, 16.3224 g tetraethylene glycol dimethyl ester was added.

Another column was prepared as above example within a polymeric housing described in FIGS. 12-15. The polymerization solution contains 73.2 g divinylbenzene, 73.4 g styrene, 85.2 g mineral oil, 60.8 g 2-ethylhexanoic acid, 0.882 g p-terphenyl and 2.94 g AIBN. The temperature of polymerization in the center of the column was about the same as the one on the edge of the column. The conversions of monomers were almost complete after 4 days of 110 kV x-ray irradiated polymerization. Complete reaction is attained thermally as the further exotherm has no significant bad effect.

Many other columns using different scintillators, photo initiators, monomers and porogenic solvents have been prepared. The porogenic solvents used include other alkane such as octane, alcohols such methanol, propanol and cyclohexanol, ethers such as. tetrahydrofuran, dioxane, oligomers such tetraethylene glycol, tetraethylene glycol dimethyl ether. Photo initiators used include 2-chlorothioxanthen-9-one, 4,4'-bis(dimethylamino)benzophenone, 4,4'-bis(diethylamino)benzophenone, phenanthrenequinone, diphenyl(2,4,6 trimethylbenzoyl)phosphine oxide and azo bisisobutylronitrile (AIBN). The scintillators used include 2,5-diphenyloxazole (PPO), 2-phenyl-5-(4-biphenylyl ) 1,3,4-oxadiazole (PBD), 2-(1-Naphthyl)-5-phenyloxazole (á-NPO) besides p-terphenyl and ZnSe. The monomers used include acrylonitrile, butyl methacrylate besides glycidyl methacrylate, ethylene glycol dimethacrylate, styrene, divinylbenzene, ethyl styrene.

In FIG. 9, there is shown a chromatogram of a separation in two different diameter columns of the mixture of (1) Met-Enkephalin, (2) Leu-Enkephalin, (3) Angiotensin, (4) Phyusalaemin and (5) Substances P on Poly (DVB-co-St) monolithic columns prepared by X-ray irradiation initiated polymerization in column with a diameter of 10 mm and 35 mm and a length of 65 mm; Mobile phase: (A) water with 0.15% (v/v) TFA; Gradient: 10-40% B in A in 7 bed volume at a flow rate of 5 ml/min I.D. column and 50 ml/min for 35 I.D. column: Detection: UV at 214 nm.

Figure 10:
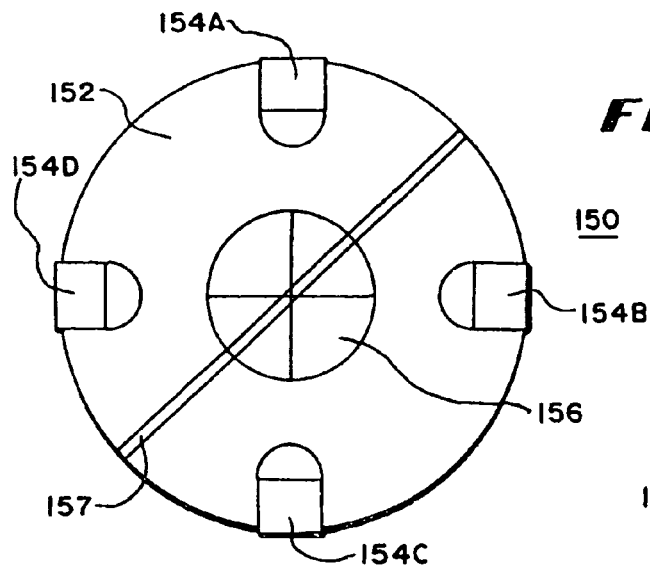
FIG. 10 is a top view of a UV or visible light polymerization apparatus for chromatographic columns.

In FIG. 10, there is shown a top view of an ultraviolet or visible light polymerization apparatus 150 having a stationary top surface 152, a rotating top surface 156, a support member 157 connected to the stationary support surface 152 and pinned to the rotating surface 156 to permit rotation thereof and four fluorescent lamp holders 154A-154D. Visible or ultraviolet fluorescent lamps are inserted in these holders.

Figure 11:
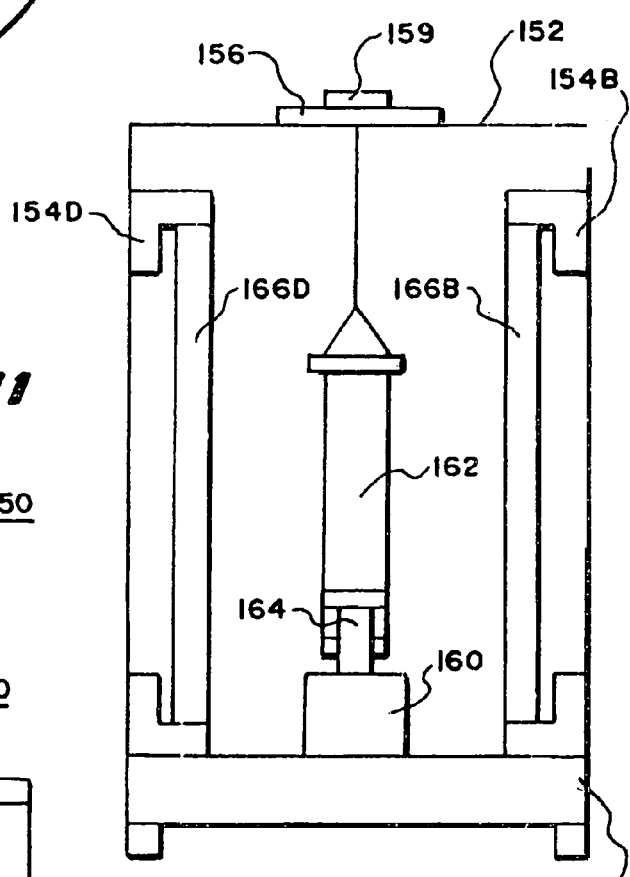
FIG. 11 is a sectional side elevational view of the apparatus of FIG. 10.

In FIG. 11, there is shown a schematic representation of a side sectional view of the polymerization apparatus 150 showing the driven member 156 rotated reciprocally by a motor 159 to rotate the polymerization apparatus 162. Two of the four lamps 166D and 166B are shown mounted to the lamp holders 154D and 154B and corresponding holders at the bottom end of the elongated lamps 166D and 166B. A piston 164 is used to pressurize the polymerization mixture at 162 during polymerization. A fan 158 aids in cooling the polymerization apparatus and reflective coatings on the cover, the sides and the lamps reflect light back into the light conducting walls of the container 162. With this arrangement, the lamps 166A-166D cause light to impinge on the polymerization mixture to initiate and control the polymerization reaction. The polymerization of relatively large diameter columns may be performed while maintaining radial uniformity in the final plug at all locations along the column in the direction of flow of the solvent and analyte. The light may be turned on and off as desired to control the temperature gradients so that the polymerization may take place under a combination of light and temperature in a controlled manner for uniformity.

Figure 12:
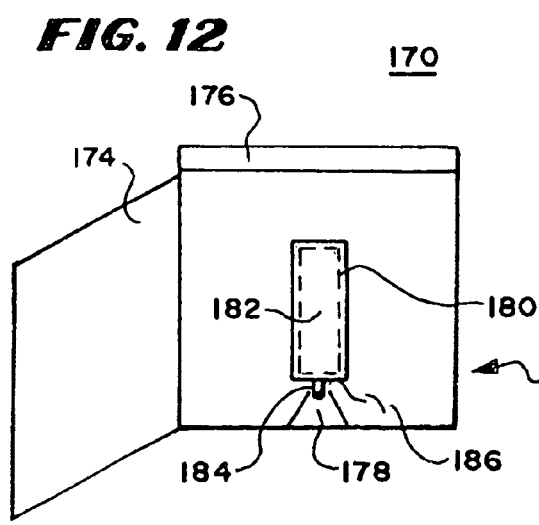
FIG. 12 is a schematic elevational view of an x-ray polymerization apparatus for chromatographic columns.

In FIG. 12, there is shown a simplified elevational view of an apparatus 170 for polymerization using principally x-ray radiation having a radiation proof cabinet 172, with a door 174, an upper window 176, a holder 178 and a container 180 to contain a reaction mixture at 182. A piston 184 may be utilized in some embodiments to pressurize the reaction mixture 182. In the apparatus 170, x-rays or other suitable radiation such as gamma rays may be used to control the reaction in the polymerization container in a safe convenient manner.

In some embodiments, pressure may be applied through the piston 184 by applying air through the conduit 186 to move the piston inwardly against the reaction mixture 182 in a manner described above in connection with other embodiments. In the preferred embodiment, the apparatus 170 is a small user friendly cabinet x-ray system resembling a microwave in that it has a door and controls mounted on the cabinet. It uses low voltage levels and can be operated by personnel safely from next to the cabinet because it has low penetration which is sufficient however for large columns. It is suitable for the polymerization of this invention because processes described hereinabove use added substances to aid in polymerization such as photo initiators, fluorescing solvents, or porogens, x-ray sensitizers and/or scintillators. This unit permits x-ray control of the polymerization and other units such as those of FIG. 10 and 11 permit other radiation control of polymerization, thus permitting for example control of polymerization with the aid of radiation up to a point and finishing the polymerization using heat to decrease the time and yet avoid destructive head build-up.

Figure 13:
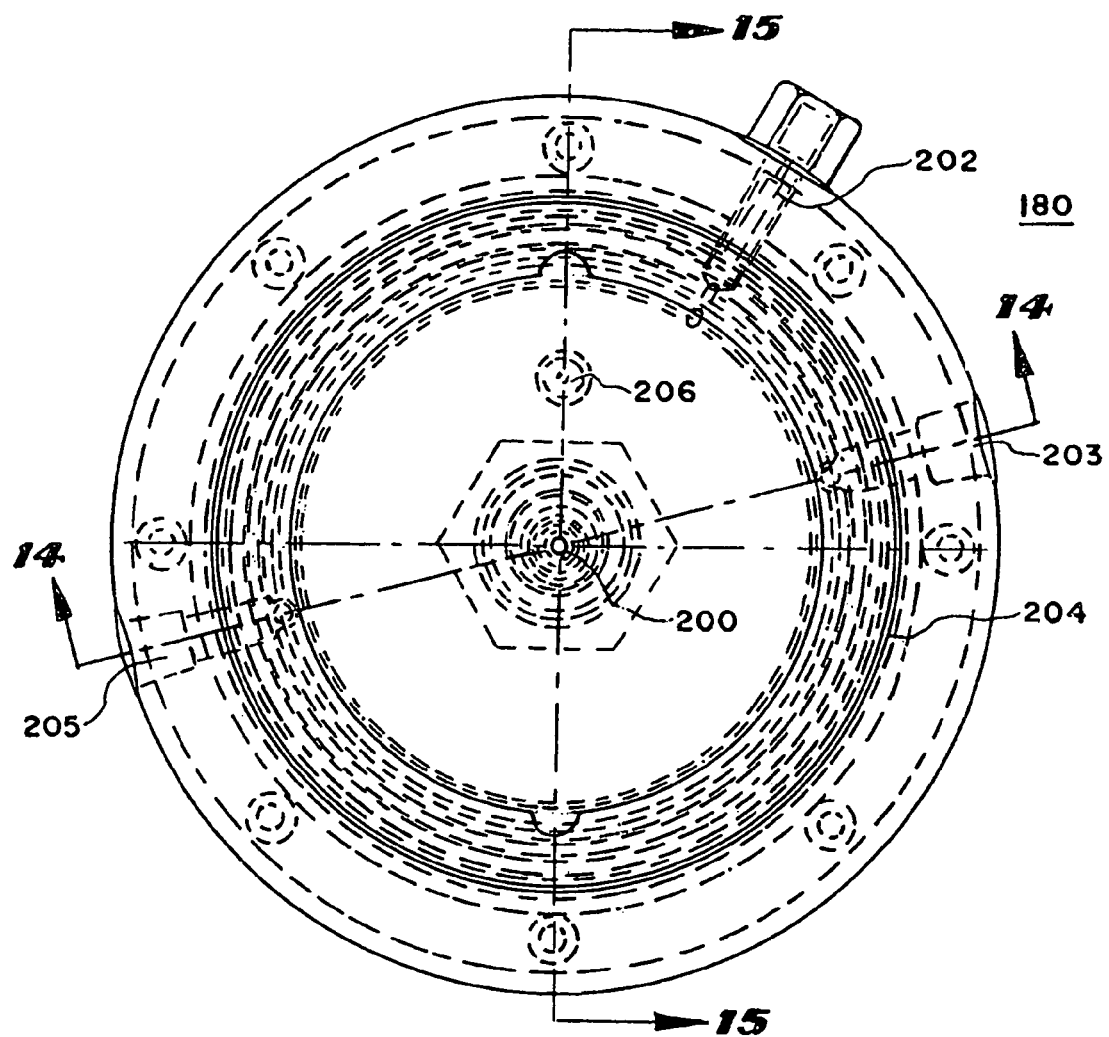
FIG. 13 is a top view of a portion of the apparatus of FIG. 12.

In FIG. 13, there is shown a top view of the reaction vessel 180 having a reactant entry opening 200, a coolant fluid inlet 203, a coolant outlet 205, a casing 204 and an overflow outlet 202. The coolant is preferably water. An opening 206 for air to move the plug 182 (FIG. 14) against the polymerization mixture AT 212 for pressure thereon is provided. A thermocoouple can be provided through the opening 200 after the reactant mixture is place by turning over the vessel 180 and a plug can be inserted there as well. With this arrangement, the reaction mixture may be irradiated under pressure if desired and subjected to x-rays axially for initiation and control of the polymerization. Water flows through it as a coolant so that the combination of radiation and pressure can control thermal gradients and promote uniformity in the final chromatography plug or support.

Figure 14:
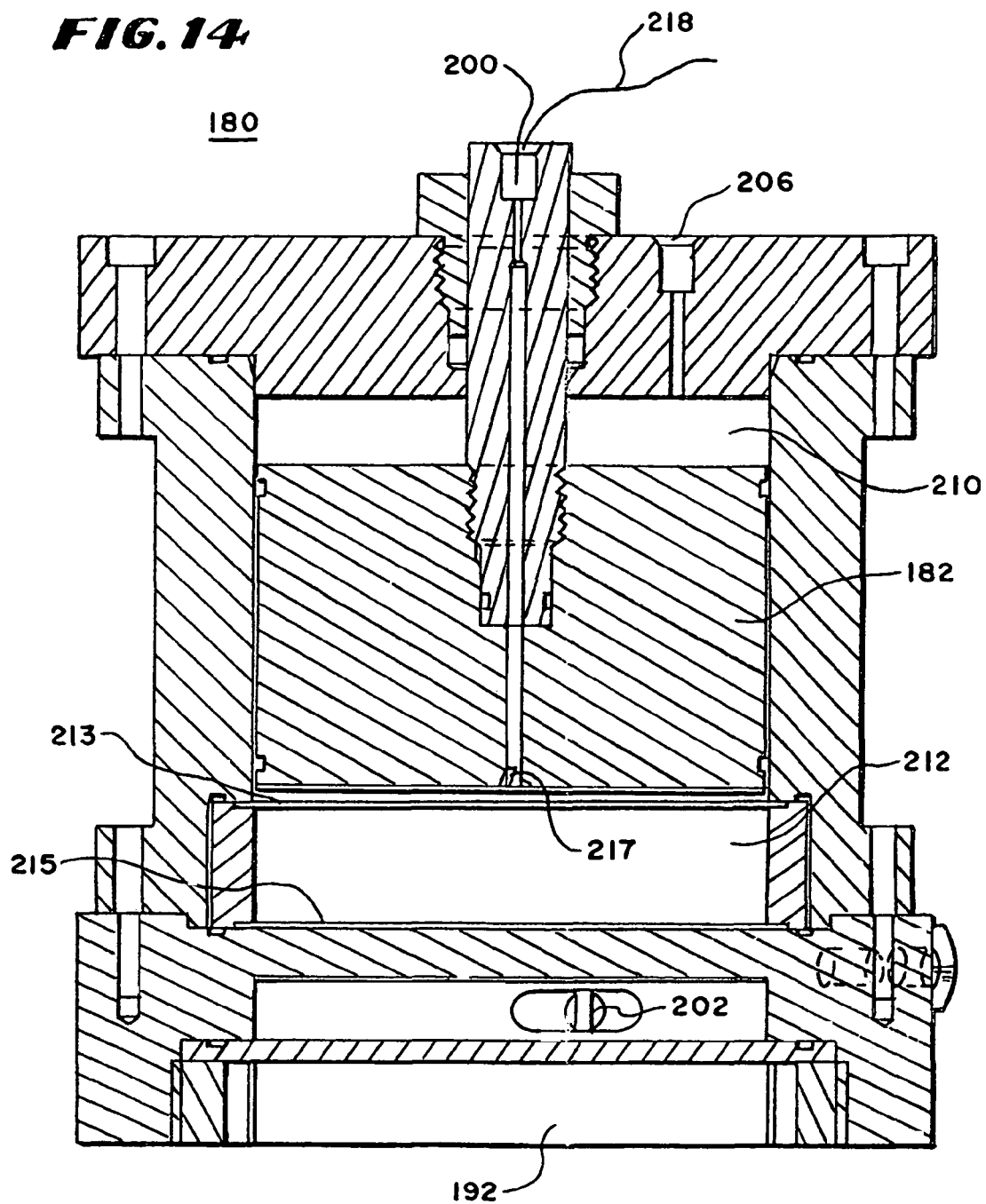
FIG. 14 is an elevational sectional view of a portion of the apparatus of FIG. 12 taken through lines 14-14.

In FIG. 14, there is shown a sectional view taken through section lines 14-14 of FIG. 13 showing the transparent x-ray radiation window 192, the port 202 for the coolant water, the opening 200 for reactant, a thermocouple 215 and its conductor 218 and a pin in that sequence, the air pressure opening 206 to move the plug 182 to pressurize the reaction mixture in 212, the reactant housing at 212 for receiving reactant mixture, a first distribution plate at 213 to distribute the solvent and analyte during chromatography when the vessel 180 is used as a column and the second distributor plate 215 to receive the solvent and analyte after separation if the column at 212 after polymerization. With this arrangement, radiation passes through the window 192 to control the polymerization of the reactant 182. This may be done under pressure applied by the plug 182.

Figure 15:
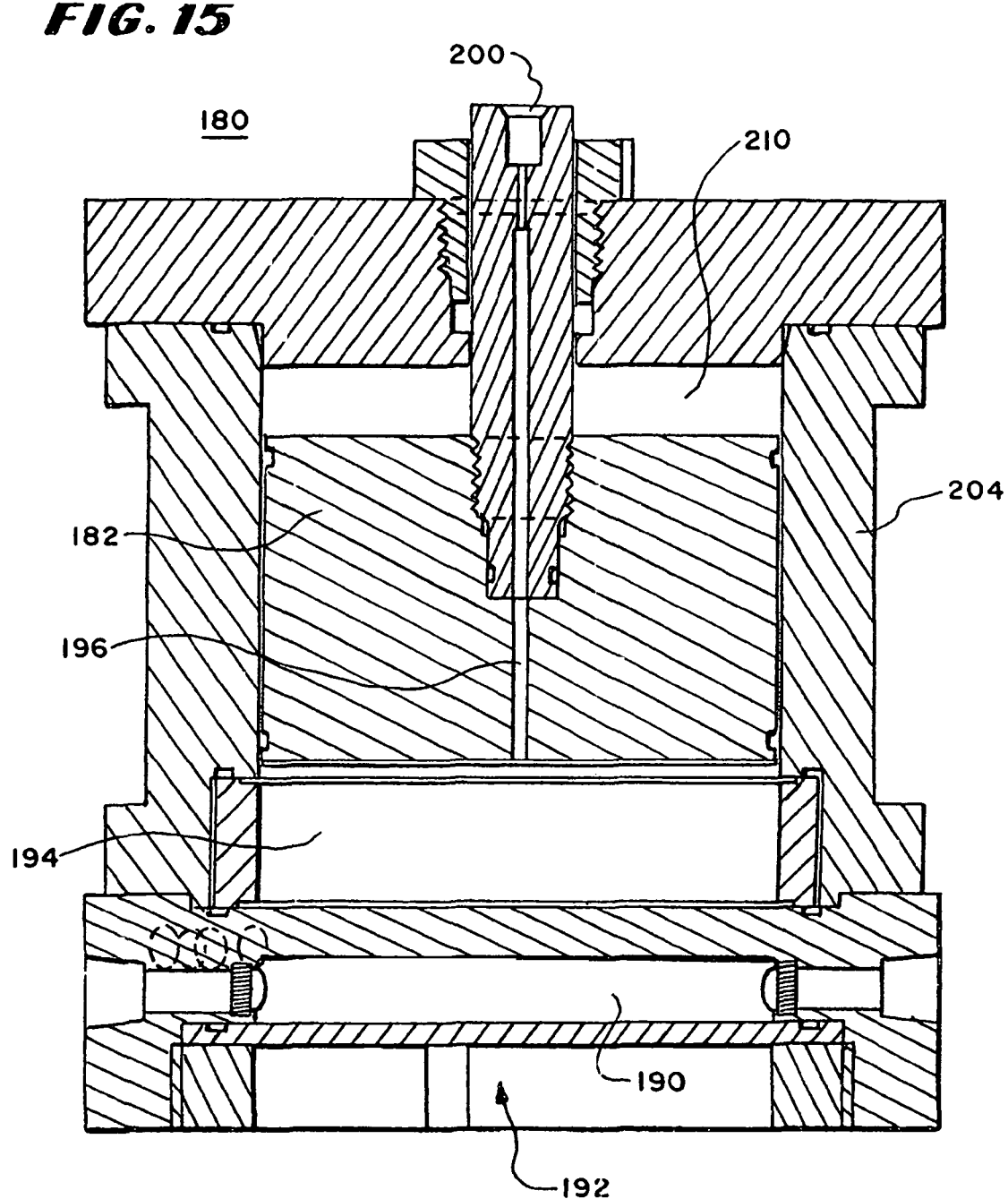
FIG. 15 is an elevational sectional view taken through lines 15-15 of FIG. 13.

In FIG. 15, there is shown a sectional view of the polymerization vessel 180 taken through lines 15-15 of FIG. 13 showing a piston 182, an air space 210 applying pressure to the plug 182 to pressurize the reactant at 212 while it is being irradiated by x-rays and cooled by flowing water in reservoir 190.

As can be understood from the above description, a polymerization mixture which may include a porogen or solvent is polymerized into a porous plug under the control of radiation. For this purpose, there is at least one substance that is caused by the radiation to effect polymerization. Some of the substances may emit radiation that effect other substances which in turn initiate or promote polymerization. For this purpose, the radiation mixture should include at least one monomer, at least a porogen or a solvent and a substance that effects polymerization. X-rays may be used with only a monomer to prepare a support. If a porogen or solvent is included, the support may be porous. The x-rays are a particularly safe type of radiation and may have wide application in forming polymeric supports. The radiation may cause polymerization or irradiate a substance such as a solvent that emits further energy that causes initiation or promotion of polymerization.

Example 18

Homopolymers, polymer resins and porous polymer support have been prepared using 110 kV x-ray irradiation. The polymers were prepared in the glass vials and columns.

A polymerization mixture containing 1% AIBN and 0.1% p-terphenyl in styrene was degassed as described in the degassing method and filled into and 1 ml glass vial. The vial was sealed with a screw cap. The vial was exposed in 600 R/hour x-ray using 111 kVp power for two days. A rigid bulk polystyrene polymer was obtained in the shape of the vial after breaking the glass of the vial.

Alternative Versions of Example 18

A homopolyglycidyl methacrylate was prepared according to the above method.

A homopolystyrene was prepared using solution polymerization according to the above method. 50% of styene in toluene containing 1% of AIBN and 0.1% of p-terphenyl was polymerized under 600 R/h x-ray for two days. Polystyrene was obtained after polymerization.

A poly(styrene-co-divinylbenzene) resin was prepared according to the above method using the following 1:1 ratio of styrene and divinyl benzene. The polymerization mixture contains 0.9 g styrene, 0.9 g divinylbenze, 17 mg AIBN, 5.7 mg p-terphenyl. The polymer resin was obtained after polymerization. Gelation happened after 5 hours of polymerization.

A poly(glycidyl-co-ethylene glycol dimethacrylate) resin was prepared according to the above method using the following 1:1 ratio of glycidyl methacrylate (GMA) and ethylene glycol dimethacrylate (EDMA). The polymerization mixture contains 0.9 g GMA, 0.9 g EDMA, 17 mg AIBN, 5.7 mg p-terphenyl. The polymer resin was obtained after polymerization. Gelation happened after 5 hours of polymerization.

A poly(glycidyl-co-ethylene glycol dimethacrylate) porous support was prepared according to the above method using the following 1:1 ratio of glycidyl methacrylate (GMA) and ethylene glycol dimethacrylate (EDMA). The polymerization mixture contains 0.45 g GMA, 0.46 g EDMA, 0.91 g cyclohexanol, 20 mg AIBN, 1.5 mg p-terphenyl. A porous polymer was obtained after polymerization. Gelation happened after 6 hours of polymerization.

A poly(styrene-co-divinylbenzene) porous support was prepared according to the above method using the following polymerization mixture contains 0.45 g styene, 0.45 g divinylbenzene (80% pure), 0.91 g cyclohexanol, 20 mg AIBN, 6.5 mg p-terphenyl. A porous polymer was obtained after polymerization. Gelation happened after 4.5 hour of polymerization.

Example 19

Silica capillary with different innerdiameters including 75 µm, 100 µm, 200 µm, 250 µm, 320 µm, 530 µm and 700 µm were modified with 1 M sodium hydroxide solution at 90° C. for 2 hours in an oven. The capillary was then washed with 60 column volumes of deionized water and acetone. It was dried by nitrogen purging through the column for 20 minutes. The capillary tubing was filled with a silanizing solution containing 50% (v/v) 3-(trimethoxysilyl)propyl methacrylate and 0.02% (w/v) hydroquinone in N,N-dimethylformamide (DMF). After both ends of the capillary were sealed, it was heated in an oven at 100° C. for about 10 h, and then washed with DMF and acetone. The capillary was dried with a nitrogen purging after wash.

Polymerization solutions were prepared as described in Example 1 with the composition of components listed in Table 1.

Each modified capillary (usually 15~20 cm) was filled with above polymerization solution. Two ends of the capillary were sealed in two 1.8 mL glass vials, respectively, which were also filled with polymerization solution. Teflon and parafilm were used to double seal the cap of the vial. About 500 µL empty space was left in each vial and the ends of the capillary locate at the half height of the vial. Two to four columns can be prepared by using the same sealing vials. The capillaries were hung vertically in the water bath at certain temperature listed in Table 1 for 20 hours by clamping the top vial on a stand. After polymerization, the monolithic capillary columns were washed with about 20 column volume organic solvent, usually acetonitrile, sometimes hexane when mineral oil was used as porogen.

The columns were characterized with the LC characterization method 1a at the flow rate of 3, 5 and 10 µl/min. Great resolutions have been achieved.

TABLE 1

Polymerization solution composition and polymerization conditions.

| Reactants | I vol % | I g | II vol % | II g | III wt % | III g | IV vol % | IV g | V wt % | V g |
|---|---|---|---|---|---|---|---|---|---|---|
| Styrene | 20 | 2.1 | 16 | 1.6 | 20 | 2.0 | 20 | 2.1 | 8 | 0.8 |
| Divinylbenzene | 20 | 2.1 | 24 | 2.5 | 20 | 2.0 | 20 | 2.1 | 32 | 3.2 |
| Tetrahydrofuran | 7.5 | 0.8 | | | | | | | | |
| chlorocyclohexane | | | 9.5 | 1.1 | | | | | | |
| THP | | | | | | | 7.0 | 0.7 | | |
| 1-decanol | 52.5 | 5.0 | 50.5 | 4.8 | | | 53 | 5.1 | | |
| Toluene | | | | | | | | | 8 | 0.8 |
| 1-dodecanol | | | | | | | | | 52 | 5.2 |
| 1-ethylhexanoic acid | | | | | 27 | 2.7 | | | | |
| Mineral oil | | | | | 33 | 3.3 | | | | |
| AIBN | 0.04 g | | | | | | | | | |
| Polymerization Temp, ° C. | 70 | | 70 | | 70 | | 70 | | 80 | |

Alternative Versions of Example 19

A monolithic capillary column was prepared as in the above example with the following polymerization solution: 0.40 g BMA, 2.6 g EDMA, 3.8 g 1-propanol, 1.6 g 1,4-butanediol, 0.6 g water and 0.04 g AIBN. The polymerization was carried out at 60° C. This column was characterized with the LC characterization method 1a with a microanalytical liquid chromatography system. The flow rate was 5 µl/min. Excellent separations of proteins were achieved.

Many other poly(acrylate) based capillary monoliths were synthesized with the variation of BMA /EDMA ratios (1/3 to 3/2) and different porogen concentrations (1-propanol with 34 to 39 wt % of the total reaction mixture while 1,4-butanediol with 20 to 15 wt %).

Another column was prepared as in Example 19 with the following polymerization mixture: 2.2 g DVB, 1.3 g styrene, 0.9 g acrylonitrile, 4.7 g mineral oil, 0.8 g toluene and 0.044 g AIBN. The polymerization temperature is 75° C. Many other columns of this type were prepared with the variation of acrylonitrile content in the polymer matrix from 0 to 50%. The polymers showed increasing hydrophilicity butdifferent retentativitiesof proteins.

Another column was prepared as in Example 19 with the following polymerization mixture: 0.8 g GMA, 2.4 g EDMA, 0.8 g ATMS, 3.1 g 1-propanol, 2.6 g 1,4-butanediol, 0.3 g water and 0.04 g AIBN. The polymerization reaction was carried out at 60° C. for 20 hours. After polymerization, the porogenic solvents in columns were washed away with aceonitrile. Then they were filled with modification solution, which is a mixture of TMA and water with volume ratio of 1 to 2 and with 0.45 g/mL TMA HCl. The modification was carried out at 40° C. for 4 hours.

Example 20

The polymerization solution is prepared as in Example 1 but with the following mixture: 3.2154 g acrylic acid, 8.0026 g methyl methacrylate, 1.6064 g glycidyl methacrylate, 19.2055 g ethylene glycol dimethacrylate, 43.8952 g 1-dodecanol, 9.0017 g cyclohexanol, 320 mg diphenyl (2,4,6 trimethyl(benzole) phosphine oxide. The polymerization mixture was sonicated for 5 minutes and poured into the column, one end of which was sealed by a TEFLON cap, then the column was sealed with another TEFLON cap. The polymerization was allowed to expose to ordinary ceiling light for 7 days. The column was washed with 20 bed volume of acetonitrile followed by 20 bed volume of water. The column was characterized with chromatography.

Alternative Versions of Example 20

A glass column of size 10 cm×1 cm ID was prepared as the above example with the following mixture: 2.5074 g glycidyl methacrylate, 2.5003 g ethylene glycol dimethacrylate, 7.5003 g p-xylene, and 58.2 mg diphenyl (2,4,6 trimethyl (benzole) phosphine oxide. The polymerization mixture was exposed to ordinary ceiling light for 24 hours. The same polymerization was carried out in another 2 ml vial for 24 hours. The conversion of monomers was 92%.

A homopolyglycidyl methacrylate was prepared in a vial with the following polymerization mixture: 10 g GMA and 0.1 g diphenyl (2,4,6 trimethyl(benzole) phosphine oxide. The solution was exposed to ordinary ceiling light for 24 hours. The polymer gelled up after 3 hours. Very clear polymer was obtained.

A homopoly(glycidyl methacrylate) was prepared in a vial with following polymerization mixture: 10 g GMA, 10 g xylene and 0.1 g diphenyl (2,4,6 trimethyl(benzole) phosphine oxide. The solution was exposed to ordinary ceiling light for 24 hours. The polymer gelled up after 3 hours. Clear polymer was obtained.

From the above description it can be understood that the novel monolithic solid support of this invention has several advantages, such as for example: (1) it provides chromatograms in a manner superior to the prior art; (2) it can be made simply and inexpensively; (3) it provides higher flow rates for some separations than the prior art separations, thus reducing the time of some separations; (4) it provides high resolution separations for some separation processes at lower pressures than some prior art processes; (5) it provides high resolution with disposable columns by reducing the cost of the columns; (6) it permits column of many different shapes to be easily prepared, such as for example annular columns for annular chromatography and prepared in any dimensions especially small dimensions such as for microchips and capillaries and for mass spectroscopy injectors using monolithic permeable polymeric tips; (7) it separates both small and large molecules rapidly; (8) it can provide a superior separating medium for many processes including among others extraction, chromatography, electrophoresis, supercritical fluid chromatography and solid support for catalysis, TLC and integrated CEC separations or chemical reaction; (9) it can provide better characteristics to certain known permeable monolithic separating media; (10) it provides a novel approach for the preparation of large diameter columns with homogeneous separation-effective opening size distribution; (11) it provides a separation media with no wall effect in highly aqueous mobile phase and with improved column efficiency: (11) it improves separation effective factors; and (12) it reduces the problems of swelling and shrinking in reverse phase columns.

Although preferred embodiments of the inventions have been described with some particularity, many variations in the invention are possible within the light of the above teachings. Therefore, it is to be understood that, within the scope of the appended claims, the invention may be practiced other than as specifically described.

What is claimed is:

1. A method of making a monolithic chromatographic column comprising the steps of:
preparing a polymerization mixture including at least one vinyl monomer, an initiator, and a porogen;
inserting said polymerization mixture into the walls of a chromatographic column
polymerizing said polymer mixture under a pressure of at least 80 psi during at least part of said polymerization, whereby sufficient pressure is applied to prevent voids from being formed caused by vacuum due to shrinkage during polymerization in a temperature controlled chamber during at least part of the time pressure is being applied to the polymerization mixture to form a polymer plug; and
washing the polymer plug to remove the porogen.

2. The method of claim 1 in which polymerizing is performed under a pressure of at least 80 psi during at least part of said polymerizing.

3. The method of claim 1 in which polymerizing is performed under a pressure of at least 150 psi during at least part of said polymerizing.

4. The method of claim 1 in which polymerizing is performed under a pressure of at least 180 psi during at least part of said polymerizing.

5. The method of claim 1 in which the pressure is applied in intervals of increasing pressures.

6. The method of claim 1 in which said pressure is sufficient to prevent voids from being formed inside the polymer plug.

7. The method of claim 1 in which said controlled elevated temperature is increased gradually during polymerization by controlling the temperature on the outside of the chamber.

* * * * *